United States Patent
Wright et al.

(10) Patent No.: US 6,697,436 B1
(45) Date of Patent: Feb. 24, 2004

(54) TRANSMISSION ANTENNA ARRAY SYSTEM WITH PREDISTORTION

(75) Inventors: Andrew S. Wright, Vancouver (CA); Bartholomeus T. W. Klijsen, Surrey (CA); Paul V. Yee, Vancouver (CA); Chun Yeung Kevin Hung, Vancouver (CA); Steven J. Bennett, Coquitlan (CA)

(73) Assignee: PMC-Sierra, Inc., Santa Clara, CA (US)

( * ) Notice: Subject to any disclaimer, the term of this patent is extended or adjusted under 35 U.S.C. 154(b) by 597 days.

(21) Appl. No.: 09/596,410

(22) Filed: Jun. 19, 2000

Related U.S. Application Data

(60) Provisional application No. 60/143,570, filed on Jul. 13, 1999.

(51) Int. Cl.$^7$ ................................................ H04K 1/02
(52) U.S. Cl. ........................ 375/296; 375/297; 330/106; 330/107; 455/108; 455/126
(58) Field of Search ................................ 375/296, 297; 330/106, 107; 455/126, 108

(56) References Cited

U.S. PATENT DOCUMENTS

| | | | |
|---|---|---|---|
| 4,291,277 A | 9/1981 | Davis et al. |
| 4,329,655 A | 5/1982 | Nojima et al. |
| 4,700,151 A | 10/1987 | Nagata |
| 4,967,164 A | 10/1990 | Sari |
| 5,049,832 A | 9/1991 | Cavers |
| 5,089,782 A | 2/1992 | Pike et al. |
| 5,093,667 A | 3/1992 | Andricos |
| 5,486,789 A | 1/1996 | Palandech et al. |
| 5,675,285 A | 10/1997 | Winters |
| 5,682,336 A | 10/1997 | Chian et al. |
| 5,818,298 A | 10/1998 | Dent et al. |
| 5,842,140 A | 11/1998 | Dent et al. |

(List continued on next page.)

FOREIGN PATENT DOCUMENTS

| | | |
|---|---|---|
| DE | 3307309 A1 | 9/1984 |
| EP | 0544117 A1 | 10/1992 |
| EP | 0881807 A1 | 6/1993 |
| GB | 2282291 A | 3/1995 |

OTHER PUBLICATIONS

A. Bateman, D.M. Haines and R.J. Wilkinson, "Linear Transceiver Architectures," 38$^{th}$ IEEE Vehicular Technology Conference, Philadelphia, PA, pp. 478–484, dated Jun. 15–17, 1988.

R.D. Stewart and F.F. Tusubira, "Feedforward Linearisation of 950 MHz Amplifiers," IEE Proceedings, vol. 135, Pt. H, No. 5, pp. 347–350, dated Oct. 1988.

J.K. Cavers, "Amplifier Linearization Using a Digital Predistorter with Fast Adaptation and Low memory Requirements," IEEE Transactions on Vehicular Technology, vol. 39, No. 4, pp. 374–382, dated Nov. 1990.

(List continued on next page.)

*Primary Examiner*—Mohammad H. Ghayour
*Assistant Examiner*—Qutub Ghulamali
(74) *Attorney, Agent, or Firm*—Knobbe, Martens, Olson & Bear, LLP

(57) ABSTRACT

A predistortion system adaptively compensates for distortion introduced along one or more amplification chains of a power amplifier system. In one embodiment, the predistortion system includes a plurality of compensation circuits, each of which is coupled to, and configured to digitally predistort an input transmission signal to, a respective amplification chain of an antenna array system. Each such amplification chain has an output coupled to a respective antenna of the antenna array system. A processing unit monitors the input transmission signals to, and corresponding output signals from, each of the amplification chains on a time-shared basis, and generates updates to the compensation parameters used the corresponding compensation circuits.

20 Claims, 61 Drawing Sheets

U.S. PATENT DOCUMENTS

| | | | |
|---|---|---|---|
| 5,867,065 A | | 2/1999 | Leyendecker |
| 5,900,778 A | | 5/1999 | Stonick et al. |
| 5,905,760 A | | 5/1999 | Schnabl et al. |
| 5,959,500 A | | 9/1999 | Garrido |
| 5,990,738 A | | 11/1999 | Wright et al. |
| 6,054,896 A | | 4/2000 | Wright et al. |
| 6,078,216 A | * | 6/2000 | Proctor, Jr. .................. 330/151 |
| 6,081,158 A | * | 6/2000 | Twitchell et al. ........... 330/149 |
| 6,081,698 A | | 6/2000 | Moriyama et al. |
| 6,275,685 B1 | | 8/2001 | Wessel et al. |
| 6,281,936 B1 | * | 8/2001 | Twitchell et al. ........... 348/470 |
| 6,342,810 B1 | | 1/2002 | Wright et al. |
| 6,356,146 B1 | | 3/2002 | Wright et al. |
| 6,388,513 B1 | | 5/2002 | Wright et al. |
| 6,459,334 B2 | | 10/2002 | Wright et al. |
| 6,476,670 B1 | | 11/2002 | Wright et al. |
| 6,489,846 B2 | | 12/2002 | Hatsugai |
| 6,587,514 B1 | | 7/2003 | Wright et al. |

OTHER PUBLICATIONS

Y. Nagata, "Linear Amplification Technique for Digital Mobile Communications," IEEE Transactions on Vehicular Technology, pp. 159–164, (1989).

E.A. Lee and D.G. Messerschmitt, "Digital Communication," Kluwer Academic Publishers, Chapter 15, pp. 566–569, (1990).

A.A.M. Saleh and J.Salz, "Adaptive Linearization of Power Amplifiers in Digital Radio Systems," The Bell System Technical Journal, vol. 62, No. 4, pp. 1019–1033, dated Apr. 1983.

Andrew S. Wright and Willem G. Durtler "Experimental Performance of an Adaptive Digital Linearized Power Amplifier," IEEE Transactions on Vehicular Technology, vol. 41, No. 4, pp. 395–400, dated Nov. 1992.

J. K. Cavers, "The Effect of Quadrature Modulator and Demodulator Errors on Adaptive Digital Predistorters for Amplifier Linearization," IEEE Transactions on Vehicular Technology, vol. 46, No. 2, pp. 456–466, May 1997.

L. Sundstrom, M. Faulkner, and M. Johansson, "Quantization Analysis and Design of A Digital Predistortion Linearizer for RF Power Amplifiers," IEEE Transactions on Vehicular Technology, vol. 45, No. 4, pp. 707–719, dated Nov. 1996.

M. Faulkner and M. Johansson, "Adaptive Linearization Using Predistortion—Experimental Results," IEEE Transactions on Vehicular Technology, vol. 43, No. 2, pp. 323–332, dated May 1994.

J. K. Cavers, "A Linearizing Predistorter with Fast Adaptation," 40th IEEE Vehicular Technology Conference, pp. 41–47, dated May 1990.

International Search Report for PCT Application No. PCT/IB00/01038.

International Search Report for PCT Application No. PCT/IB00/01044.

International Search Report for PCT Application No. PCT/IB00/01047.

International Search Report for PCT Application No. PCT/IB00/01049.

International Search Report for PCT Application No. PCT/IB00/01051.

Claims of U.S. application No. 09/596,142.

Claims of U.S. application No. 09/595,988.

Claims of U.S. application No. 09/596,962.

Claims of U.S. application No. 09/597,915.

* cited by examiner

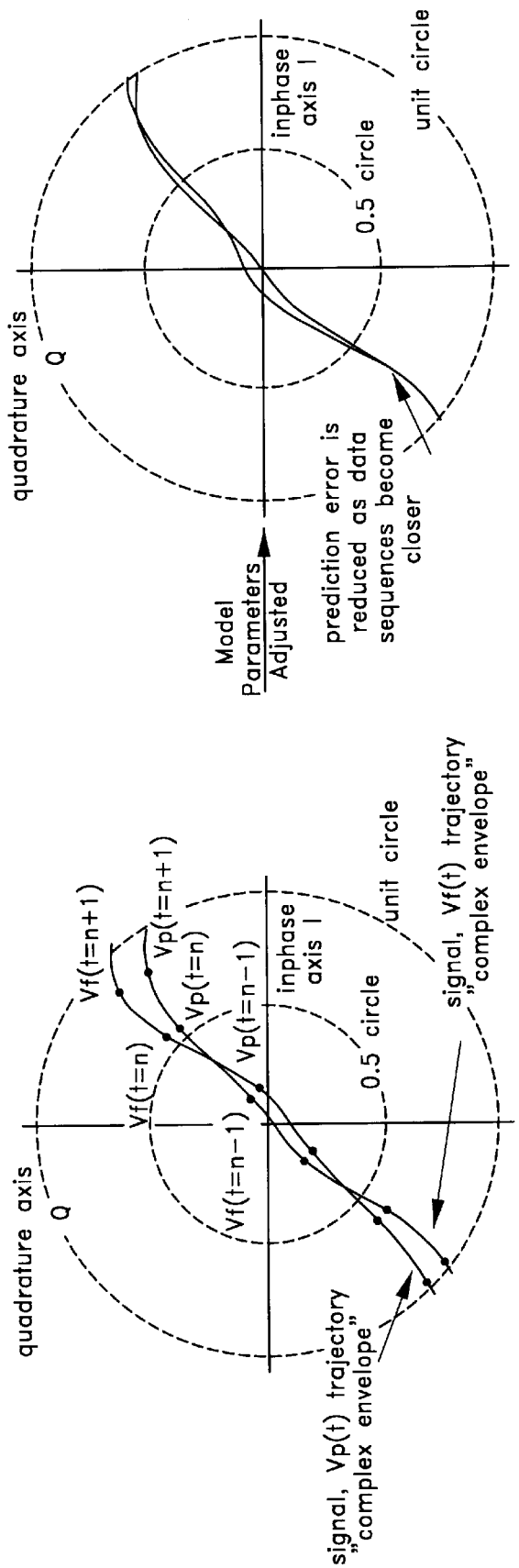

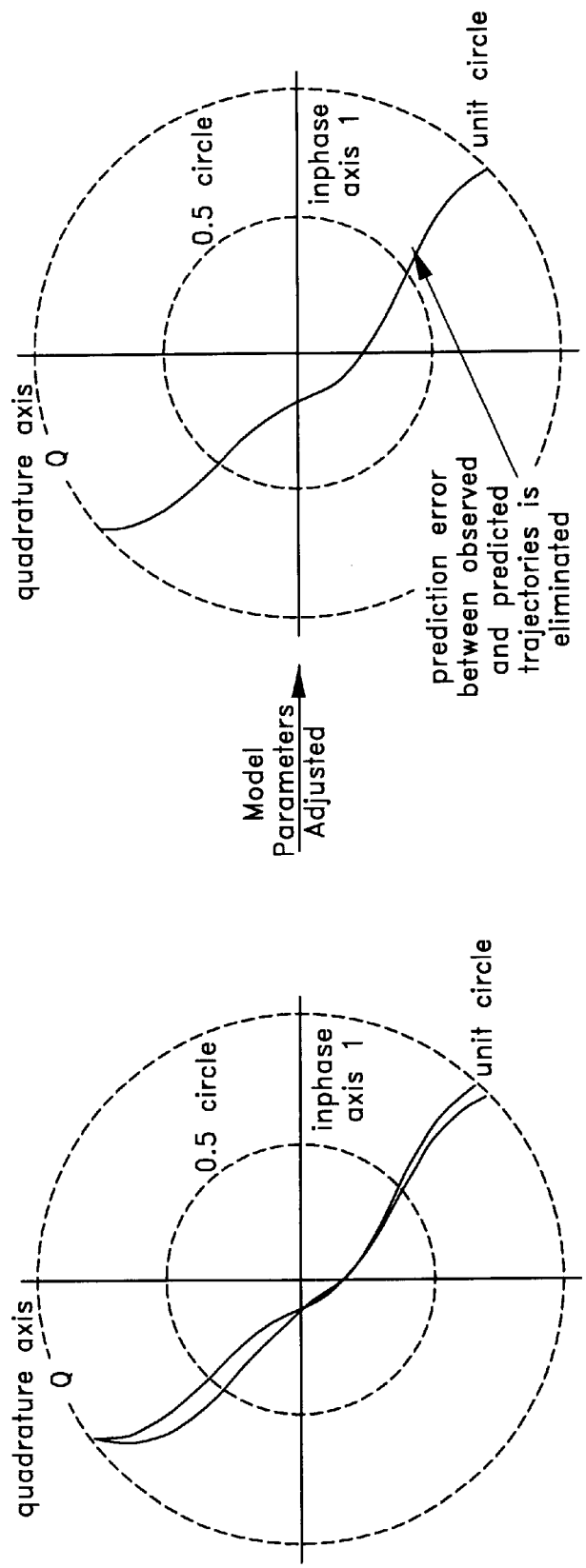

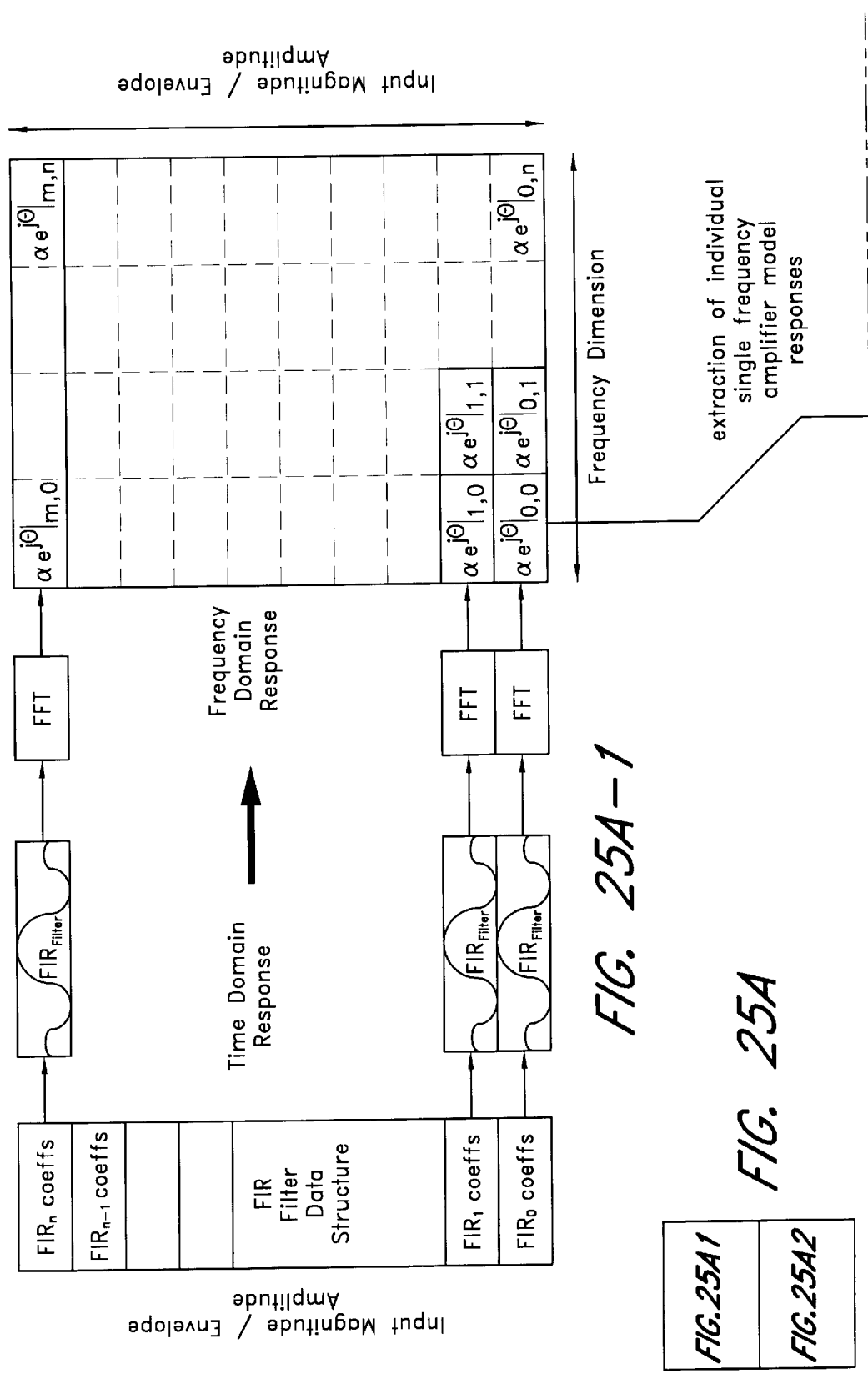

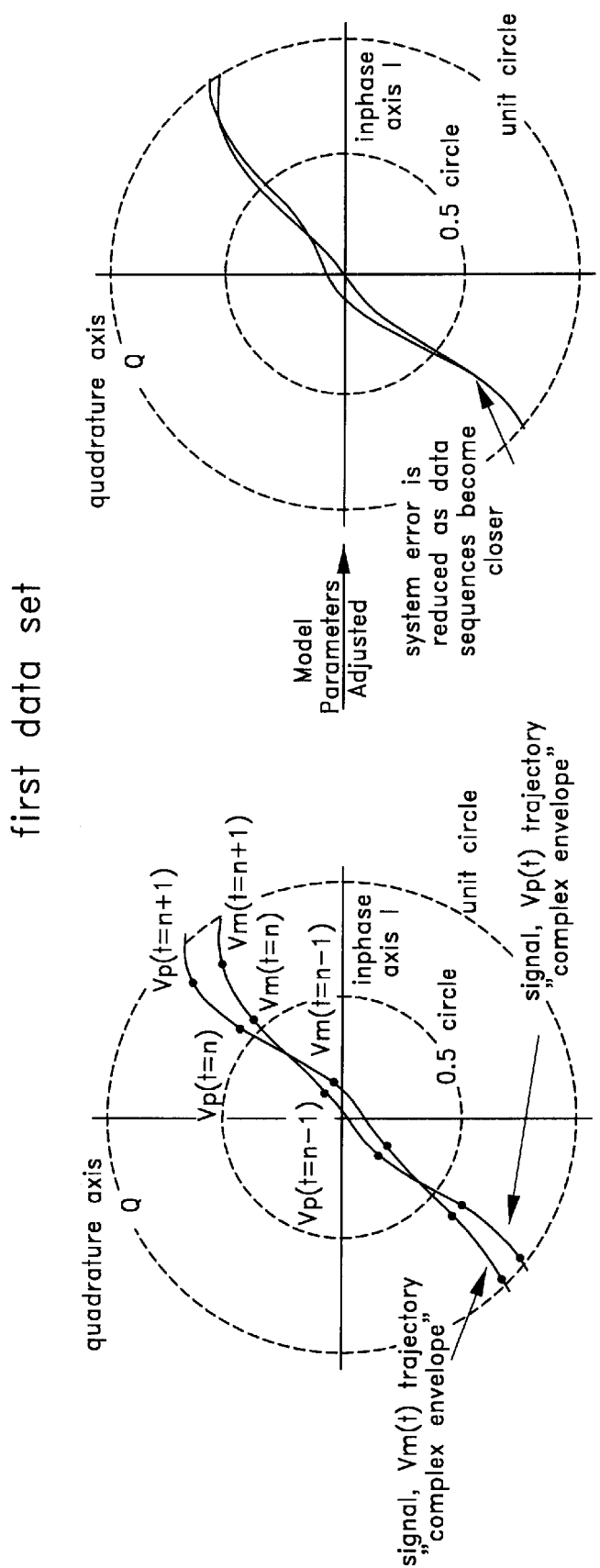

subsequent (last) data set

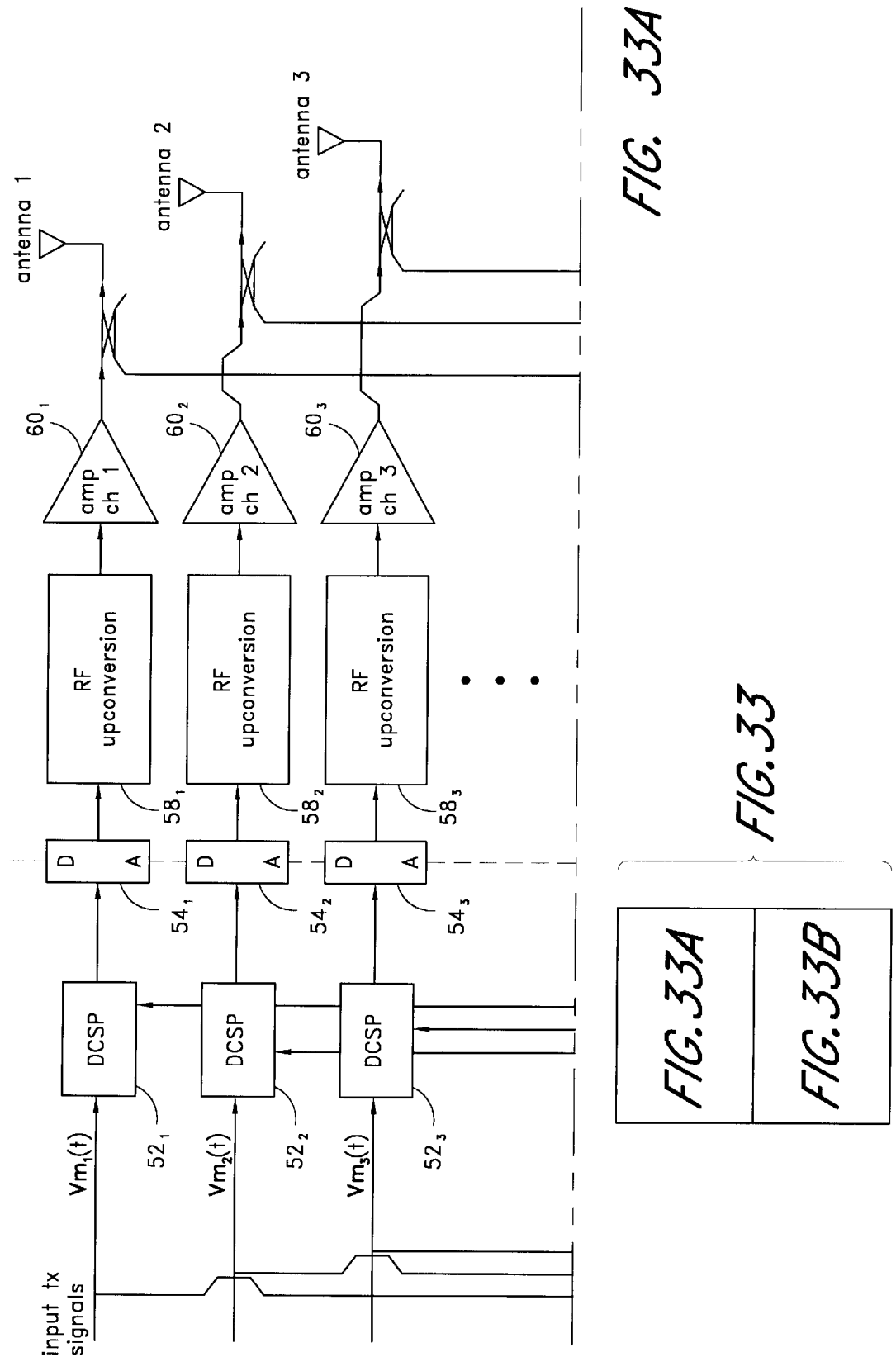

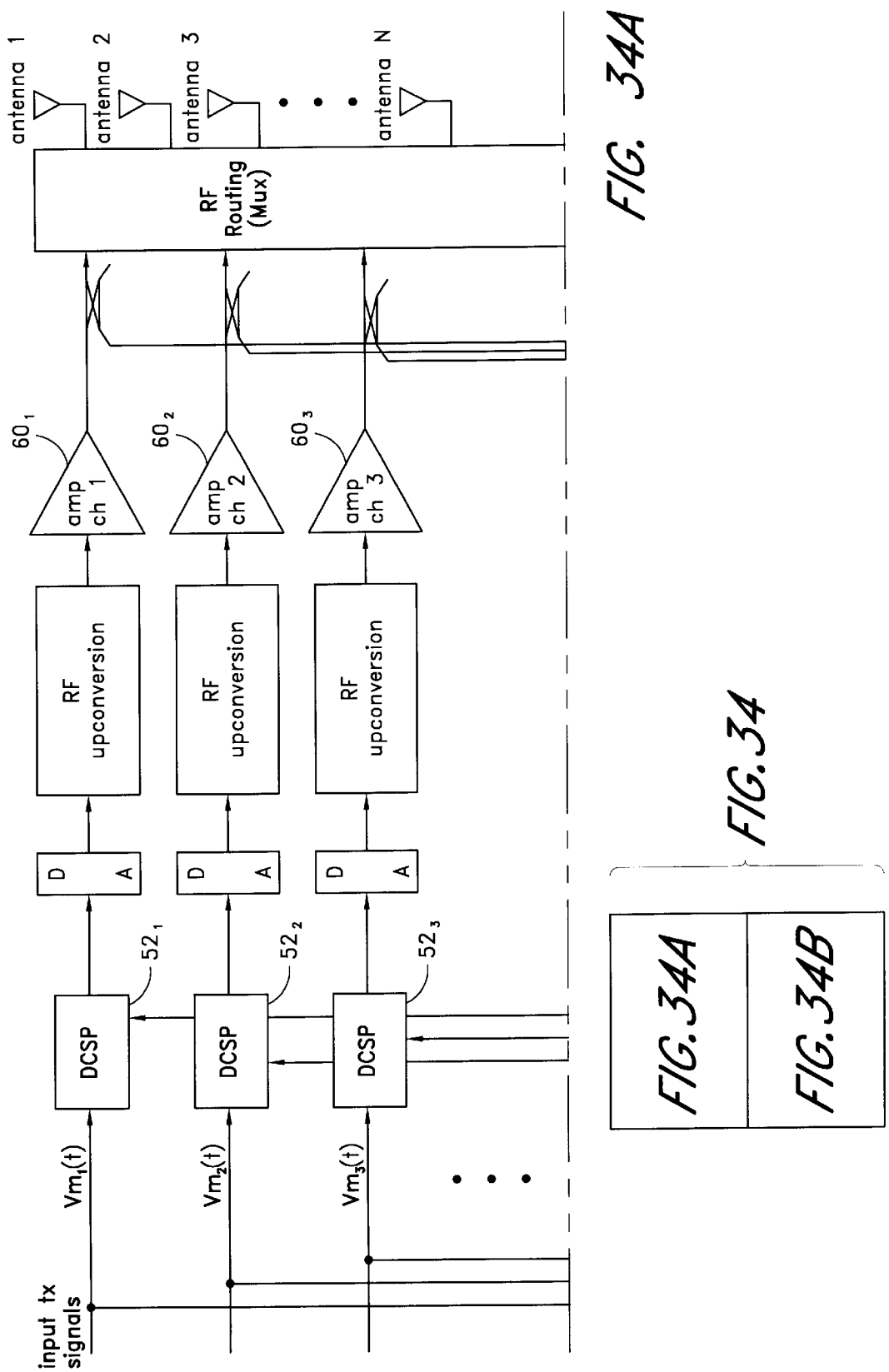

TRANSMISSION ANTENNA ARRAY SYSTEM WITH PREDISTORTION

PRIORITY CLAIM

This application claims the benefit of U.S. Provisional Appl. No. 60/143,570, filed Jul. 13, 1999, the disclosure of which is hereby incorporated by reference.

FIELD OF THE INVENTION

This invention relates to power amplifiers, and more particularly relates to predistortion circuits and methods for compensating for nonlinearities within the amplification process.

BACKGROUND OF THE INVENTION

Radio frequency (RF) power amplifiers are widely used to transmit signals in communications systems. Typically a signal to be transmitted is concentrated around a particular carrier frequency occupying a defined channel. Information is sent in the form of modulation of amplitude, phase and/or frequency, causing the information to be represented by energy spread over a band of frequencies around the carrier frequency. In many schemes the carrier itself is not sent since it is not essential to the communication of the information.

A signal which varies in amplitude will suffer distortion during amplification if the amplifier does not exhibit a linear amplitude characteristic. Perfect linearity over a wide range of amplitude is difficult to realize in practice. The signal will also suffer distortion if the phase shift introduced by the amplifier (1) varies with the signal's amplitude, or (2) is not linear over the range of frequencies present in the signal. The distortion introduced typically includes intermodulation of the components of the input signal. In addition to appearing within the bandwidth of the signal, such distortion products typically extend outside the bandwidth originally occupied by the signal, potentially causing interference in adjacent channels. Although filtering can be used to remove the unwanted out of band distortion, filtering is not always practical, especially if the amplifier is required to operate on several different frequencies.

A typical amplifier becomes significantly nonlinear at a small fraction of its maximum output capacity. In order to maintain linearity, the amplifier is therefore operated at an input and output amplitude which is low enough that the signals to be amplified are in a part of the transfer characteristic which is substantially linear. In this mode of operation, known as "backed off", the amplifier has a low supplied power to transmitted power conversion efficiency. For example, a "Class A" amplifier operating in this mode may have an efficiency of only 1%. In addition to wasting power, amplifiers operated in a backed off mode tend to be large and expensive.

One method for compensating for an amplifier's nonlinearities is known as predistortion. With traditional predistortion, an inverse model of the amplifier's nonlinear transfer characteristic is formed and is then applied to the low level signal at the input of the amplifier. The input signal is thus predistorted in a manner that is equal to and opposite from the distortion introduced during amplification, so that the amplified signal appears undistorted. To account for variations in the amplifier's transfer characteristic, the inverse model is updated based on a real-time observation of the amplifier's input and output signals.

One problem with existing predistortion methods is that they are generally based on the assumption, known as the memoryless AM-AM and AM-PM assumption, that (a) the nonlinear response of the amplifier is independent of the instantaneous frequency of the stimulating waveform, and (b) the nonlinear response of the amplifier is independent of previous amplifier input stimulus. Unfortunately, (a) and (b) generally do not hold true for wideband applications. As a result, existing predistortion techniques do not produce satisfactory results within wideband systems.

Another problem with existing predistortion techniques is that they fail to accurately take into account memory effects (effects of past stimulus) within the AM-AM and AM-PM distortion characteristic. Such memory effects are often caused by fluctuations in amplifier transistor die temperatures which occur as the result of variations in the amplitude of the signal being amplified. Failure to accurately predict and account for such memory effects can produce poor results.

The present invention addresses the above and other problems with existing predistortion schemes.

SUMMARY OF THE INVENTION

The present invention provides a wideband predistortion system and associated methods for compensating for nonlinear characteristics of a power amplifier, including the amplifier's frequency and time dependent AM-AM and AM-PM distortion characteristics. The system preferably comprises a data structure in which each element stores a set of compensation parameters (preferably including FIR filter coefficients) for predistorting the wideband input signal. The parameter sets are preferably indexed within the data structure according to multiple signal characteristics, such as instantaneous amplitude and integrated signal envelope, each of which corresponds to a respective dimension of the data structure.

To predistort the input transmission signal, an addressing circuit digitally generates a set of data structure indices by measuring the input transmission signal characteristics by which the data structure is indexed. In one embodiment, a data structure index is also generated from the output of a transistor die temperature sensor. On each sample instant, the indexed set of compensation parameters is loaded into a compensation circuit that predistorts the input transmission signal. The compensation circuit, which may be implemented in application-specific circuitry, preferably includes a finite impulse response (FIR) filter, and may also include an IQ modulator correction circuit.

The sets of compensation parameters are generated and written to the data structure by an adaptive processing component, which may be implemented using a programmed microprocessor or digital signal processor. The adaptive processing component generates the compensation parameter sets during regular amplifier operation by performing a non-real-time analysis of captured amplifier input and output signals. The adaptive processing component also preferably implements a state machine for controlling the overall operation of the amplifier system.

The adaptive processing component also implements a system identification process for measuring the characteristics of the power amplifier and generating initial sets of compensation parameters. As part of this process, stimulation signals are applied to the amplifier to measure various characteristics of the amplifier, including amplitude-dependent and frequency-dependent characteristics. The measured characteristics are used to generate a non-linear model of the amplifier. An input signal is then applied to both the amplifier and its model while monitoring a difference between the respective outputs, and the parameters of the model are adaptively adjusted until an error floor is reached. The level of complexity of the model is then increased, and the adaptive process repeated, until a desired level of model accuracy is reached. The model is then used to generate initial sets of compensation parameters—preferably using a direct inversion and/or adaptive process.

In one specific embodiment of, and application for, the invention, the predistortion architecture is used to compensate for nonlinearities in each amplification chain of an antenna array system. A compensation circuit of the type described above is provided along each amplification chain. However, rather than providing separate adaptive processing components for each amplification chain, a single adaptive processing component is used on a time-shared basis to generate and update the compensation parameters for all of the amplification chains.

In another specific embodiment of, and application for, the invention, the amplification chain includes a power splitter that feeds multiple nonlinear amplifiers. The nonlinear amplifiers are individually controlled (e.g., turned ON and OFF) to conserve power, such as during low traffic conditions. The amplification chain thus has multiple operating points, each of which corresponds to a particular combination of amplifier states. In this embodiment, the data structure is expanded, such as by adding an additional dimension, to store sets of compensation parameters for each operating point of the amplification chain.

Additional inventive features are set forth below.

BRIEF DESCRIPTION OF THE DRAWINGS

Several preferred embodiments of the invention will now be described with reference to the drawings, in which:

FIG. 23, which consists of FIGS. 23A–23D, illustrates the gradual reduction in prediction error during the model adaptation process;

Throughout the drawings, like reference numbers are used to indicate components that are similar or identical in function.

DETAILED DESCRIPTION OF THE PREFERRED EMBODIMENTS

Figure 1:
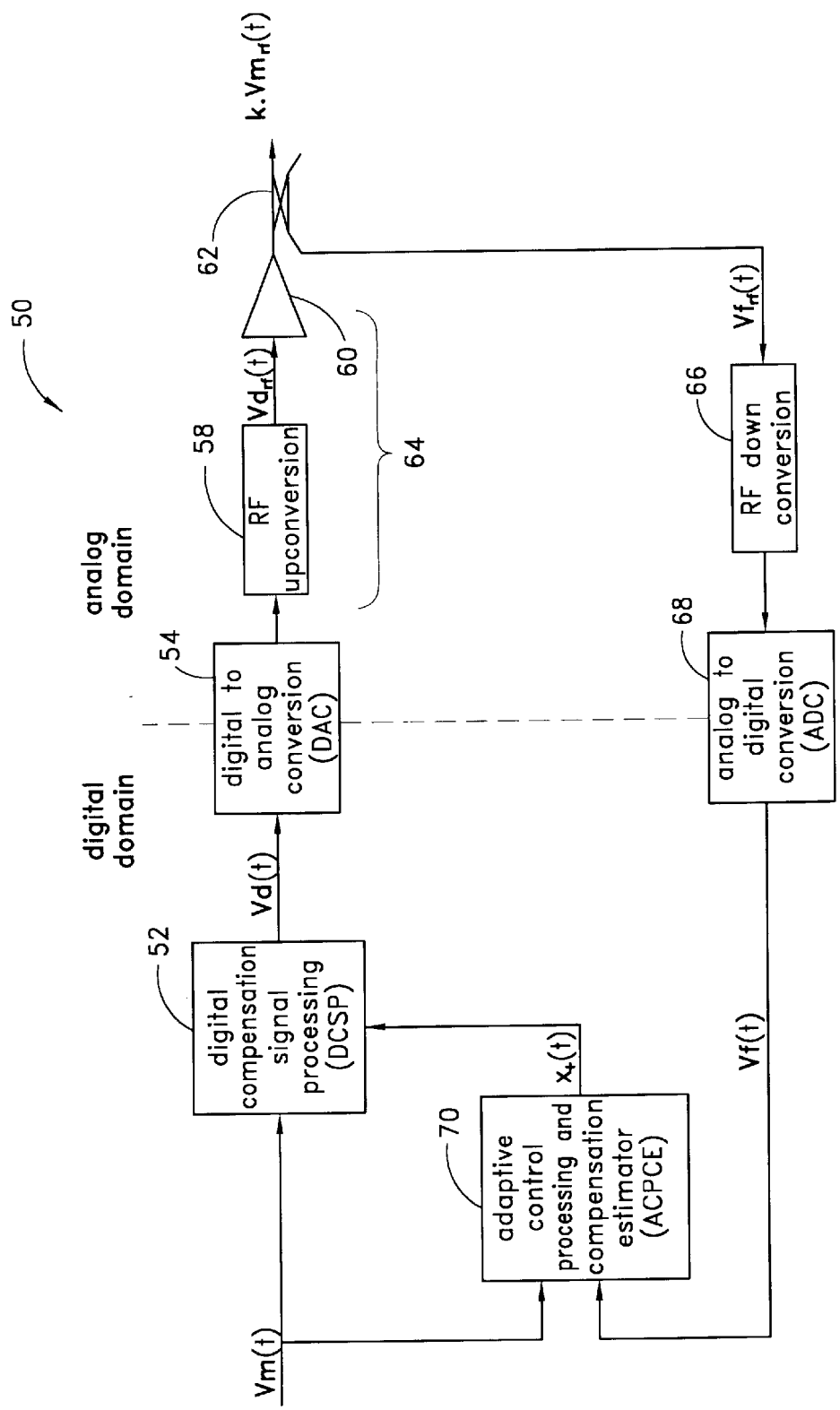
FIG. 1 illustrates an amplifier system which implements digital predistortion in accordance with a preferred embodiment of the invention.

A wideband amplifier system which implements a predistortion scheme according to the invention will now be described with reference to the drawings. Several variations, implementations, and enhancements of the basic design, and example applications for the design, will also be described. It should be understood that these various designs represent preferred embodiments of the invention, and as such, are not intended to limit the scope of the invention. The invention is defined only by the appended claims.

For convenience, the description is arranged within the following sections and subsections:

1. Overview
2. General Operation of Predistortion System
   2.1. Operation of the Open Loop Real Time Forward Path
   2.2. Operation of the Real Time Feedback and Observation Paths
3. Operation of Individual System Components
   3.1. Digital Compensation Signal Processing (DCSP) Block
      3.1.1. DCSP Construction
      3.1.2. DCSP Functional Units and Operation
         3.1.2.1. Integration Filter Construction
         3.1.2.2. Extended DCSP Compensation Architectures
      3.1.3. DCSP Theory of Operation
   3.2. Adaptive Control Processing and Compensation Estimator
      3.2.1. ACPCE Operation
         3.2.1.1. State 1: Transmit Power Off
         3.2.1.2. State 1A: Transmit Power Up
         3.2.1.3. State 1B: Transmit Power Down
         3.2.1.4. State 2: Calibration
         3.2.1.5. State 3: Training and Acquisition
         3.2.1.6. State 4: Transmission Ramp Up
         3.2.1.7. State 7: Transmission Ramp Down
         3.2.1.8. State 5: Track and Update
         3.2.1.9. State 6: Burst Idle Training
   3.3. ACPCE System Identification (SID) algorithms
      3.3.1. State 1: Algorithms, Measure Circuit Characteristics
         3.3.1.1. Power Ramping Algorithm and Measurement Signal Structure
            3.3.1.1.1. Overview
            3.3.1.1.2. Algorithm Flow Chart of Measurement Process
      3.3.2. State 2: Algorithms, Construct Amplifier and Circuit Model
         3.3.2.1. Overview
         3.3.2.2. Power Amplifier Models
            3.3.2.2.1. First Order Extended Single Kernel Nonlinear Power Amplifier Model
            3.3.2.2.2. Second Order Extended Single Kernel Nonlinear Power Amplifier Model
            3.3.2.2.3. Third Order Extended Single Kernel Nonlinear Power Amplifier Model
            3.3.2.2.4. Third Order Extended Multi Kernel Nonlinear Power Amplifier Mode
         3.3.2.3. Computation of Model Parameters
            3.3.2.3.1. Overview
            3.3.2.3.2. Step 1: Bulk Gain, Phase and Delay Estimation
            3.3.2.3.3. Step 2: Wideband FIR Response Estimation
            3.3.2.3.4. Adaptation of Model Coefficients (for the purposes of increasing model accuracy)
               3.3.2.3.4.1. Flow Diagram
               3.3.2.3.4.2. Basic LMS Adaptation Engine For Model Parameters
               3.3.2.3.4.3. Recursive Least Squares (direct form) also known as the Kalman Filter update
               3.3.2.3.4.4. Extended Kalman Filter for Nonlinear Estimation Scenarios
      3.3.3. State 3: Compute DCSP Model's Compensation Parameters
         3.3.3.1. Overview
         3.3.3.2. Initial Direct Estimation of the DCSP Coefficients
      3.3.4. State 4: Algorithms;—Adaptively Seek DCSP Compensations Parameters
         3.3.4.1. Overview
         3.3.4.2. DCSP Parameter Expansion
         3.3.4.3. DCSP Parameter Adaptation
            3.3.4.3.1. Basic LMS Adaptation Engine For Model Parameters
            3.3.4.3.2. Recursive Least Squares (direct form) also known as the Kalman Filter update
            3.3.4.3.3. Extended Kalman Filter for Nonlinear Estimation Scenarios
            3.3.4.3.4. Convolution Update
      3.3.5. State 5: Algorithms, Compute, Store and Load DCSP Correction Coefficient Parameters
      3.3.6. ACPCE System Adaptation and Tracking Algorithms
         3.3.6.1. Summary of Update Algorithms
         3.3.6.2. Non-Linear Filtered-Input Adaption Mode
4. Example Hardware Implementations
5. Variations, Enhancements And Applications
   5.1. Control of Multiple Amplifiers in a Predistorter for Maximizing Power Efficiency
   5.2. Control of Multiple Independent Amplifiers for Antenna Array Applications
   5.3. Control of Multiple Independent Amplifiers for Hot Swap Redundant Applications
   5.4. Signal Pre-Conditioning Algorithms
      5.4.1. Implementations Modes 5.4.2. Adaptive Computation and Modeling for the Composite Pre-condition/Pre-compression and Pre-distortion System by the ACPCE 5.5. Table Updating Techniques 5.6. Event Driven Capture Apparatus and Modes of Operation 5.6.1. Capture Mode 1

5.6.2. Capture Mode 2

5.6.3. Capture Mode 3

5.6.4. Capture Mode 4

5.6.5. Technology Summary 5.7. Temperature Sensor LUT operation 5.8. Utilization of Interpolation in the DCSP for Improved Noise Floor and Linearity 5.9. Multiple Memory Allocations for Different PSD Combinations/Channel Allocations 5.10. Dual FIR Filter Wideband Predistorter Construction 5.11. Functional Wideband Predistorter Construction Approach 5.12. Fast AGC Loop for Constant Operating Point 5.13. Reduction in Data Structure Noise by Localized Dimension Updating 5.14. Frequency Domain Smoothing 6. Conclusion

1. OVERVIEW

FIG. 1 illustrates an amplifier system 50 which implements a wideband predistortion scheme according to a preferred embodiment of the invention. The amplifier system 50 comprises the following components and functional blocks; a Digital Compensation Signal Processor (DCSP) 52, a generalized digital to analog converter (DAC) 54, a radio frequency (RF) upconversion block 58 coupled to a nonlinear amplifier (or assembly of nonlinear amplifiers) 60, an amplifier sampling structure (coupler) 62 (e.g., a Lange, Hybrid or Quadrature coupler), an RF downconversion block 66, a generalized analog to digital converter (ADC) 68, and an Adaptive Control Processing and Compensation Estimator (ACPCE) 70.

The analog circuitry provided along the path between the DAC 54 and the coupler 62 will be referred to generally as the "amplification chain" 64, or more generally as the "amplifier." Although the amplification chain is illustrated in FIG. 1 as consisting of an RF upconversion block 58 and a single nonlinear amplifier 60, it should be understood that the chain 64 may include additional nonlinear amplifiers and/or other types of analog circuits.

In FIG. 1 and throughout the description of the various embodiments, it may be assumed that the input transmission signal, Vm(t), is a wideband signal. More specifically, it may be assumed that Vm(t) has at least one, and preferably all, of the following characteristics: (a) the signal stimulates the amplifier system 50 at one or more frequencies within an operating bandwidth within a time interval that is the reciprocal of the total information bandwidth; (b) the signal consists of multiple information bearing subcarriers and has a spectral occupancy that exceeds 0.1% of the RF carrier frequency; and (c) the signal's bandwidth is such that the variation in the amplifier's AM-AM and AM-PM response may not be considered constant over the operating bandwidth. In addition, it may be assumed that Vm(t) has phase and amplitude varying envelopes.

The basic objective of the wideband predistorter design is to digitally compensate the wideband input signal, Vm(t), such that after RF upconversion and amplification by a nonlinear amplifier 60, the output of the amplifier unit will be a scaled replica of the input signal, $kVm_{rf}(t)$. The degree of scaling is usually defined by the bulk amplifier gain, k. To achieve this goal, the input signal, Vm(t), is processed by the Digital Compensation Signal Processor (DCSP) 52. This compensation processing is undertaken to correct for all upconversion linear imperfections and the nohlinearity of the amplifier 60. The compensation is undertaken such that the output signal from the DCSP, Vd(t), is distorted in a manner that is complementary, i.e., opposite in nature, to that incurred by the RF upconversion and amplification process. The complementary distortion is such that the composite of the distortion introduced by the DCSP 52 and by the RF upconversion and amplification processes effectively cancel each other, resulting in a linearly amplified (scaled) version of the input signal Vm(t).

The Adaptive Control Processing and Compensation Estimator (ACPCE) 70 is responsible for, among other things, estimating of the behavior of the amplification chain 64, including both linear and nonlinear imperfections. The ACPCE operates by capturing digital samples of the input signal Vm(t), and of a signal Vf(t) that represents the output of the power amplifier system 50. The signal Vf(t) is preferably derived by feeding the output of the RF power sampling coupler 62, $Vf_{rf}(t)$, to the RF downconverter 66, and by passing the RF downconverter's output to an IF or baseband ADC 68.

The Adaptive Control Processing and Compensation Estimator (ACPCE) 70 computes and eliminates the time delay difference between digital samples of the observed amplifier output and the ideal input signal. Once this has been achieved the ACPCE 70 can accurately determine the update adjustment, if required, that is to be made to the correction coefficients being used by the Digital Compensation Signal Processing (DCSP). Update adjustments are provided to the DCSP via a state parameter update vector $x_+(t)$ that contains one or more sets of correction parameter updates.

Figure 31A:
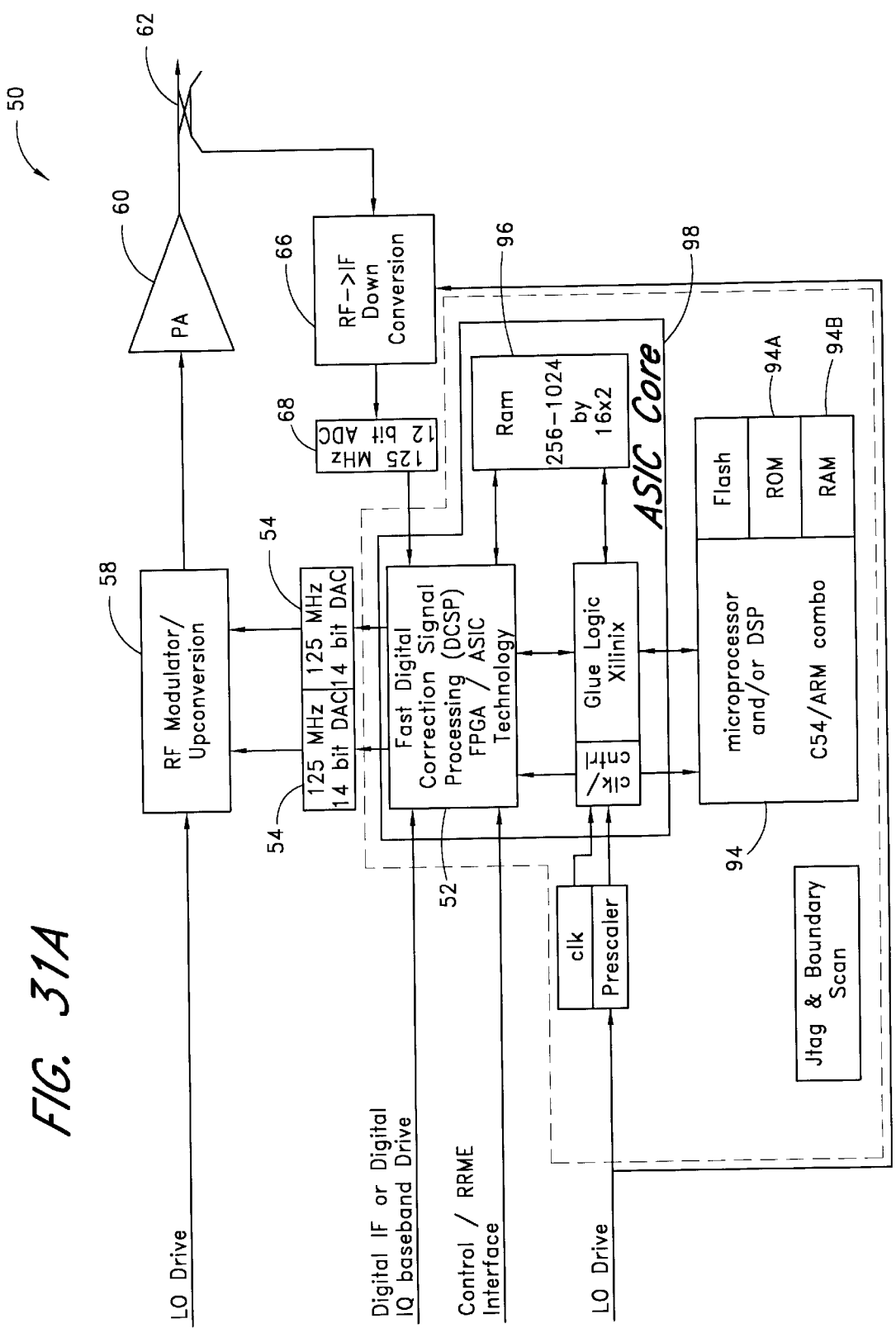
FIG. 31A illustrates how the amplifier system of FIG. 1, and particularly the predistortion units, may be implemented within hardware.
Figure 31B:
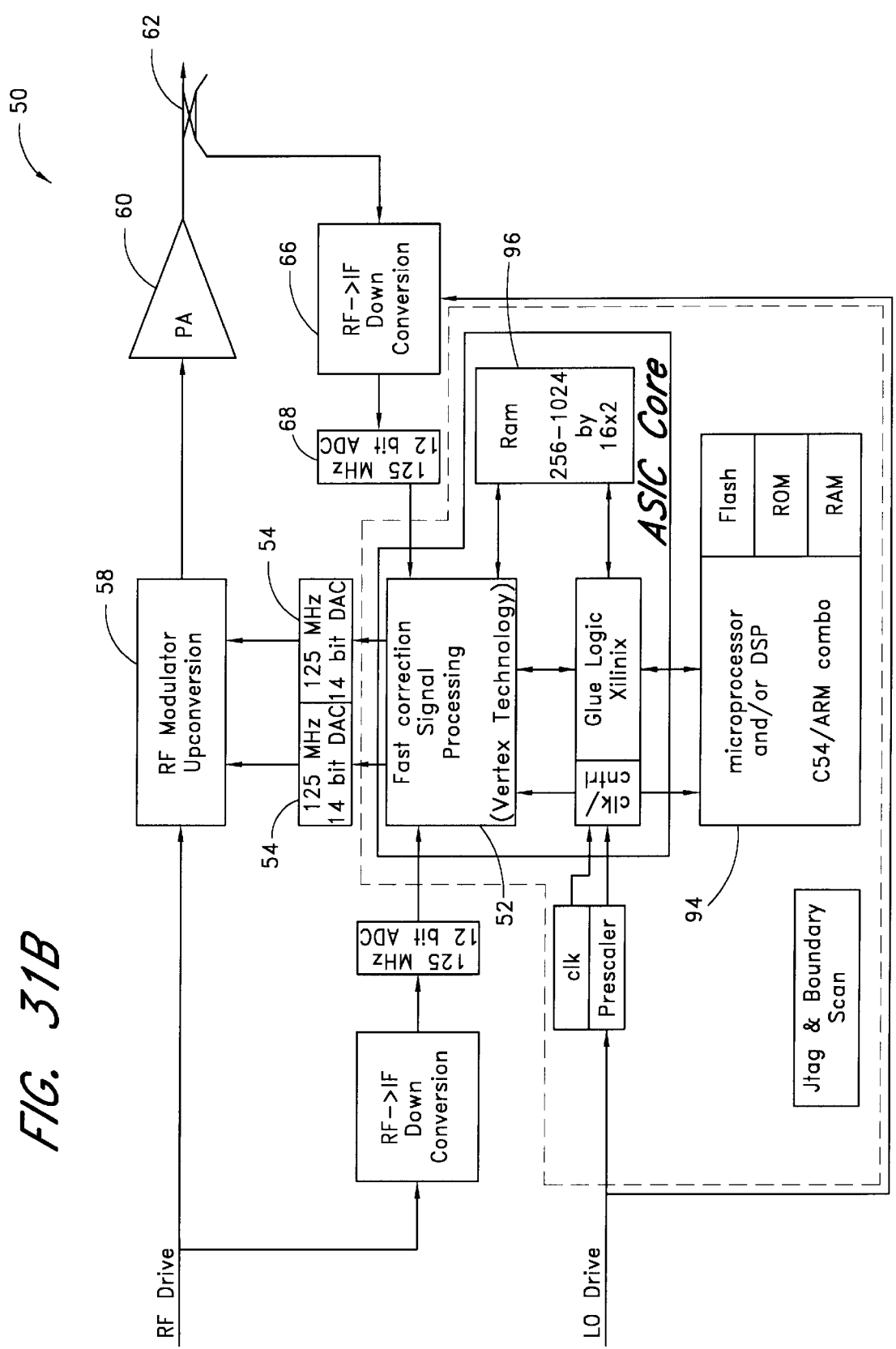
FIG. 31B illustrates a hardware implementation that may be used if a digital baseband data source is not available.

In a preferred embodiment, the DCSP 52 is implemented using application-specific circuitry such as an ASIC (application-specific integrated circuit), ASSP (application-specific standard package) and/or an FPGA (field programmable gate array), and the ACPCE 70 is implemented using one or more DSPs (digital signal processors) and/or general purpose microcontrollers that implement that various control and compensation algorithms. Example hardware implementations of the DCSP and ACPCE components are shown in FIGS. 31A and 31B and are discussed below.

An important aspect of the invention involves features of the DCSP-52 that allow wideband signals to be successfully predistorted within an amplifier that exhibits memory and AM-AM and AM-PM characteristics that are not constant over the operating frequency. Another important aspect involves the adaptive control algorithms (executed by the ACPCE) that control the amplifier and compute parameter updates for the DCSP. These and other aspects of the invention are described in the following sections. For convenience, the components that are used to implement a predistortion scheme according to the invention will be referred to collectively and generally as the "predistortion system," and the associated architecture will be referred to as the "predistortion architecture."

2. GENERAL OPERATION OF PREDISTORTION SYSTEM

Figure 2:
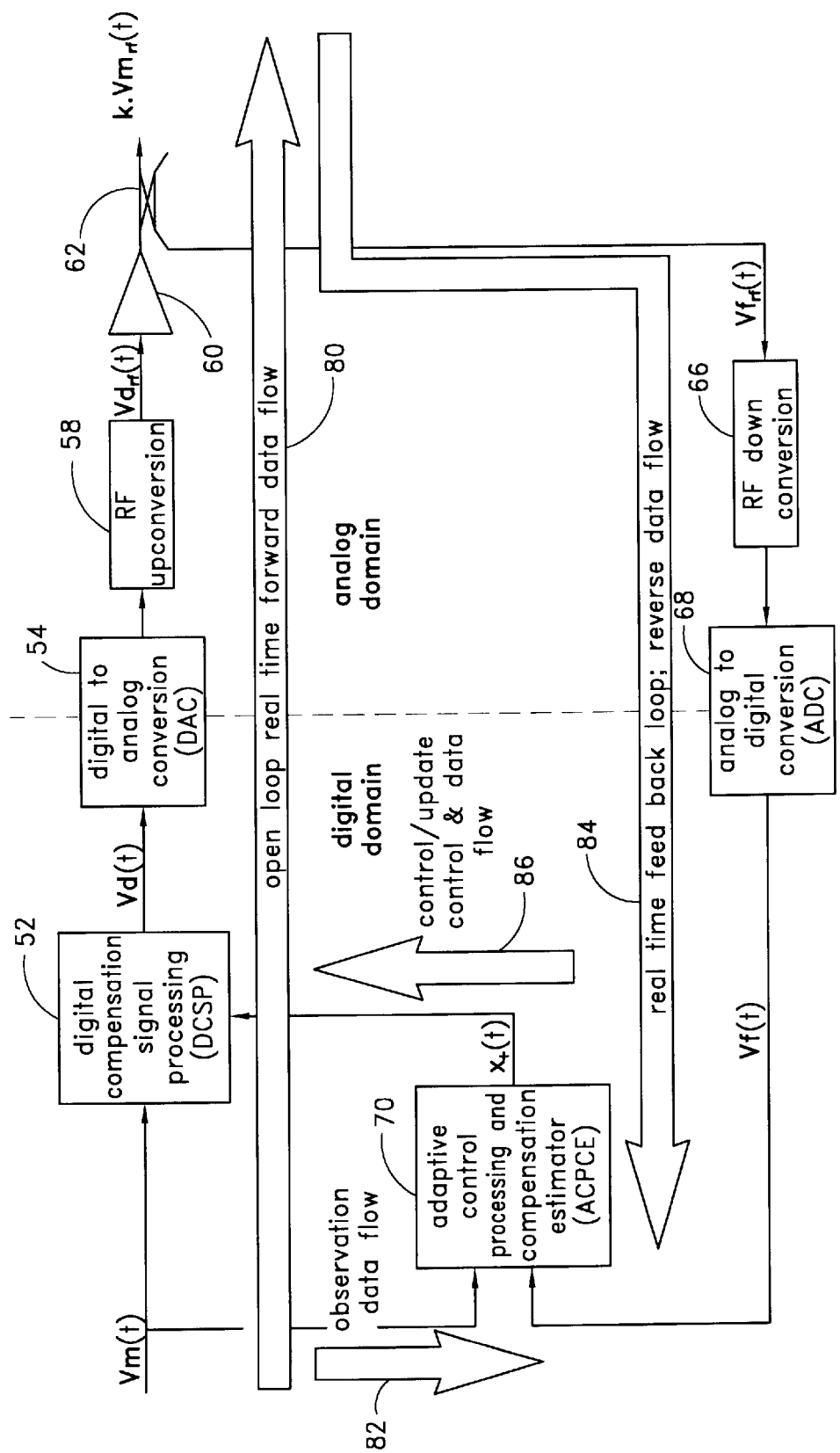
FIG. 2 illustrates the flow of information within the amplifier system of FIG. 1.

FIG. 2 illustrates the flow of information within the amplifier system 50. As illustrated in FIG. 2, the predistortion architecture generally employs four data flows or paths 80, 82, 84, 88. The open loop real time forward path 80 is concerned with the direct flow of information signals from the applied input signal through to the amplifier load. This path operates in real time. A relatively high signal processing sample rate, such as between 8× and 16× times the bandwidth of the complex bandlimited input signal Vm(t), is preferably used to ensure that the nonlinear imperfections of the amplifier may be corrected by generating a complementary wideband predistorted drive signal Vd(t).

As further illustrated by FIG. 2, the ACPCE 70 receives signal samples along two real time data paths: an observation path 82 and a feedback path 84. The observation path 82 provides the ACPCE with samples of the input signal, Vm(t), and the feedback path 84 provides the ACPCE with downconverted samples of the amplifier's output. The ACPCE uses these samples to compute compensation parameters that are provided to the DCSP along an update and control path 86.

The ACPCE 70 preferably computes compensation parameters in an off-line mode using previously-captured samples of the amplifier's input and output signals. Such non-real-time processing is possible because the imperfections in the amplification chain 64 change very slowly compared to the rate of change of the input signal Vm(t). An important benefit of this feature is that the ACPCE can implement complex compensation estimation algorithms that would be impractical to implement in real time. Another benefit is that these algorithms can be implemented in firmware, rather than in more expensive application-specific circuitry. The specific algorithms implemented in a preferred embodiment of the ACPCE are described in subsequent sections.

2.1. Operation of the Open Loop Real Time Forward Path

In practice, a complex baseband signal Vm(t) that is intended to be amplified is applied to the input of the DCSP 52. If Vm(t) is only available as a real passband digital IF or real analog RF passband signal, it is converted to a complex baseband representation. As recognized by those skilled in the art, this can be achieved by utilizing standard techniques such as Hilbert transforms and digital mixing. The DCSP may deliberately add one or more of the following effects to the input signal, as required to correct for errors introduced in the analog upconversion and amplification path: phase rotation, propagation delay, amplitude gains, DC offsets and IQ cross talk. The amount of compensation is ideally just commensurate with that required to cancel the imperfections incurred by the analog upconversion and the nonlinear AM-AM and AM-PM response of the amplifier. The DCSP provides the digitally compensated/predistorted signal Vd(t) to the generalized digital to analog converter (DAC) 54.

The generalized DAC block 54 captures a variety of possibilities by which a complex baseband signal such as Vd(t) can be imposed upon an RF carrier to form the RF signal, $Vd_{rf}(t)$. One potential technique is to use direct conversion from complex baseband to RF by utilizing a quadrature upconverter. This approach involves using two standard digital to analog converters (DACs) to generate an analog complex baseband signal that is applied to the RF upconverter 58. However, this approach is often undesirable because practical quadrature modulators incur significant degradations due to DC offsets and IQ crosstalk (IQ phase and amplitude imbalance). An alternative approach is to deliberately generate a digital IF signal by performing a complex baseband to digital IF conversion which generates a real digital IF signal that uses a DAC to generate a real passband low IF signal that may be upconverted to RF. This approach is preferable because a perfect quadrature conversion is achieved within the digital domain which incurs no imperfection. Furthermore, the approach is advantageous because only a single DAC is required per RF channel. The approach may, however, require a more costly upconversion process.

The RF passband signal $Vd_{rf}(t)$ is applied to the input of the nonlinear amplifier 60. Since the signals may exhibit a fluctuating envelope and the nonlinear amplifier 60 is characterized by an AM-AM and AM-PM distortion characteristic, the RF passband signals will be amplified whilst incurring distortion. However, if the complex predistortion invoked by the DCSP 52 is accurate, the complementary baseband distortion will cancel with the distortion incurred by the amplifier 60. This will cause the output of the amplifier 60 to be a replica of the input signal Vm(t), but at a significantly higher power level characterized by the gain of the amplifier k. Thus, the amplifier output is defined as $kVm_{rf}(t)$, where $Vm_{rf}(t)$ is a real RF passband signal equivalent of the complex baseband input signal Vm(t). The amplifier output is fed to the amplifier load via the coupler 62, which feeds a small portion of the amplifier's output signal into the feedback path 84.

2.2. Operation of the Real Time Feedback and Observation Paths

A sample of the energy fed to the amplifier load, $Vf_{rf}(t)$ (where $Vf_{rf}(t)=\alpha kVm_{rf}(t)$ and $\alpha$ is the sampling coupler's transmission coefficient), is downconverted to digital complex baseband via the RF downconversion and generalized analog to digital conversion process. As described in the previous section for the analogous generalized digital to analog converter 54, various techniques are available to those skilled in the art which permit cost, complexity and imperfection trade-offs to be made. Thus the real RF passband signal, $Vf_{rf}(t)$, is translated to a complex baseband equivalent signal, Vf(t), which may be used by the ACPCE 70. As indicated above, the ACPCE also receives the input complex baseband signal, Vm(t), provided by the data/signal source.

The ACPCE 70 uses these two signals, Vm(t) and Vf(t), to determine the remaining level of imperfection in the analog upconversion and amplification processes for which correction is needed, including AM-AM and AM-PM non-linearities of the amplifier 60. The ACPCE uses this information to compute updates to the existing correction parameters. As noted above, updates to compensation parameters need not be calculated in real time because the process being controlled is actually much slower than the rate of change observed in the input signal Vm(t). This permits the open loop wideband predistortion linearized amplifier design to be controlled with an off-line closed loop controller. This is an extremely advantageous design approach because it does not place an operating bandwidth constraint upon the design. Typical real time closed loop systems are constrained by the loop delay which infers a finite operating bandwidth which is generally 10× lower than the open loop bandwidth.

The new parameters calculated by the ACPCE 70 are provided to the DCSP 52 via $X_+(t)$, which is a vector of the latest estimates of the correction parameter values. After each new parameter set has been provided to the DCSP 52, the ACPCE 70 selects or captures another set of data samples for processing. This cycle of capturing new signal samples and calculating parameter updates may take several seconds, depending upon the processing power of the ACPCE and the complexity of the algorithms used. Where more frequent parameter updates are desired, the ACPCE may be provided with multiple microcontrollers or DSPs that independently calculate parameter sets in overlapped, interleaved cycles. For example, if the cycle time is two seconds, two DSPs can be used (with each configured to start a new cycle in the middle of the other's cycle) to provide parameter updates every one second.

3. OPERATION OF INDIVIDUAL SYSTEM COMPONENTS

The individual components or blocks of the amplifier system 50 will now be described in further detail. Abbreviated descriptions are provided for those components that can be implemented using standard digital signal processing or RF/IF engineering techniques.

3.1. Digital Compensation Signal Processing (DCSP) Block

This section details the operation of the DCSP 52. Additional DCSP design options and features are described in later sections (see, e.g., Sections 5.5, 5.6 and 5.10).

3.1.1. DCSP Construction

Figure 3:
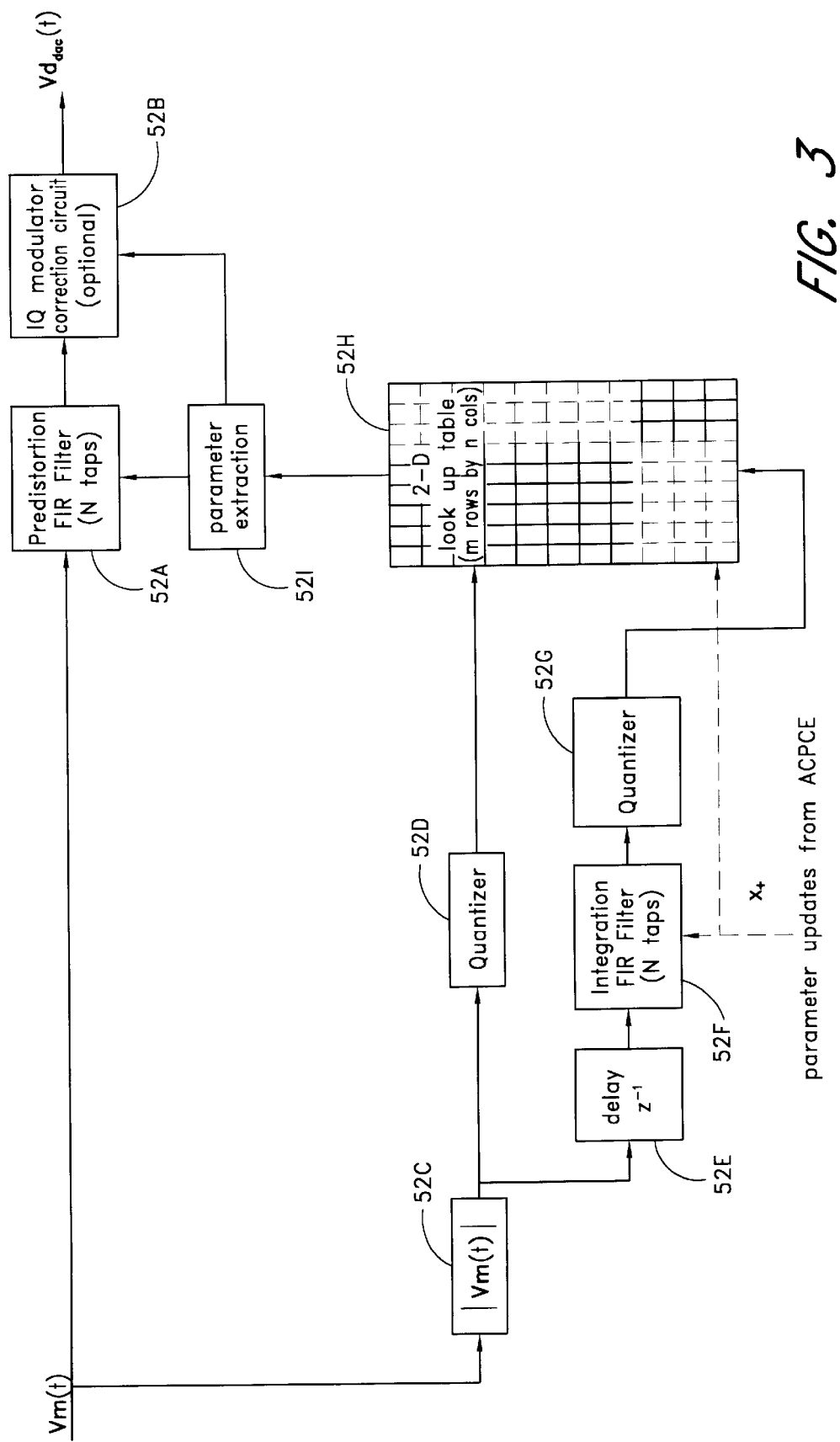
FIG. 3 illustrates details of the Digital Compensation Signal Processor (DCSP) of FIG. 1 according to one embodiment of the invention.

FIG. 3 illustrates the construction and operation of the digital wideband predistorter embedded within the DCSP 52 in one embodiment. The circuit may be constructed within an Application Specific Integrated Circuit (ASIC) and/or from an ensemble of complex logic blocks within a field programmable gate array or programmable logic technology such as Xilinx or Altera. Alternatively, the functionality of the circuit may be realized by developing software that executes on a digital signal processing chip such as the TMS320C54x or TMS320C60x series devices or a general purpose microprocessor such as the MC68008 or ARM7. Naturally, in these design scenarios the software may be resident in RAM, ROM, EEROM or Flash.

3.1.2. DCSP Functional Units and Operation

FIG. 3 illustrates the various functional units of the DCSP 52. The input signal Vm(t) is processed along two signal processing paths, both of which preferably operate in real time so that the output data rate matches the input data rate. The upper path includes a digital predistortion filter 52A, which is preferably a finite impulse response (FIR) filter, and an optional IQ modulator correction circuit 52B. The lower data path includes a rectification block 52C, a first quantizer 52D, a digital delay 52E, an integration filter 52F (preferably FIR), a second quantizer 52G, a multi-dimensional lookup table 52H (two dimensional in the embodiment illustrated in FIG. 3), and a parameter extraction block 52I.

An important aspect of the design is the use of a multi-dimensional look up table 52H to store correction coefficients, with each dimension indexed by a different respective characteristic of the input signal Vm(t). The table 52H is preferably indexed in one dimension (e.g., rows) by the instantaneous magnitude (amplitude) of the input signal Vm(t), and is simultaneously indexed in a second dimension (e.g., columns) by the integrated magnitude, filtered magnitude or time averaged magnitude (or a combination thereof) of the past input signal Vm(t). The table 52H is two-dimensional in the illustrated embodiment, but may have three or more dimensions (as discussed below) in other embodiments. Each element of the lookup table 52H stores a complete set of compensation parameters, including the FIR filter coefficients and the filter coefficients used by the modulator correction circuit 52B, when employed. Thus, in the illustrated embodiment, the table 52H holds m×n sets of filter coefficients. The table 52H may be implemented using any appropriate type of data structure, and will be referred to generally as the multidimensional "table" or "data structure." Preferably, the multidimensional table/data structure 52H is implemented within hardware (e.g., within an ASIC).

Although the use of a multi-dimensional data structure as set forth herein provides significant benefits, a one-dimensional data structure may be used, for example, in applications for which the input signal does not vary substantially in average power. Specifically, because the average power remains substantially constant, the sets of compensation parameters associated with other average power levels need not be generated or stored, permitting the elimination of one dimension of the table. In such embodiments, each element of the table again stores a complete set of compensation parameters, but the table is now indexed (accessed) based solely on an instantaneous attribute of the input signal, such as the signal's magnitude.

The upper path in FIG. 3 is responsible for computing the digital output signal $Vd_{dac}(t)$, which is a compensated and predistorted version of the input signal Vm(t), based on parameters read from the look-up table 52H along the lower path. The predistortion filter 52A predistorts the input signal to compensate for nonlinearities and amplitude variation along the entire analog upconversion and amplification chain 64. In practice, the imperfections in this chain include variations in group delay, propagation delay, gain and phase rotation. If analog IQ (quadrature) modulators are used, which permit direct complex baseband to RF conversion, additional imperfections due to IQ gain and phase imbalance (crosstalk) and local oscillator feedthrough and baseband DC offsets will invariably be observed; in these designs, the output of the predistortion filter 52A is therefore preferably processed by an IQ modulator correction circuit 52B to compensate for these effects. Examples of digital circuits that may be used to implement the predistortion filter 52A and the IQ modulator circuit 52B are illustrated in FIG. 4 and are discussed below.

The lower data path illustrated in FIG. 3 is responsible for selecting the set of correction coefficients to be loaded, on a sample-by-sample basis, into the predistortion filter 52A and if employed, the modulator correction circuit 52B. The correction parameters are read from the table by the parameter extraction block 52I at each sampling instant. An important feature of the design is that the coefficients used by these circuits 52A and 52B are permitted to be updated during the course of operation. That is, the parameter values are dynamic and subject to change. However, only one set of parameters is required at any time and they do not have to be changed on a sample by sample basis as can be required in predistortion linearizers.

To compute the lookup table addressing indices, the magnitude (or power) of the input signal Vm(t) is initially computed in block 52C. In other embodiments, the squared magnitude of the input signal may alternatively be used to index the table 52H. Equispaced indexing by magnitude is generally preferred, however, because the overall linearized amplifier performance is generally independent of the input signals amplitude density function and amplifier IBO. Using the signal's magnitude squared tends to favor focusing correctional performance only at the higher power operating points of the amplifier.

The magnitude signal generated by block 52C is processed along two paths in FIG. 3 to compute the row and column table indexes, respectively. In the illustrated embodiment, the row index is computed based on the instantaneous power of the input signal and the column index is based on a past power profile. Quantizers 52D and 52G are provided along each path to produce index values that correspond to the granularity of the table 52H. For example, if the input signal Vm(t) is represented by a sixteen bit number, the magnitude of the signal has $2^{15}$ i.e. 8 k different levels. Clearly an 8 k by 8 k dimensional table is unnecessary because the amplifier's nonlinearity can be accurately quantified by a significantly smaller number of sampling points. Thus, the quantizers 52D and 52G extract the most significant number of bits that correspond to the respective dimensions of the lookup table 52H. For example, if the instantaneous input dimension of the table 52H has 128 levels, the quantizer 52D will select the most significant 7 bits of the magnitude of Vm(t) to index the table.

As depicted in FIG. 3, the column index to the look-up table 52H is generated by delaying, filtering, and then quantizing the power signal. The purpose of the integration filter 52F is to compute the previous magnitude/power profile that has been applied to the amplifier. A high output value from the integration filter 52F indicates that the previous input profile has caused the amplifier to operate at high power for a period of time; in this situation, the nonlinearity exhibited by the amplifier 60 may be quite different from that exhibited when the amplifier is operated at a low power profile. The integration filter 52F is preferably a Finite Impulse Response (FIR) filter, although an Infinite Impulse Response (IIR) or other type of filer may alternatively be used. In one embodiment, the FIR integration filter uses taps that are spaced at non-uniform time intervals. In another embodiment, the FIR integration filter comprises a punctured FIR filter structure (i.e., uses FIR taps spaced at non-uniform time intervals that exceed the signal sampling period).

The overall size of the look up table 52H can vary from a single column vector to an extensive two dimensional array. In practice, a table consisting of 128–256 rows capturing the instantaneous magnitude drive level combined with 16–32 columns capturing the past integration power profile is sufficient for commercial operation. Savings in table size can be directly attributed to a lowering in linearization performance. Thus an economic versus performance engineering trade-off exists. Embodiments in which the table 52H has more than two dimensions are discussed in subsequent sections. The table may be implemented using a dual port RAM so that parameter sets can be read from and written to table locations concurrently. Example circuits and methods for updating the table 52H are described in Section 5.5.

As depicted by the vector $X_+$ in FIG. 3, the ACPCE 70 periodically updates the correction coefficients stored within the look-up table 52H, and updates the associated filter coefficients used by the integration filter 52F. As new correction parameters are generated by the ACPCE 70, an interpolation scheme is preferably used to smooth the transition between the current parameter sets (those stored in the table 52H) and the new parameter sets. (The term "correction parameters" refers generally to filter coefficients and any other dynamic values that are used in the real-time predistortion process.) Use of an interpolation scheme for this purpose reduces or eliminates undesirable power spectral responses that would be produced if the new parameters were merely switched into use. It is also possible to use interpolation between the correction parameters currently being used by the DCSP's predistortion circuits 52A, 52B and those being read from the table 52H for use.

Figure 4A:
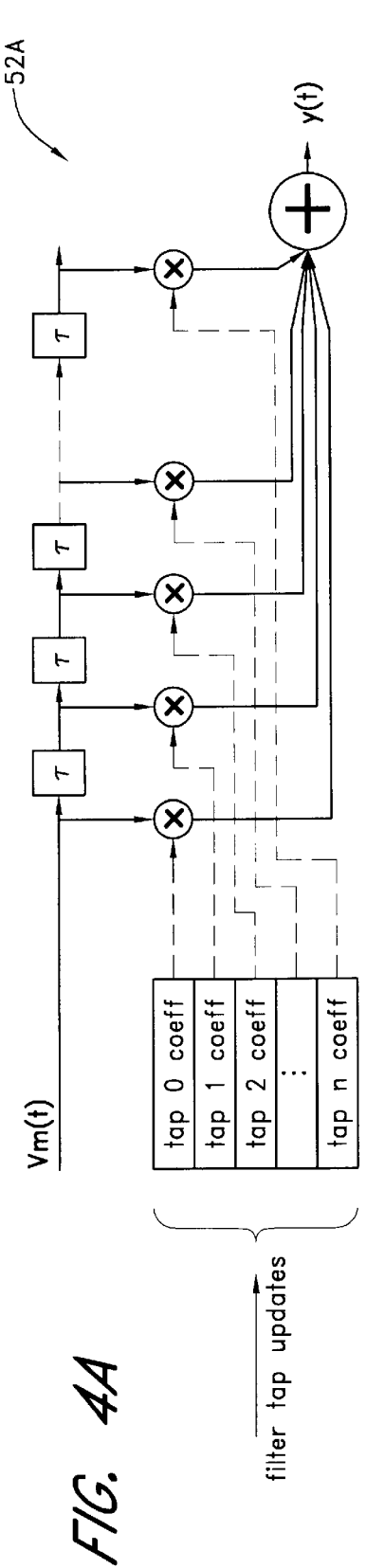
FIGS. 4A and 4B illustrate example digital circuits that may be used to implement the predistortion filter and IQ modulator correction circuit (FIG. 3) of the DCSP.
Figure 4B:
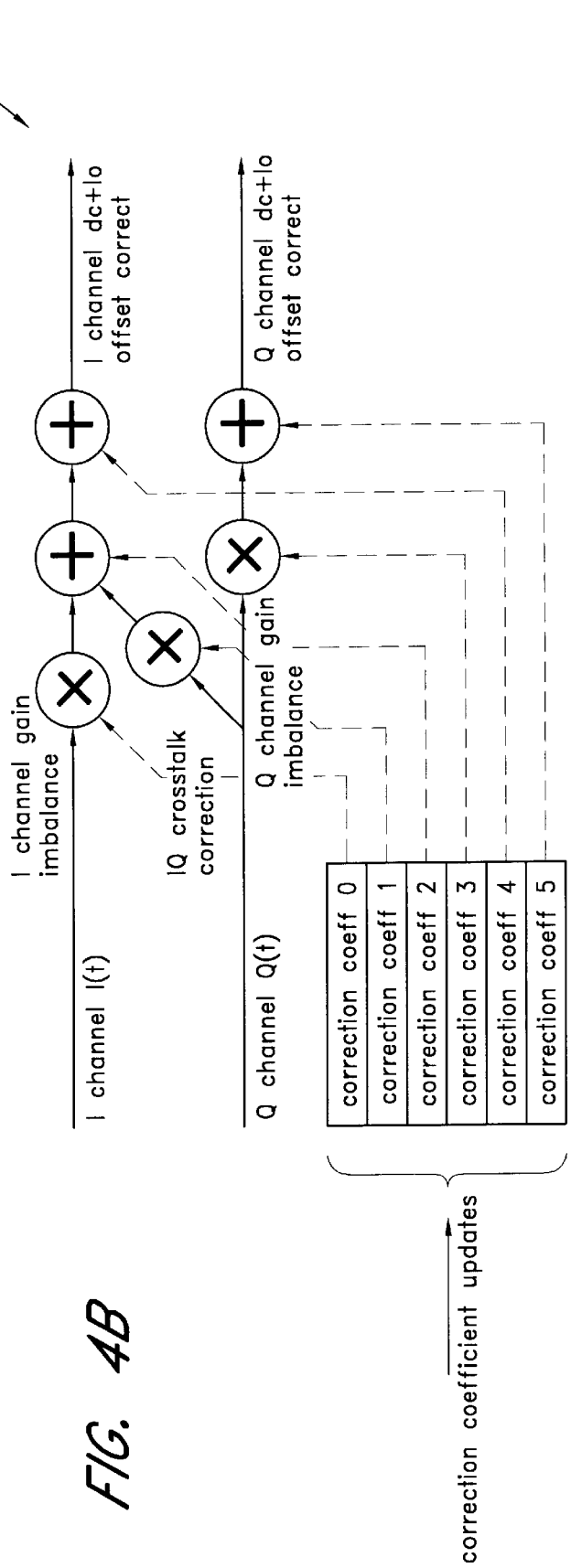

FIGS. 4A and 4B illustrate example digital circuits that may be used to implement the predistortion filter 52A and the IQ modulator correction circuit 52B. A variety of other well known circuits can alternatively be used. The number of taps N used for the predistortion filter 52A is a matter of design choice, but may, for example, be in the range of 5–11. Since a different set of FIR filter coefficients is used for each input sample of the input signal Vm(t) (indexed by power or amplitude), correction of the amplifier's wideband AM-AM and AM-PM frequency variant distortion characteristic is also achieved if the tap values are correctly computed. Since this is preferably a non-real-time computation process, the task of computing the FIR coefficient values is the responsibility of the ACPCE.

3.1.2.1. Integration Filter Construction

Figure 5:
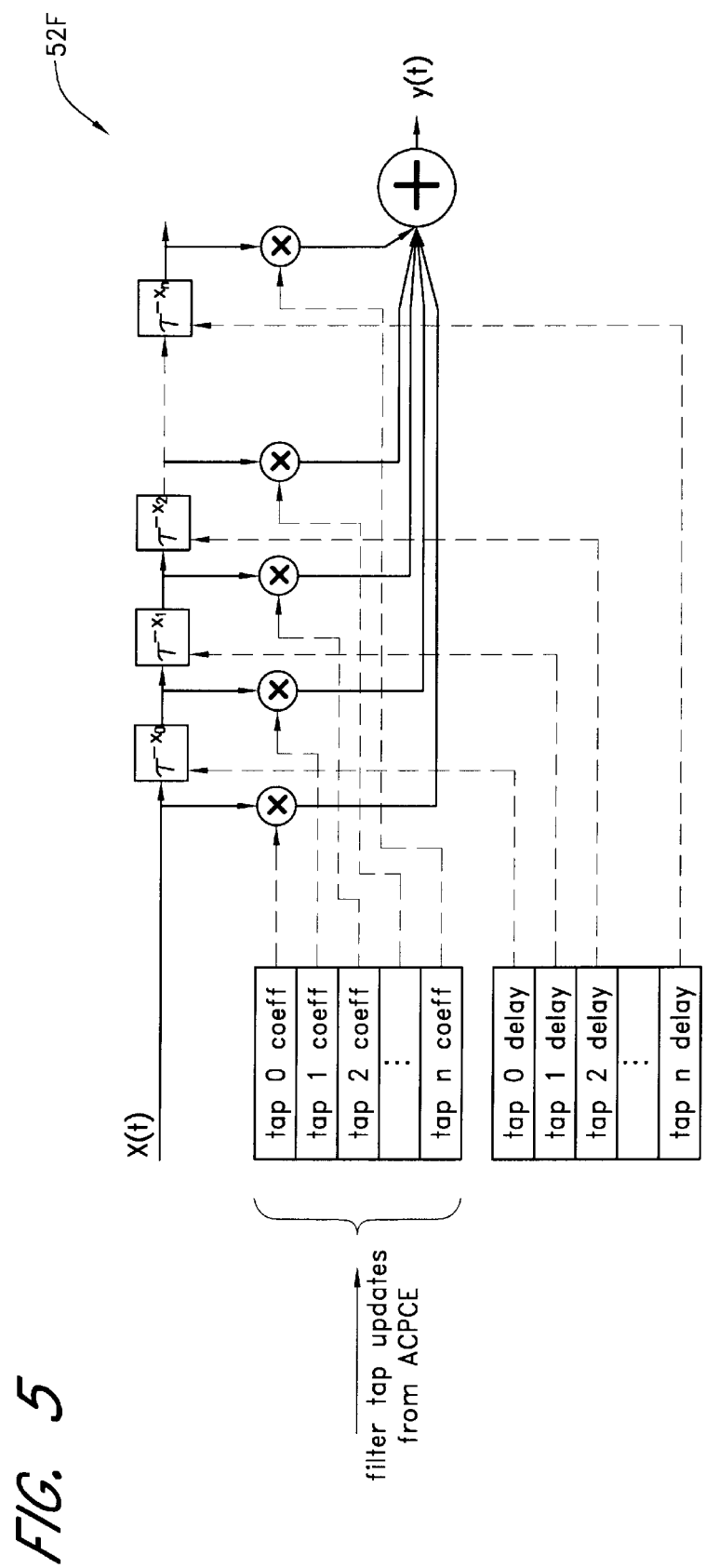
FIG. 5 illustrates an example digital circuit that may be used to implement the integration filter (FIG. 3) of the DCSP.

FIG. 5 illustrates the construction of the integration filter 52F in a preferred embodiment. An important feature of the integration filter 52F is that the FIR filter coefficients and input data sequences are preferably real values, i.e., not complex. Furthermore, the integration FIR filter is preferably constructed such that the FIR filter coefficients may be updated from the ACPCE 70, as indicated above. An additional feature of the design is that the integration filter's taps need not be spaced at single or uniform sample time instants, $\tau$. This allows the ACPCE 70 to completely define the taps and delays in the integration FIR filter to accurately capture the input power profile that defines the nonlinearity of the amplifier. This permits amplifiers with different power hysteresis/memory profiles to be employed. It is the preferably responsibility of the ACPCE 70 to determine the span and coefficients of the integration FIR filter.

To ensure that the integration filter 52H exhibits no effective delay with respect to the instantaneous stimulus, the integration filter's output is preferably computed only from the current and past stimulus to the amplifier (i.e., the filter is not symmetric). Furthermore, if the filter coefficients are correctly adjusted, the integration filter's output is directly proportional to the transistor die temperature. This permits the two-dimensional lookup table 52H to capture a one-to-one mapping of the nonlinearity of the amplifier as a function of instantaneous input amplitude and the current transistor die temperature (i.e., the past power profile of the amplifier). This simple first order integration filter is directly applicable to highly linear amplifier technologies such as LD-MOS. However, transistor dies utilizing silicon bi-polar technologies tend to exhibit significant nonlinear changes as a function of transistor temperature, and, as such, may not be accurately modeled by a linear or nonlinear function of the amplifier's past power profile.

Figure 6A:
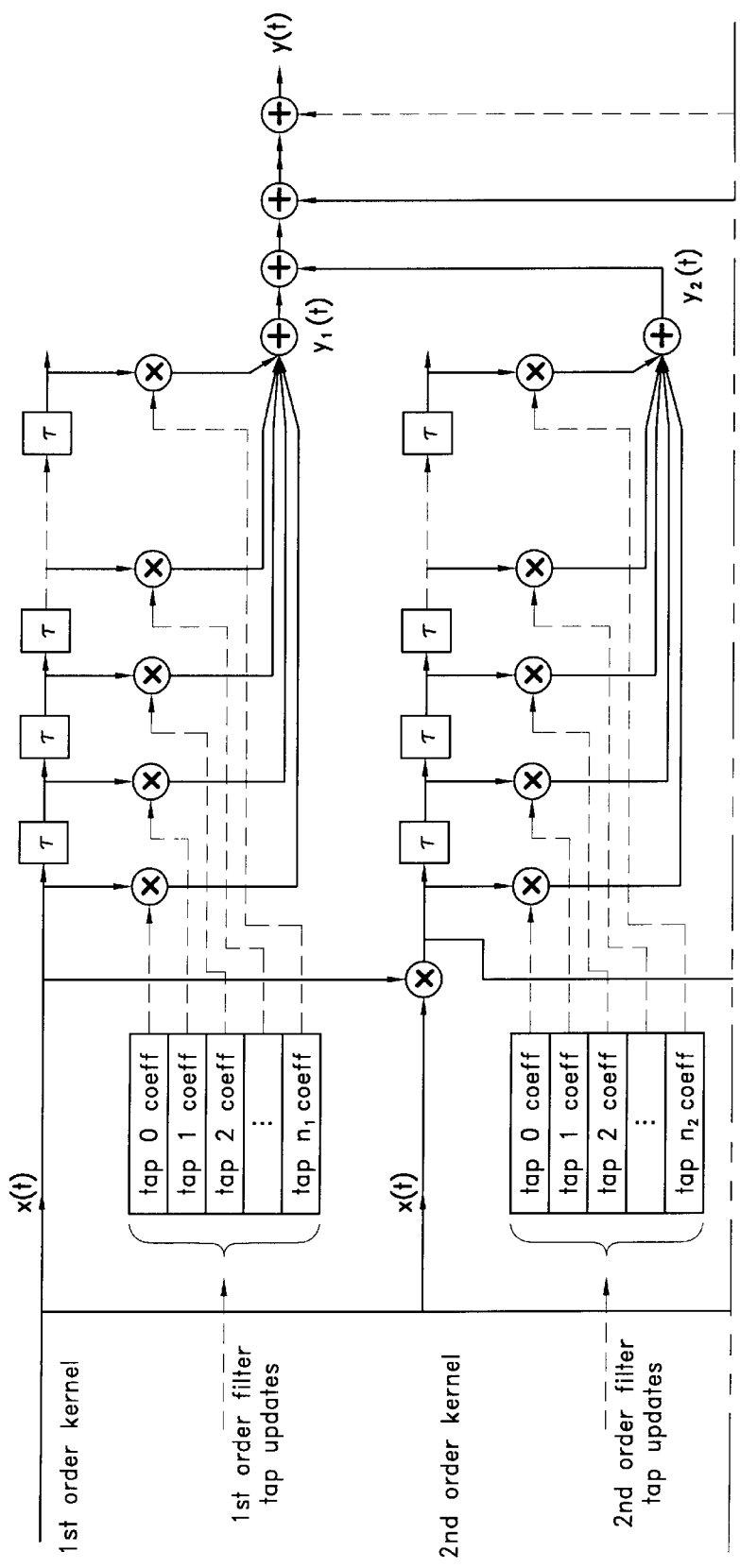
FIG. 6, which consists of FIGS. 6A and 6B, illustrates another circuit that may be used to implement the integration filter.
Figure 6B:
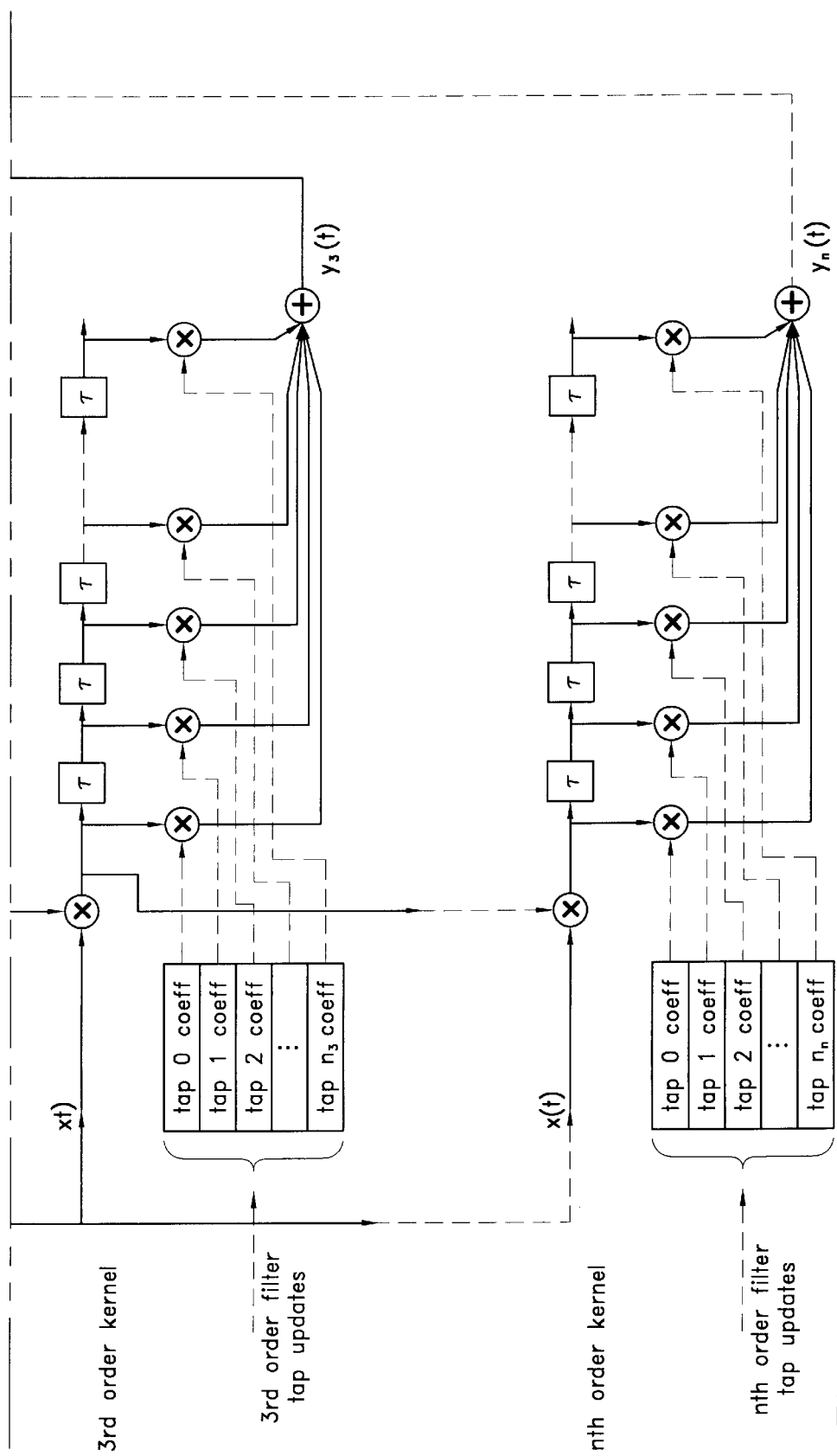

FIG. 6 illustrates a nonlinear integration filter kernel that may be used to overcome this problem when the wideband predistortion design is used with transistor technologies that exhibit nonlinear changes as a function of temperature. The nonlinear integration filter 52F is constructed from a bank of linear filters and a bank of multiplier stages. The input to each multiplier is the input signal magnitude and the output of the previous multiplier stage. This permits the set of signals, $x(t), x^2(t), x^3(t) \ldots x^n(t)$, to be computed from the original input signal $x(t)$. Each new signal is then fed to a linear FIR filter. As with the basic integration filter, the FIR filter tap coefficients and delay periods between taps are fully adjustable by the ACPCE. If each filter is regarded as an nth order kernel, the structure permits any linear or nonlinear function of the past input power profile to be computed. This permits accurate indexing into the two dimensional predistortion filter table 52H that corrects for the instantaneous distortion that is being generated by the nonlinear amplifier.

Equation 1 provides a mathematical definition of a non-linear integration filter structure which may be used. The filter may be envisioned as a series of Taylor series expansions. For each time lag the series expansion is independent, and so the structure can practically compute any nonlinear thermal characteristic function that may be exhibited by the transistor die. A goal of the ACPCE algorithms is to adjust the tap coefficients and delay between the taps such that the integration filter model of the amplifier provides an accurate representation of the amplifier's true characteristic.

$$y(t) =$$

Equation 1

$$c_{01} \cdot x(t) + c_{11} \cdot x(t-\tau) + c_{21} x(t-2\tau) + c_{31} \cdot x(t-3\tau) \cdot \ldots + \\ c_{m1} \cdot x(t-m\tau) + \ldots \\ c_{02} \cdot x^2(t) + c_{12} \cdot x^2(t-\tau) + c_{22} x^2(t-2\tau) + c_{32} \cdot x^2(t-3\tau) \cdot \ldots + \\ c_{m2} \cdot x^2(t-m\tau) + \ldots \\ c_{03} \cdot x^3(t) + c_{13} \cdot x^3(t-\tau) + c_{23} x^3(t-2\tau) + c_{33} \cdot x^3(t-3\tau) \cdot \ldots + \\ c_{m3} \cdot x^3(t-m\tau) + \ldots \\ : + \ldots \\ c_{0n} \cdot x^n(t) + c_{1n} \cdot x^n(t-\tau) + c_{2n} x^n(t-2\tau) + c_{3n} \cdot x^n(t-3\tau) \cdot \ldots + \\ c_{mn} \cdot x^n(t-m\tau) + \ldots$$

Although the integration filter's tap coefficients and tap delay values do not change on a sample by sample basis, they can be adjusted by the ACPCE if more accurate or appropriate values have been computed. One method for changing these values is to download a sequence of changes over a period of time such that a large step is broken into a sequence of smaller steps. As mentioned above, classic numerical interpolation techniques can be used to provide smooth transitions between steps so that disturbance errors are reduced.

3.1.2.2. Extended DCSP Compensation Architectures

High power nonlinear amplifiers typically exhibit second and third order characteristics that vary as a function of the applied input signal waveform. In particular, second and even order distortion mechanisms can, in sufficiently high power amplifiers, cause the bias voltages to become modulated with the input modulation signal information bearing envelope. Consequently, in these scenarios, an increase in DCSP compensation circuit complexity is desirable to combat the AM-AM and AM-PM that becomes dependent upon the envelope's instantaneous characteristic.

Figure 7:
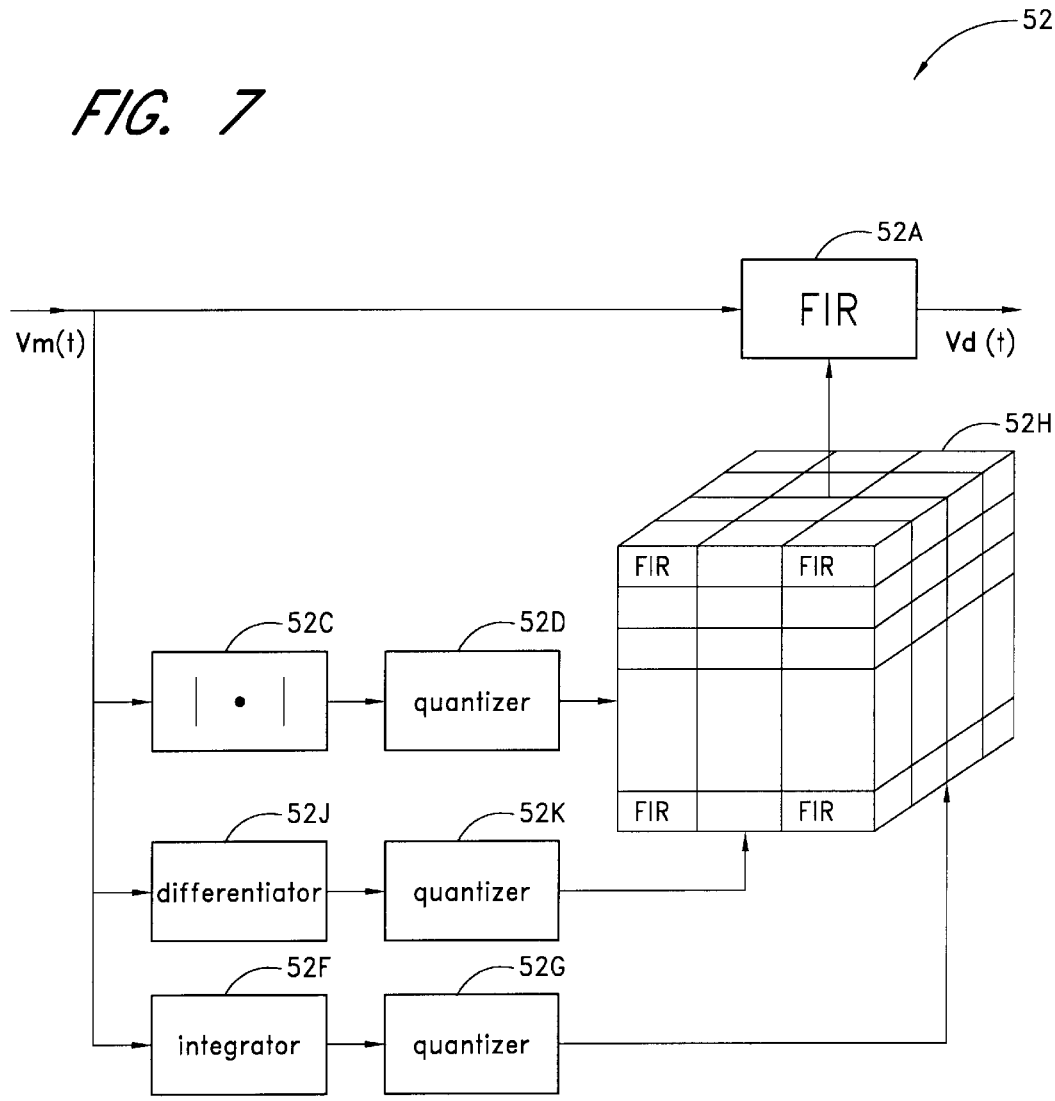
FIGS. 7 and 8 illustrate respective alternative designs for the DCSP of FIG. 1.

FIG. 7 illustrates the expansion of the DCSP circuit 52 to include a nonlinear dependency upon the rate of change of the complex modulation input Vm(t) in addition to the integration of the past envelope. The approach causes the DCSP data structure 52H to expand into an additional dimension. In this embodiment, the three dimensions are indexed by (1) the quantized magnitude of the input signal, (2) the quantized rate of change (preferably the first or second derivative) of the input signal, and (3) the quantized integration of the input signal. As each new additional independent cause of amplifier nonlinearity is identified, additional dimensions can be added to the table 52H. However, it is important to note that arbitrarily increasing the complexity of the DCSP compensation circuit could potentially give rise to fabrication difficulties and instability in the stored coefficients due to infrequent exercise.

Figure 8:
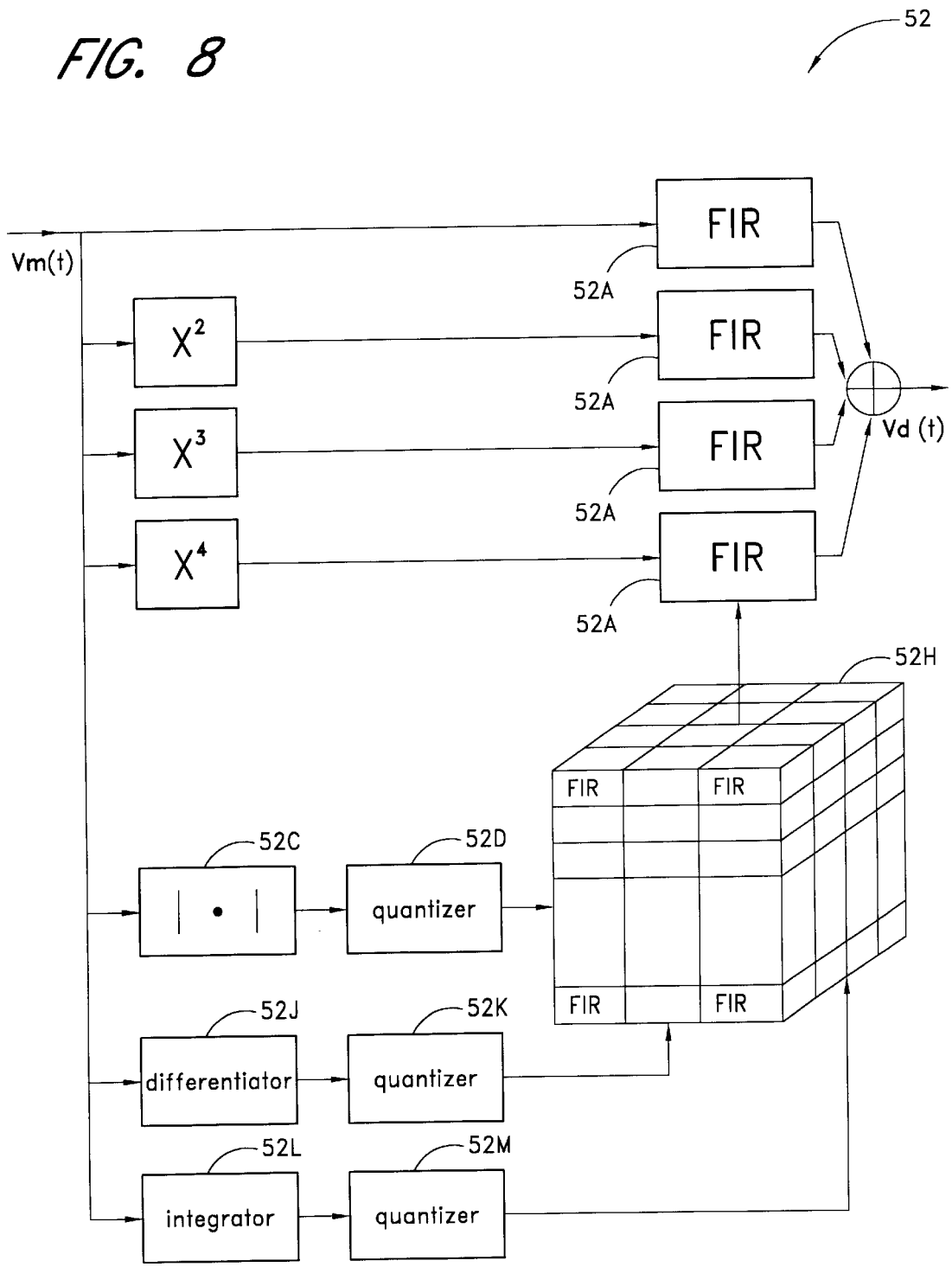

FIG. 8 illustrates an extension to the DCSP 52 that permits increased control over weak nonlinear effects by introducing a nonlinear FIR filter kernel into the forward data path. The compensation circuit in this embodiment includes multiple FIR filters 52A, one of which processes the wideband input signal, and the others of which each independently filter a respective higher order multiple or function of the wideband input signal. The outputs of the FIR filters are summed to generate the compensated signal. The multi-dimensional table 52H stores separate sets of filter coefficients for each of the FIR filters; this increases the storage requirement for each element of the table 52H since the number of FIR filter coefficients is significantly increased. However, stability is provided because of the regular exercising of each data structure element. Naturally, the design can be extended beyond fourth order nonlinearities, if required. Thus the DCSP structure provided in FIG. 8 permits compensation of a significant range of amplifier nonlinearity effects.

The architecture illustrated in FIG. 8 allows the DCSP to generate a full Volterra non-linear kernel in a piece-wise linear manner. That is, the DCSP can provide correction coefficients from the multi-dimensional data structure 52H that appropriately weight past, current and future samples of the input signal and higher order multiples of the input signal. As previously described, the weighting preferably occurs as a function of the input signal's instantaneous magnitude, rate of change (computed by the differentiator 52K) and integrated past power profile (computed by the integrator 52L). This structure permits any non-linear function with memory to be generated. The memory range that can be characterized by the time span of the FIR filters which is dictated by the number of taps and the inter-tap delay. Furthermore, the order of the non-linearity that can be modeled is also governed by the level of higher order/ multiples of the input waveform that are utilized. Typically three orders is sufficient. This DCSP architecture is highly versatile for it may be employed to accurately forward model or inverse model a power amplifier that exhibits a variety of strong and weak non-linear memory characteristics.

3.1.3. DCSP Theory of Operation

The theory of operation of the DCSP implementation shown in FIG. 3 will now be described in greater detail.

As discussed above, the amplification chain 64 may be described as a frequency and memory dependent AM-AM and AM-PM nonlinearity. This nonlinearity is corrected by the predistorter (DCSP) by assuming that an inverse non-linear characteristic can be constructed by a piecewise linear construction. In the illustrated embodiment, this is the precise functionality provided by the two dimensional lookup table 52H. One dimension is used to correct for the AM-AM and AM-PM nonlinearity that is observed as a function of the instantaneous stimulus. The second dimension captures the variation in the instantaneous AM-AM and AM-PM characteristic that occurs due to the thermal heating of the transistor die, which is directly proportional to the past power profile of the previous input.

If the amplifier assembly has been subjected to a high power operating point for a period of time, the transistor die will be significantly hotter and will hence exhibit a different AM-AM and AM-PM characteristic than if the input stimulus had caused the amplifier to operate at a lower power. A low die temperature will cause the nonlinearity exhibited by the amplifier to change, and as a consequence, a different set of correction coefficients will be used.

Since the two-dimensional look up table 52H is only indexed in the FIG. 3 embodiment by the magnitude of the instantaneous input voltage (or power) and a weighted average of the past input voltage magnitude (or power), the dimensional addressing has no ability to recognize frequency dependent information within the stimulating signal, nor the ability to intrinsically correct for the frequency dependent variation in the AM-AM and AM-PM characteristic of the amplifier. This is overcome by storing within each element of the look up table the tap coefficients and delays for a classical FIR filter 52A and, if appropriate, parameters for a modulator correction circuit 52B. The FIR filter 52A provides frequency dependent correction for the amplifier's frequency dependent characteristic; moreover, since the amplifier may be stimulated by a signal that contains multiple frequencies at any one instant, the FIR filter permits independent correction of each frequency component. This is a desirable and natural consequence of linear system theory. The FIR filter coefficients are computed by the ACPCE 70 such that, for any particular combination of instantaneous and past magnitude stimulus, the FIR filter 52A provides a perfect inverse impulse response to that exhibited by the combined modulator, IF-RF upconversion and amplifier assembly. That is, $$h_{system}(t) = h_{correction\,FIR}(t) \otimes \{h_{upconversion}(t) \otimes h_{amplifier}(t)\}$$
$$= \delta(t)$$

Equation 2

In practice, the length of the FIR filter 52A is constrained by a maximum delay that is permitted for the entire amplifier assembly. This impedes the correction performance of the FIR filter. Consequently, it is desirable that for a specified number of taps, the ACPCE computes a set of tap and delay values that minimize the residual error in Equation 2. The optimal approach is to ensure that the computed FIR filter coefficients provide a white residual error and a minimum mean square error solution. Utilization of an asymmetric FIR filter permits an increase in the number of taps and hence a lower error floor, provided the additional taps are used in conjunction with past data values (this does not increase filter delay). Alternatively, an IIR or Lattice filter may also be exploited.

3.2. Adaptive Control Processing and Compensation Estimator

The Adaptive Control Processing and Compensation Estimator (ACPCE) 70 implements the control algorithms for the wideband amplifier system 50. This block identifies and maintains the validity of the compensation parameters used by the DCSP 52 under all operating conditions. The control and data flow algorithms used within this block preferably encompass all operating conditions from initial calibration procedures through to on-line parameter update and estimation. The ACPCE also preferably ensures that the operation of the power amplifier 50 is free from spurious emissions when required to switch on and off and also when ramping on and off transmissions. Switch on involves powering up the amplifier 60 gradually by controlling the power supplies and/or bias. If the wideband predistorter is to be used at multiple operating frequencies and with various operating bandwidths, the ACPCE is also responsible for the management and storage of the appropriate correction parameters.

3.2.1. ACPCE Operation

Figure 9:
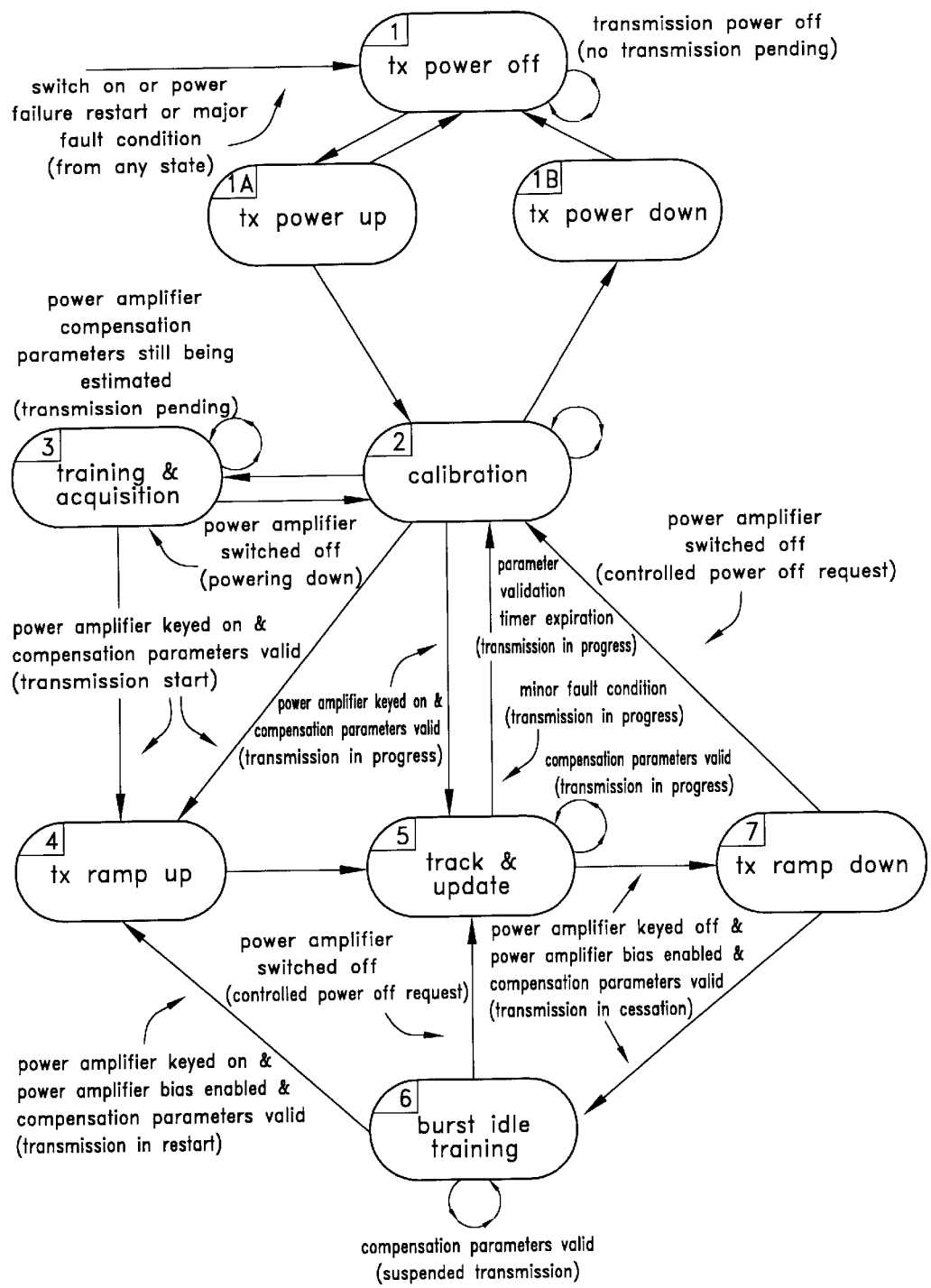
FIG. 9 illustrates an example state machine that may be implemented by the Adaptive Control Processing and Compensation Estimator (ACPCE) in FIG. 1 to control the operation of the amplifier system.

FIG. 9 is a state machine diagram that illustrates an example control process that may be implemented by the ACPCE to control the overall operation of the amplifier system. The states illustrated in FIG. 9 are described in detail in the following subsections. Many of the illustrated states use numerical and signal processing algorithms that operate upon stored sample data sequences of the digital input signal, Vm(t), and of the downconverted and digitized amplifier output, Vf(t). To ensure clarity, these data processing algorithms are detailed separately in a later section and are only referred to briefly within the state machine description.

It is assumed in the FIG. 9 embodiment that the power amplifier 50 has independent bias and keying control. This is typical for state of the art power amplifier designs. As will be recognized by those skilled in the art, the control process can easily be modified to support devices with a single transmit key only control.

3.2.1.1. State 1: Transmit Power Off

In the TX POWER OFF STATE(1) the ACPCE ensures that the amplifier 60 is turned off with the output stage bias removed and that no RF emission occurs. Previously computed compensation parameters are stored in memory for future utilization. (When the power is switched off completely the parameters are held in non-volatile memory.) The storage media is not important but should support fast access. Typical state of the art implementations may use RAM for storage while powered up and use FLASH ROM, EEPROM, hard disk or other magnetic storage media, etc. for non-volatile storage. The ACPCE applies the following control logic when in this state:

IF a bias on signal is applied to the power amplifier or if a control signal is enabled indicating that transmission is pending THEN the ACPCE shall exit the TX POWER OFF STATE(1) and enter the TX POWER UP STATE (1A)

ELSE the ACPCE shall remain in the TX POWER OFF STATE(1)

3.2.1.2. State 1A: Transmit Power Up

When in the TX POWER UP STATE(1A), the ACPCE ensures that no RF emission from the amplifier system 50 occurs while the bias and DC supply to the amplifier 60 is applied in a controlled ramp. The ACPCE applies the following control logic when in this state:

IF a bias on signal is applied to the power amplifier or if (a control signal is enabled indicating that transmission is pending and the bias has reached the normal point for operation)

THEN the ACPCE shall exit the TX POWER UP STATE (1A) and enter the calibration STATE(2)

ELSE IF a bias signal has been removed from the power amplifier or if a control signal is disabled or if the amplifier has been switched off THEN the ACPCE shall exit the TX POWER UP STATE (1A) and re-enter the TX POWER OFF STATE(1)

ELSE the ACPCE shall remain in the TX POWER UP STATE(1A)

3.2.1.3. State 1B: Transmit Power Down

In the TX POWER DOWN STATE(1B), the ACPCE removes the amplifier bias and DC supply voltage in a controlled manner so that no RF emission from the amplifier system occurs. The ACPCE applies the following control logic when in this state:

IF the bias and DC supply to the power amplifier has been fully removed

THEN the ACPCE shall exit the TX POWER DOWN STATE(1B) and enter the TX POWER OFF STATE (1)

ELSE the ACPCE shall remain in the TX POWER DOWN STATE(1B)

3.2.1.4. State 2: Calibration

In the calibration state the ACPCE determines whether the stored compensation parameters are still valid. This state captures a large breadth of conditions that may include initial provisioning of a new power amplifier. While in this state the ACPCE also determines if a transmission power ramp is required or whether the signal Vm(t) has a power ramp already embedded within its structure. This may also be a user programmable option. The ACPCE applies the following control logic when in this state:

IF it is determined that the existing compensation parameters are no longer accurate or valid OR IF the power amplifier is being provisioned with the first transmission test and the compensation values are set to inaccurate manufacturing default values OR IF compensation parameter value time stamps, if employed, have expired OR IF (the amplifier has been switched off AND the option of re-calibration on power down has been selected by the user)

THEN the ACPCE shall exit the CALIBRATION STATE (2) and enter the TRAINING AND ACQUISITION STATE(3)

ELSE IF the ACPCE determines that the compensation parameters are still valid, that is they are sufficiently accurate to ensure power spectral emission requirements are not exceeded AND the transmission request indicates that the transmission signal Vm(t) does not require a transmission ramp AND the power amplifier key up signal is enabled AND no fault conditions are present THEN the ACPCE shall exit the CALIBRATION STATE (2) and enter the TRACK AND UPDATE STATE(5)

ELSE IF the ACPCE determines that the compensation parameters are still valid, that is they are sufficiently accurate to ensure power spectral emission requirements are not exceeded AND the transmission request indicates that the transmission signal s(t) does require a transmission ramp AND no fault conditions are present THEN the ACPCE shall exit the CALIBRATION STATE (2) and enter the TX RAMP UP STATE(4)

ELSE IF the ACPCE determines that the power amplifier enable control signal has been disabled indicating that the pending transmission has been terminated OR IF (the amplifier has been switched off AND the option for re-calibration on power down has not been selected) OR IF (the amplifier has been switched off AND the option for re-calibration on power down has been selected AND a re-calibration has just been performed)

THEN the ACPCE shall exit the CALIBRATION STATE (2) and re-enter the POWER DOWN STATE(1B)

ELSE IF the ACPCE determines that a major fault condition has occurred

THEN the ACPCE shall report the fault condition to a power amplifier management entity and exit the CALIBRATION STATE(2) and re-enter the TX POWER DOWN STATE(1B)

ELSE IF the ACPCE shall remain in the CALIBRATION STATE(2)

3.2.1.5. State 3: Training and Acquisition

In the TRAINING AND ACQUISITION STATE(3) the ACPCE examines the stored compensation parameters and the performance of the predistortion process by monitoring the recovered power amplifier samples and identifying the characteristics of the upconversion and amplification chain 64. In addition, the ACPCE computes valid initial compensation parameters which are then uploaded via the parameter update vector $X_+(t)$ to the DCSP 52. A set of compensation parameters is considered valid for use if the resulting power spectral emission profile satisfies the regulatory spectral emissions mask and if the accuracy of the modulation/signal, $kVm_{rf}(t)$, is sufficient to meet a predefined system specification. While in this state the ACPCE may be required to evaluate the compensation parameters used for a single, multiple or a complete set of RF frequency channels that might fall within the amplifier's operating range. The exact evaluation requirements are dependent upon the operating scenario of the amplifier system. For example, during amplifier system commissioning, all channels may require compensation parameter estimation. Alternatively, during normal operation, compensation parameters will remain current by virtue of the operation of the TRACK AND UPDATE STATE(5), however, channels that are not exercised regularly may require exercise of the training and acquisition state.

The ACPCE identifies the imperfections of the analog upconversion and amplification chain using several algorithms. These algorithms use one or more training sequences that may be used in conjunction with various estimation techniques to compute the initial estimates of the compensation parameters. Each algorithm has unique attributes that provide different advantages in different commercial environments. These algorithms are described throughout Section 3.3.

The ACPCE applies the following control logic when in this state:

IF the power amplifier bias or power amplifier enable control signal has been disabled indicating that the pending transmission has been terminated OR IF (the amplifier has been switched off AND the option for re-calibration on power off has been selected AND the compensation parameter values are valid for all frequency channels that have been specified for calibration) OR IF (the amplifier has been switched off AND the option for re-calibration on power off has not been selected)

THEN the ACPCE shall exit the TRAINING AND ACQUISITION STATE(3) and re-enter the CALIBRATION STATE(2)

ELSE IF the ACPCE determines that a major fault condition has occurred

THEN the ACPCE shall report the fault condition to a power amplifier management entity and exit the TRAINING AND ACQUISITION STATE(3) and re-enter the CALIBRATION STATE(2)

ELSE IF the ACPCE determines that compensation parameter values are invalid for one or more frequency channels of operation that have been specified for calibration THEN the ACPCE shall execute the following compensation parameter estimation procedure STEP 1: stimulate the analog RF upconversion, amplification and power combining circuitry with one or more of the following test sequences a) transmit a narrowband bandlimited transmission sequence on the upconversion and amplifier chain.

b) transmit a wideband bandlimited transmission sequence on the upconversion and amplifier chain.

c) transmit a narrowband bandlimited white noise signal on the upconversion and amplifier chain.

d) transmit a wideband bandlimited white noise signal on the upconversion and amplifier chain.

e transmit a discrete or continuous frequency chirp sequence on the upconversion and amplifier chain.

f transmit a discrete or continuous polyphase sequence constructed on the upconversion and amplifier chain.

g transmit a sequence of random modulation sequence s(t) signal on the upconversion and amplifier chain. it is important to note that this stage may require the ACPCE to isolate the amplifier from an antenna and direct the generated RF energy to a dummy load to prevent undesirable power emission during training.

STEP 2: for each transmitted sequence the ACPCE shall collect a finite sequence of data samples of the transmitted signal Vm(t) (prior to digital signal compensation processing) while simultaneously collecting a concurrent finite sequence of data samples from the recovered downconverted power amplifier combining output circuit via the ADC circuits, Vf(t).

STEP 3: the ACPCE shall compute from the ensemble of received data samples estimates of all upconversion imperfections. This may be done by utilizing one or more of the following algorithms.
  a) correlation
  b) LMS system identification.
  c) RLS system identification.
  d) nonlinear Kalman filter system identification algorithms.
  e) any signal processing algorithm that is capable of system identification in non-linear signal processing, e.g. distortion analysis by wavelet multi signal resolution.

These algorithms are discussed in Section 3.3.

STEP 4: compute estimates of the signal compensation parameters that are required to counteract the imperfections identified in the previous step(3).

STEP 5: upload compensation parameters to the Digital Signal Compensation Processing block via the parameter state vector $X_+(t)$.

STEP 6: for each transmitted sequence the ACPCE shall continue to collect a finite sequence of data samples of the transmitted signal Vm(t) (prior to digital signal compensation processing) while simultaneously collecting a concurrent finite sequence of data samples from the recovered downconverted power amplifier combining output circuit via the ADC circuits, Vf(t).

STEP 7: determine if the error between the desired transmitted sequence Vm(t) and the observed sequence Vf(t) is below an acceptable level.

STEP 8: if the error is below an acceptable level then store update compensation parameters and proceed to step 9 else repeat steps 1–7.

STEP 9: if all channels have been calibrated then finish else repeat steps 1–8 for the next channel. The channels to be calibrated may be defined as a user option.

ELSE IF the ACPCE determines that compensation parameter values are valid for all frequency channels of operation that have been specified for calibration AND the power amplifier key enable has been set THEN the ACPCE shall exit the TRAINING AND ACQUISITION STATE(3) and enter the TX RAMP UP STATE(4)

ELSE the ACPCE shall remain in the TRAINING AND ACQUISITION STATE(3) and transmit one of the previous test sequences while simultaneously ensuring no RF emission radiates from the antenna. This may be performed by utilizing an antenna switch that is under direct control of the ACPCE, alternatively depending upon the particular application RF energy may be permitted to radiate from the antenna. OR the ACPCE will maintain dc bias and supply voltages to the amplifier but not provide an output sequence to stimulate the upconversion and amplifier. Thus ensuring no RF emission radiates from the antenna 3.2.1.6. State 4: Transmission Ramp Up In the TRANSMISSION RAMP UP STATE(4) the ACPCE provides a smooth bandlimited transition between the transmitted training sequence state and the start of the modulation signal. In practice, the ACPCE ensures that during the transition the gradients of the amplitude, phase and frequency trajectories are continuous and bandlimited. This is very similar to the ordinary problem of amplifier "clicks" known to those skilled in the art since the inception of telegraphic keying, morse code. However it is important to note that this effect is more pronounced in a wideband predistortion transmitter because the amplifier is running at full power and any step or disturbance in the modulation trajectory will cause distortion power spectra to be generated.

Thus the ACPCE provides a smooth transition between the normal transmission state and the burst training state. As mentioned earlier this is readily achieved by interpolation in the amplitude, phase and frequency domains.

The ACPCE applies the following control logic when in this state:

IF the amplifier has been switched off
THEN the ACPCE shall exit the TX RAMP UP STATE(4) and enter the TRACK AND UPDATE STATE(5)
ELSE IF the ACPCE determines that a major fault condition has occurred.
THEN the ACPCE shall report the fault condition to a power amplifier management entity and exit the TRANSMISSION RAMP UP STATE(4) and enter the TRACK AND UPDATE STATE(5)
ELSE IF the ACPCE determines that the power amplifier bias or power amplifier enable control signal is still enabled indicating that the transmission has started
THEN the ACPCE shall execute the power ramp algorithm and exit the TX RAMP UP STATE(4) and enter the TRACK AND UPDATE STATE(5)

3.2.1.7. State 7: Transmission Ramp Down

Power ramp down can suffer identical spectral emissions problems to those incurred when an amplifier is ramped up in power. The algorithm used for power ramp up is also directly applicable to the power ramp down scenario. The ACPCE applies the following control logic when in this state:

IF the ACPCE determines that the power amplifier has been switched off AND the amplifier is still being driven with the input signal
THEN the ACPCE shall execute the power ramp algorithm and exit the TRANSMISSION RAMP DOWN STATE(7) and enter the CALIBRATION STATE(2)
ELSE IF the ACPCE determines that a major fault condition has occurred
THEN the ACPCE shall report the fault condition to a power amplifier management entity and exit the TRANSMISSION RAMP DOWN STATE(7) and re-enter the CALIBRATION STATE(2)
ELSE IF the ACPCE determines that the power amplifier bias or power amplifier enable control signal has been disabled indicating that the transmission has finished
THEN the ACPCE shall execute the power ramp down algorithm and exit the TRANSMISSION RAMP DOWN STATE(7) and enter the BURST IDLE STATE(6)

3.2.1.8. State 5: Track and Update

State 5 represents the normal operational state of the amplifier system 50. When in this state, the ACPCE monitors the quality of the transmitted signal $kVm_r(t)$ and adjusts the compensation parameters to seek minimization of both modulation accuracy error and the power spectral density of the distortion products. Outdated coefficients are overwritten in memory with new and updated coefficients. New estimates of the compensation parameters may be directly uploaded to the DCSP, or if it is determined that the parameters have significantly changed, a sequence of parameter changes may be provided. This sequence preferably consists of a set of parameter values that are interpolated between the existing and new parameters, as discussed above.

The ACPCE uses several algorithms to continually improve the accuracy of the compensation parameters during on-line operation. These algorithms employ the random transmit signal Vm(t) as a training sequence that may be used in conjunction with various estimation techniques to compute the updated estimates of the compensation parameters. Each algorithm has unique attributes that provide different advantages in different commercial environments. These algorithms are described in Section 3.3.

The ACPCE applies the following control logic when in this state:

IF the ACPCE determines that a major fault condition has occurred

THEN the ACPCE shall report the fault condition to a power amplifier management entity and exit the track and update state(5) and enter the TX RAMP DOWN STATE(7)

ELSE IF the ACPCE determines that a minor fault condition has occurred.

THEN the ACPCE shall report the fault condition to a power amplifier management entity and exit the TRACK AND UPDATE STATE(5) and enter the CALIBRATION STATE(2)

ELSE IF the ACPCE determines that the amplifier has been switched off AND transmission is in progress OR IF (the amplifier has been switched off) AND (no transmission or a special training pattern is in progress)

THEN the ACPCE shall exit the TRACK AND UPDATE STATE(5) and enter the TX RAMP DOWN STATE(7)

ELSE IF the ACPCE determines that the transmission has been temporarily suspended for TDM burst mode procedures THEN the ACPCE shall exit the track AND UPDATE STATE(5) and enter the TRANSMIT RAMP DOWN STATE(7)

ELSE IF the ACPCE determines that compensation parameter values are valid for the frequency channel of operation and that normal transmission/operation is in progress THEN the ACPCE shall execute the following compensation parameter update and monitor procedure STEP 1: from the transmitted signal sequence, Vm(t), the ACPCE shall collect a finite sequence of data samples of the transmitted signal components Vm(t) (prior to digital signal compensation processing) while simultaneously collecting a concurrent finite sequence of data samples from the recovered downconverted power amplifier combining output circuit via the ADC circuits, Vf(t) (i.e., kVm(t)).

STEP 2: the ACPCE shall compute update estimates of the compensation parameters from the ensemble of received data samples. This may be done by utilizing one or more of the following algorithms:

a) LMS system adaptation and gradient update algorithms.

b) RLS system adaptation and gradient update algorithms.

c) nonlinear Kalman filter system adaptation and gradient update algorithms.

d) any signal processing algorithm that is capable of adaptation such that the updated compensation parameters are more accurate than the existing parameters.

These algorithms are discussed in Section 3.3.

STEP 3: upload compensation parameters to the Digital Signal Compensation Processing block via the parameter state vector $X_+(t)$.

STEP 4: for each transmitted sequence the ACPCE shall continue to collect a finite sequence of data samples of the transmitted signal components Vm(t) (prior to digital signal compensation processing) while simultaneously collecting a concurrent finite sequence of data samples from the recovered downconverted power amplifier combining output circuit via the ADC circuits, Vf(t) (i.e., kVm(t)).

STEP 5: determine if the error between the desired transmitted sequence Vm(t) and the observed sequence Vf(t) (i.e., kVm(t)) is below an acceptable level.

STEP 6: if the error is below an acceptable level then store update compensation parameters and proceed to step 8 else repeat steps 1–5.

STEP 7: finish. ELSE the ACPCE shall remain in the TRACK AND UPDATE STATE(5)

3.2.1.9. State 6: Burst Idle Training

The burst idle training state is preferably used only when the wideband amplifier system 50 is operated in a time division multiplexed mode. This mode may be used, for example, in applications in which the system provides bursts of RF modulated signal energy that are interspersed with short dormant periods in which RF energy is not generated. Typical commercial scenarios in which this mode of operation is used include the IS-54 TDMA digital cellular system, packet data networks such as the Federal Express system, PHS, and DECT PCS systems. Ordinarily, in these systems the power amplifiers remain biased but the transmit key is not enabled. This keeps the power amplifier transistor silicon dies thermally stable but still subject to significant change of operating point on resumption of full power transmission. This rapid change in the operating point of the transistor causes short term transient distortion products to be generated until the transistor is operating at full power and has re-acquired an operationally stable thermal state.

The ACPCE applies the following control logic when in this state:

IF the ACPCE determines that a major fault condition has occurred

THEN the ACPCE shall report the fault condition to a power amplifier management entity and exit the BURST IDLE TRAINING STATE(6) and enter the TRACK AND UPDATE STATE(5)

ELSE IF the ACPCE determines that the power amplifier enable control signal has been disabled indicating that the pending transmission has been terminated OR IF the amplifier has been switched off THEN the ACPCE shall exit the BURST IDLE TRAINING STATE(6) and re-enter the TRACK AND UPDATE STATE (5)

ELSE IF the ACPCE determines that compensation parameter values are valid for the frequency channel of operation and the power amplifier key enable has been set THEN the ACPCE shall exit the BURST IDLE TRAINING STATE(6) AND enter the TX RAMP UP STATE (4)

ELSE the ACPCE shall maintain the current bias and DC supply voltages to the amplifier and remain in the BURST IDLE TRAINING STATE(6)

3.3. ACPCE System Identification (SID) algorithms

Figure 10:
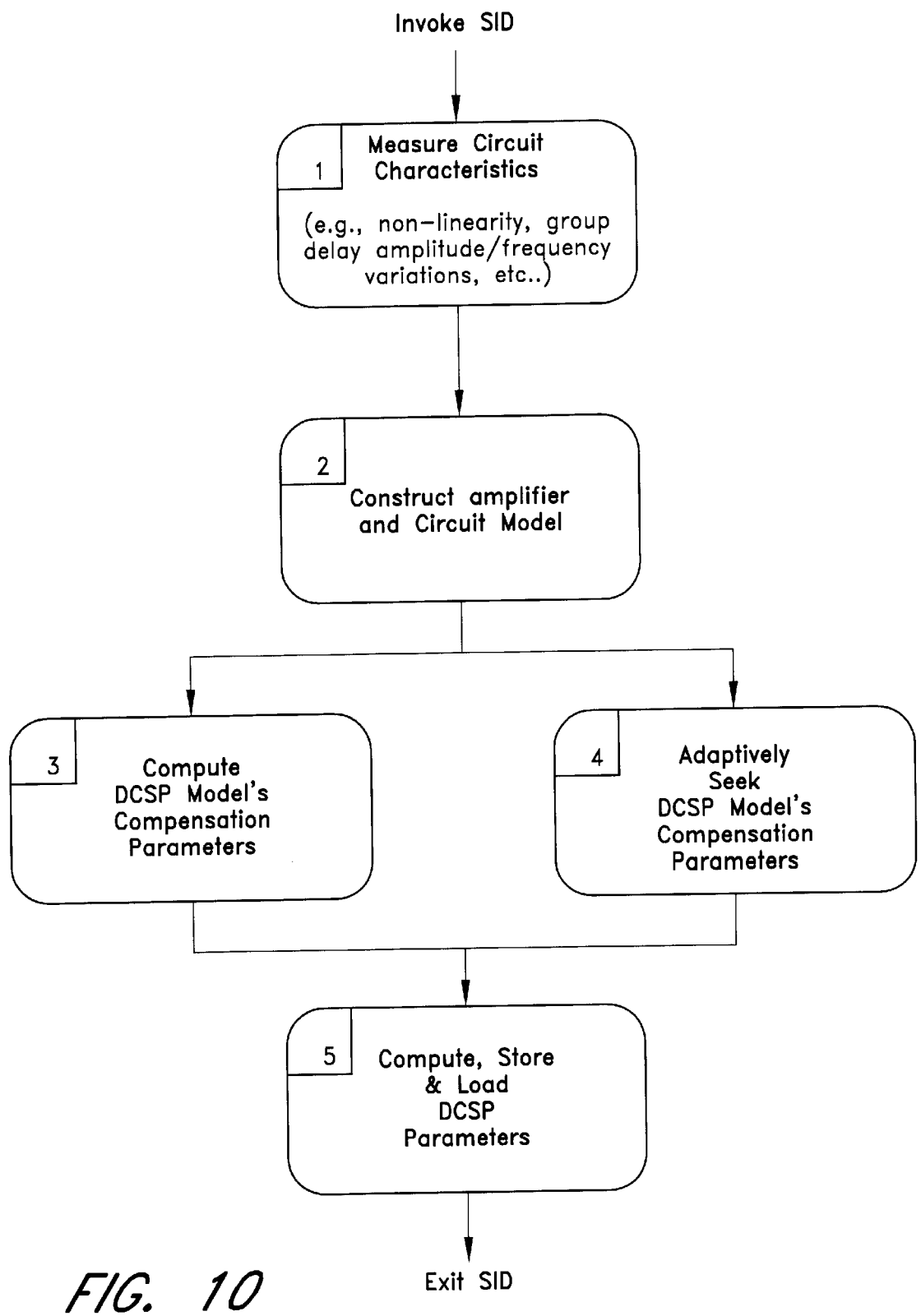
FIG. 10 illustrates a state diagram for the system identification (SID) phase of the ACPCE's operation.

As described above, the ACPCE 70 uses both system identification (SID) and system adaptation and tracking algorithms. FIG. 10 illustrates the state diagram for the system identification phase of the ACPCE's operation. Typically this phase will be used when the power amplifier is being tested during manufacture, installation commissioning and after extended periods of non-powered inactivity. The objective of the SID algorithms is to seek an initial set of correction parameters that may be downloaded to the DCSP such that the initial linearity and efficiency performance of the amplifier, albeit non-optimal, satisfies the power spectral emission and efficiency requirements of the operator. Enhanced performance is the responsibility of the system acquisition and tracking (SAT) algorithms which continually fine tune the performance of the amplifier system.

The following sections detail the operations and algorithms used within each state of the SID operation according to one embodiment.

3.3.1. State 1: Algorithms, Measure Circuit Characteristics

The feedback signal Vf(t) is a copy of the input signal, Vm(t), subjected to a variety of imperfections induced by the amplifier 60 and other external analog circuitry along the amplification chain 64 (FIG. 1). The SID algorithms initially stimulate the amplification chain 64 with a sequence of measurement signals that permit the following characteristics to be estimated: bulk loop gain, bulk phase rotation, bulk time delay, group delay variation, PA nonlinearity (AM-AM, AM-PM), PA nonlinearity frequency dependent variation, and PA time hysteresis/memory. Once these parameters have been estimated, the second state algorithms may construct a model of the amplification chain 64 from which correction parameters for the DCSP may be derived—either by adaptation or direct numerical computation.

A difficulty faced by the ACPCE SID algorithms is that it is extremely easy to damage or even destroy the amplifier 60 by over driving the power amplifier input. During SID it is assumed that, due to the variations in manufacturing, no accurate knowledge of the characteristics exhibited by the external analog circuitry is available. Consequently, steps are taken to ensure that damaging overdrive conditions do not occur. For example, the stimulation waveforms are selected or controlled such that the waveform peaks are significantly shorter than the time required to damage the amplifier transistor(s) in overdrive.

3.3.1.1. Power Ramping Algorithm and Measurement Signal Structure

3.3.1.1.1. Overview

To measure the characteristics of the amplification chain 64, the chain 64 is stimulated with a narrowband measurement signal. The measurement signal preferably exhibits the following characteristics: (1) the signal is bandlimited to approximately 1 MHz (or a sufficiently small fraction of the operating bandwidth such that the group delay is essentially constant) of the power amplifier's operating bandwidth, (2) the signal exhibits a high peak to average power ratio, (3) the signal's amplitude probability density function exhibits rare peak values and a dynamic range from zero amplitude to max signal power, and (4) the signal's level crossing probability density function indicates that extended durations of high power/peak power do not occur. Such a signal is typically characterized as a band and amplitude limited white noise signal whose amplitude PDF (probability density function) is characterized by a truncated Rayleigh function. This signal structure is particularly useful because it stimulates all input levels to the amplifier. Furthermore, the duration of an overload condition, should it occur, will be insignificant and not cause permanent damage to the amplifier 60.

Figure 11:
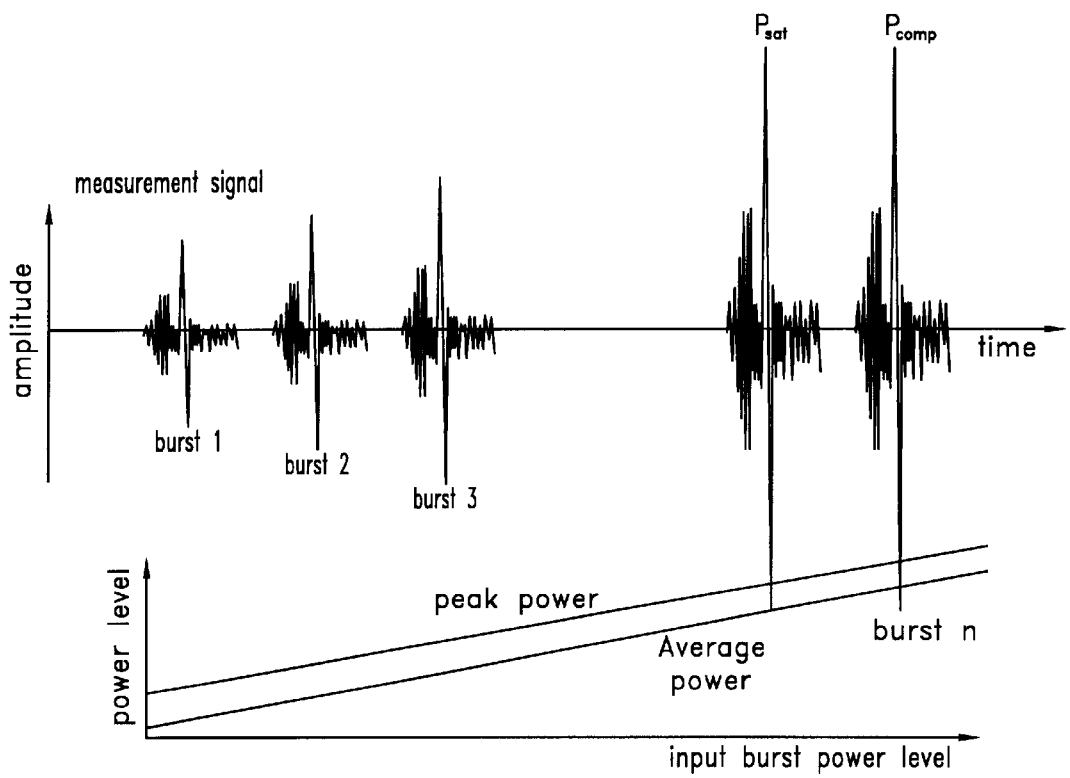
FIG. 11 illustrates power ramping of a measurement signal used for system identification.

The measurement signal is applied to the amplification chain 64 at a level such that the average and peak power levels are significantly lower than the maximum input power level of the amplifier. The input signal peak power level, Vm(t), and the peak power of the observed signal are recorded and the stimulation sequence repeated but at an increased power level. Typically 0.2 dB increases in power level are used when operating with a completely unknown amplifier. The measurement signal is repeatedly applied in increasing power levels until the maximum saturated output power level, $P_{sat}$ and 1 dB compression point, $P_{comp}$ are identified. This procedure is indicated in FIG. 11.

Figure 12:
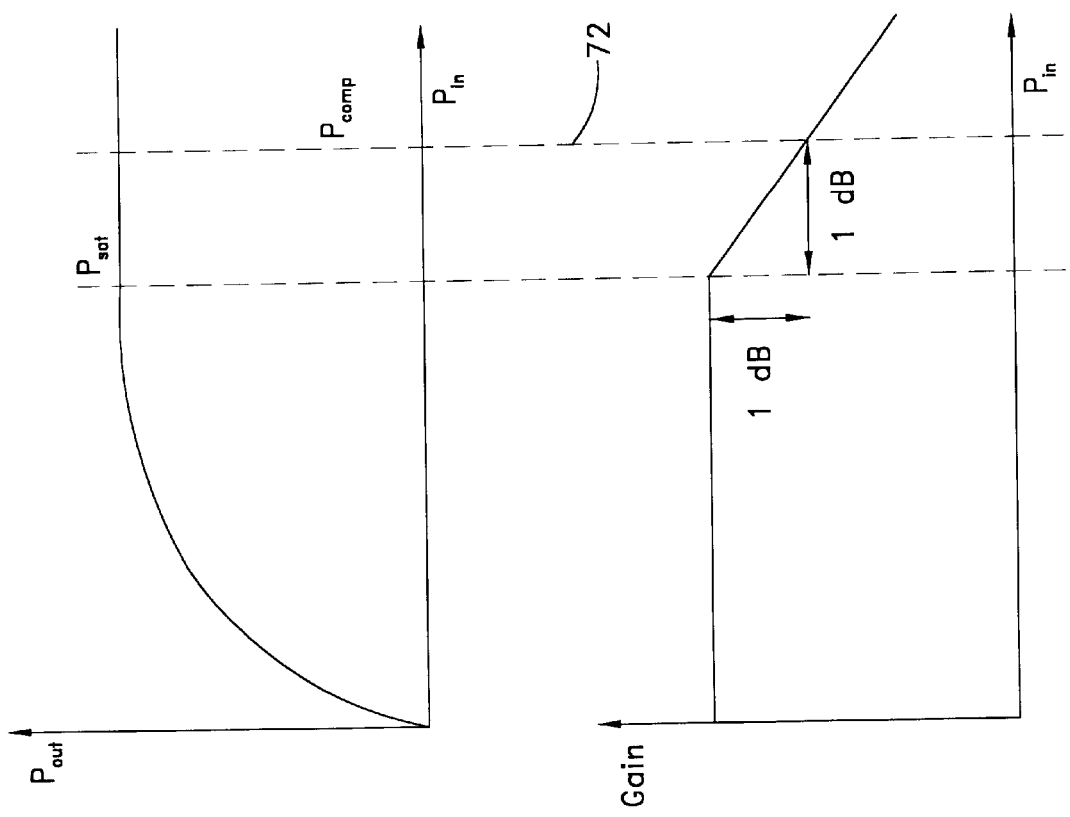
FIG. 12 illustrates gain and power response curves for typical RF amplifiers.

The saturated output power level and 1 dB compression point are identified by examining the relationship between the input power and output power and observed amplifier gain curves, the general form of which are shown in FIG. 12. The input power associated with the 1 dB compression point occurs at a point 72 at which the power amplifier's gain is 1 dB lower than the gain associated with the saturated output power. Furthermore, the 1 dB compression point is associated with a gradient of −45 degrees when gain vs. input power is plotted. These two key operating points are shown in FIG. 12 and are readily computed from the data collected during application of the measurement signal.

Once the maximum output power $P_{sat}$ and 1 dB compression point have been determined, the amplifier is stimulated with an extended sequence, or multiple bursts of the measurement signal, at a power level that exercises the amplifier from zero amplitude up to and including the 1 dB compression point. For each burst, the input measurement signal sequence Vm(t) and the observation signal sequence Vf(t) are recorded for post measurement processing. The center frequency of the measurement signal is shifted and the process repeated until the entire operational bandwidth of the amplifier 60 has been stimulated with the measurement signal. When this process is completed the entire operating bandwidth and input amplitude range of the amplifier is stimulated simultaneously by applying a wideband bandlimited white noise like signal to the amplification chain 64. As previously described, the input measurement signal and observed feedback signal are recorded for post processing. The construction of the wideband measurement signal is identical to the narrowband measurement signal in all respects except for its occupied bandwidth.

3.3.1.1.2. Algorithm Flow Chart of Measurement Process

Figure 13:
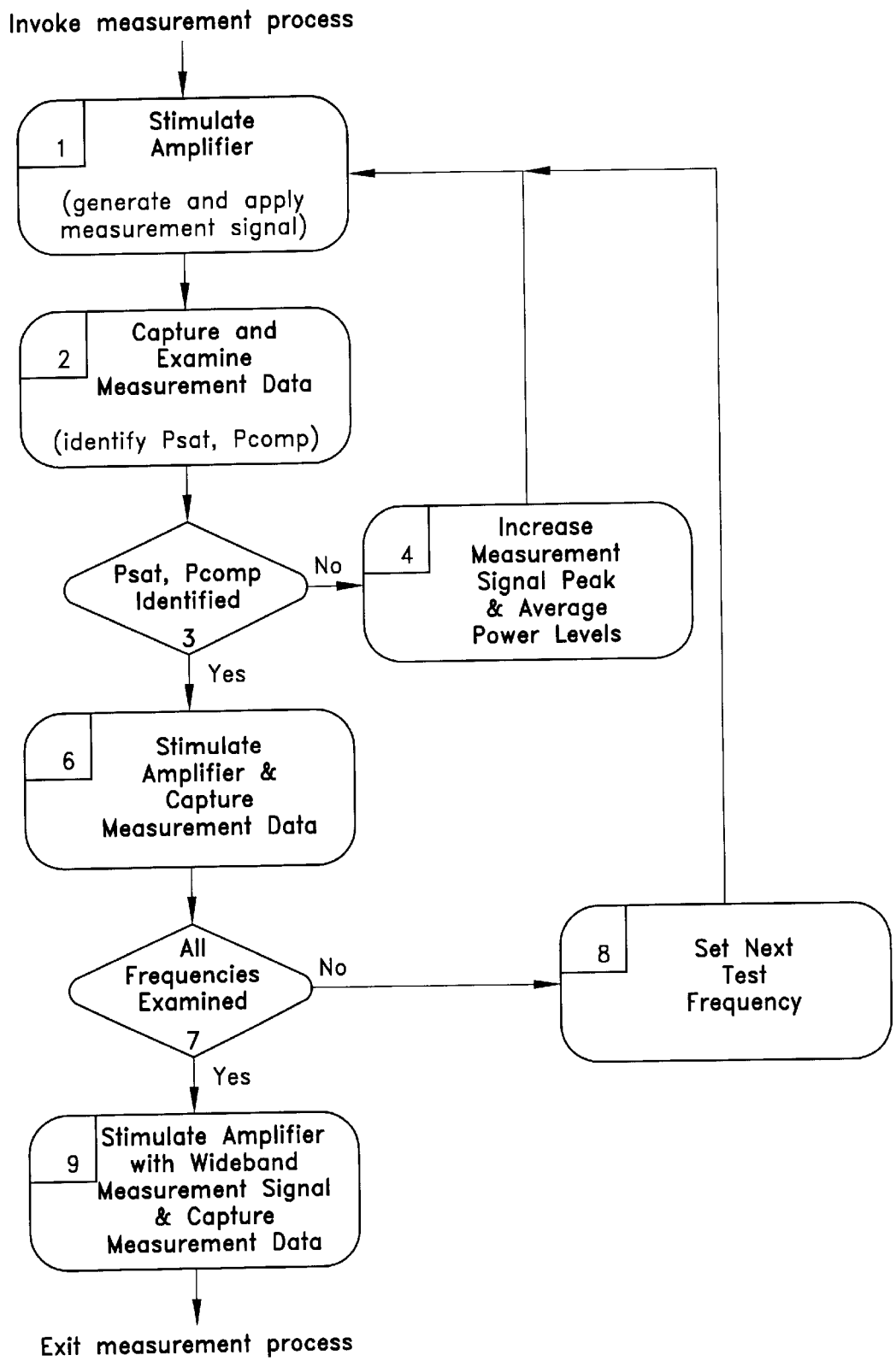
FIG. 13 illustrates a process for implementing state 1 (measurement of circuit characteristics) in FIG. 10.

The previous section provided an overview of the measurement process. FIG. 13 illustrates a preferred embodiment of the process. The illustrated state diagram provides the internal processes of the first state illustrated in FIG. 10.

3.3.2. State 2: Algorithms, Construct Amplifier and Circuit Model

3.3.2.1. Overview

Figure 14:
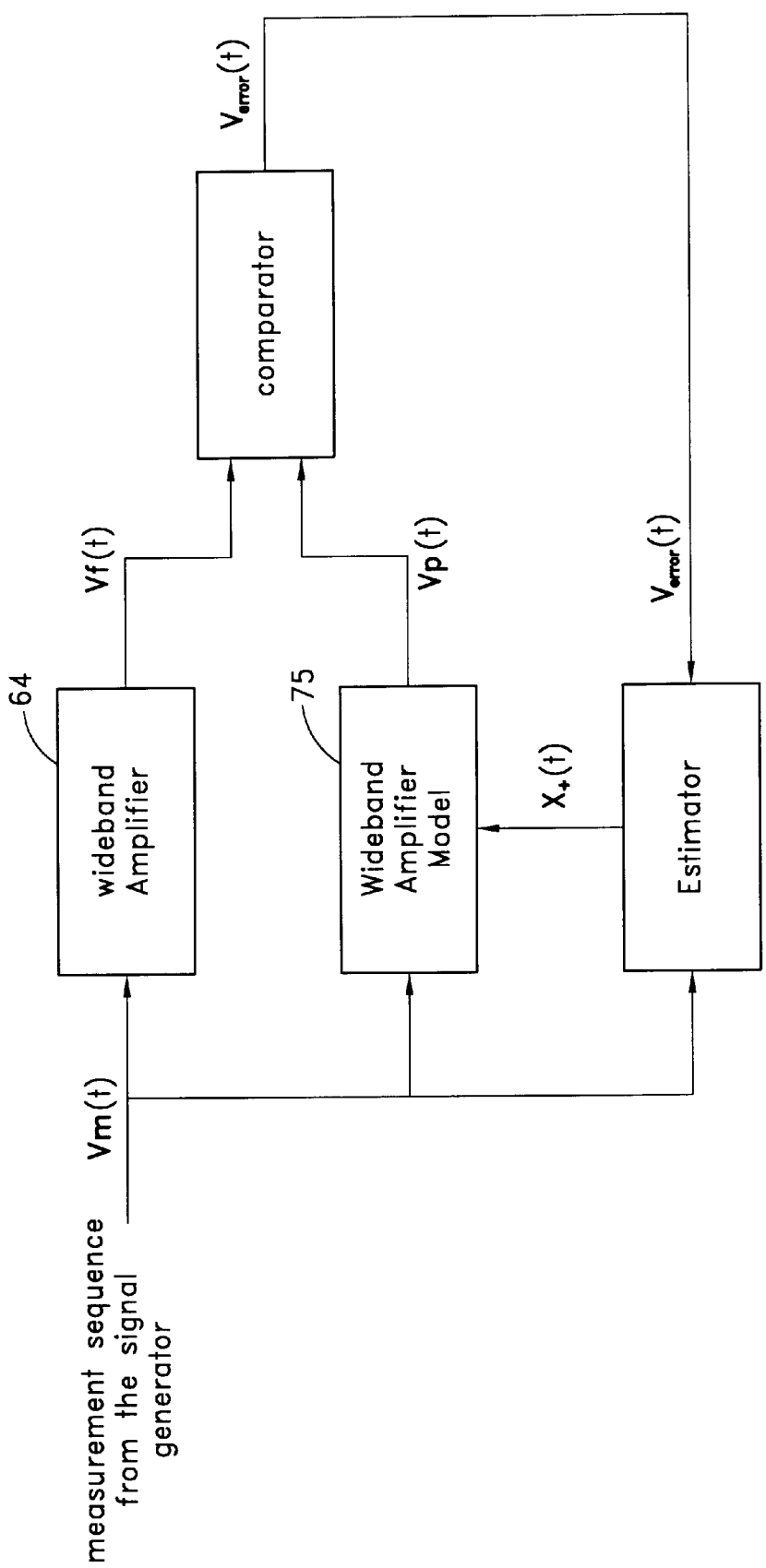
FIG. 14 summarizes the initial identification problem solved by the ACPCE's system identification algorithms.

FIG. 14 summarizes the initial identification problem that is solved by the ACPCE system identification algorithms. As described in Section 3.3.1, during SID, the ACPCE stimulates the wideband amplifier with a measurement waveform Vm(t) and records the associated output/observed signal Vf(t). However, observation of particular elements within the amplification chain 64 is not permitted. Consequently, the ACPCE uses a parallel numerical model that mirrors the expected processes of the real analog wideband amplifier. To identify the initial values of the compensation parameters, the coefficients of the numerical model are adjusted so that the predicted waveform, Vp(t), is identical to the real observed signal, Vf(t). Once the model of the wideband amplifier has been successfully adjusted, the compensation parameters may be directly computed or derived by numerical or adaptive computation to ensure that the compensation network introduces equal and opposite imperfections to the upconversion/amplification process.

Identification of a system model is a well defined control problem that has many solutions in the robotics and control field. LMS, RLS, and Kalman type algorithms are preferably used for this purpose, including extended LMS, momentum LMS, extended RLS, extended Kalman, and non-linear Kalman algorithms.

FIGS. 15–18 illustrate power amplifier models 75 that exhibit progressively higher orders of complexity. The modeling process of the power amplifier 64 proceeds by estimating and adjusting the parameters of the least complex model until an error floor between the predicted and observed signals is reached. If the error floor is not low enough for the purposes of SID in a particular application area, then the model parameters are exported to the next level of model complexity. The process is then repeated, that is the increased complexity model parameters are adjusted until a new and lower error floor is determined. The following sections describe power amplifier models and associated algorithms that may be used to adjust the model parameters.

3.3.2.2. Power Amplifier Models

The structure of the models 75 shown in FIGS. 15-18 is very similar to the construction of the DCSP correction circuits. This similarity exists because the structures permit any degree of nonlinearity to be represented. In practice, the coefficients of the FIR filters stored in the two multi-dimensional data structures 78, 52H differ quite markedly because the coefficients of the DCSP are computed to counteract the deleterious effects of the power amplifier 64.

Figure 15:
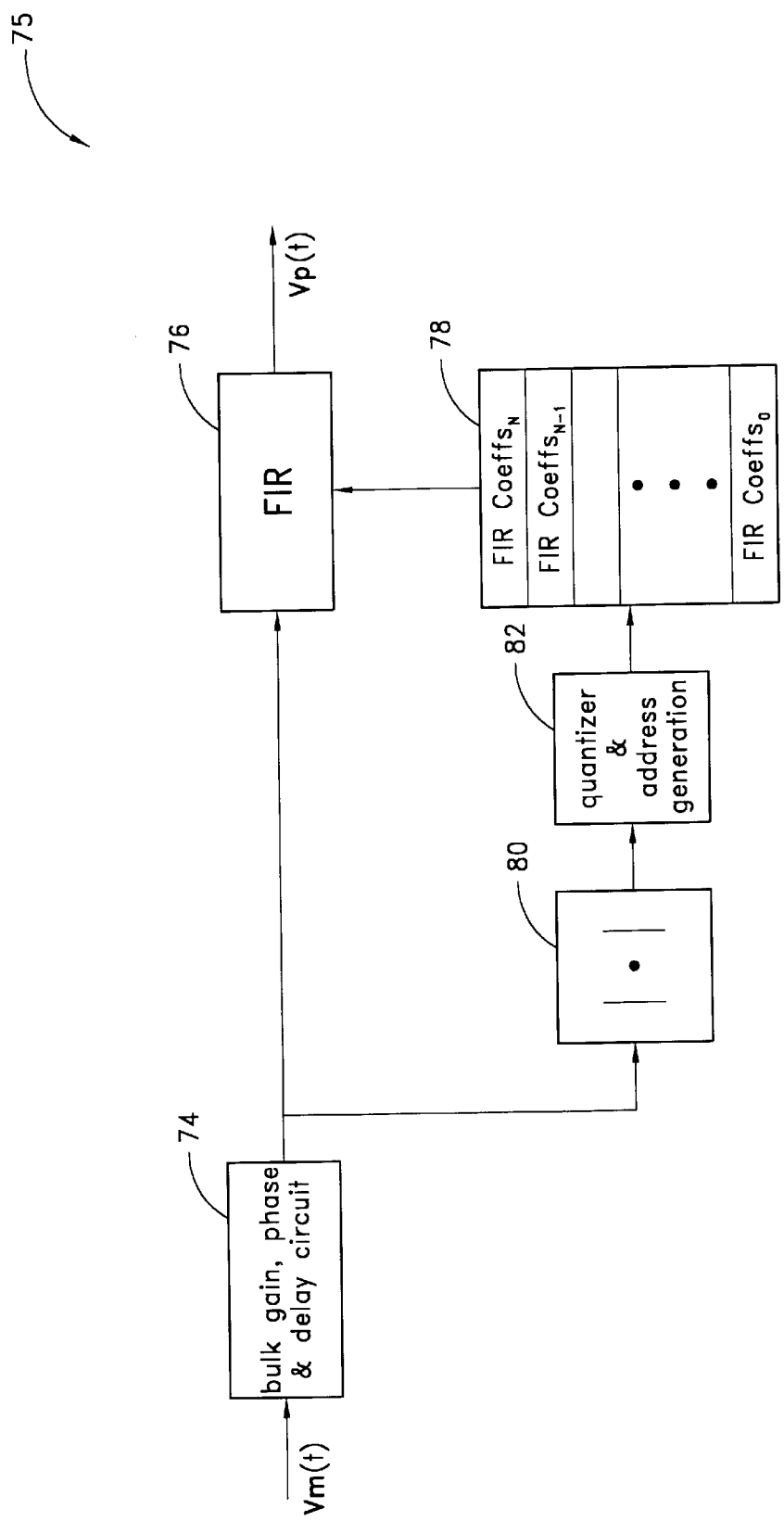
FIGS. 15–18 illustrate power amplifier models of progressively increasing orders of complexity used in state 2 of FIG. 10.

3.3.2.2.1. First Order Extended Single Kernel Nonlinear Power Amplifier Model The first order extended single kernel model 75 illustrated in FIG. 15 represents the simplest wideband model of the power amplifier 64. The model consists of a bulk delay, gain and phase stage 74 followed by an FIR filter 76 which incorporates the frequency domain variations of these parameters. Since the amplifier exhibits nonlinearity which causes all of these parameters to vary as a function of the input amplitude, the coefficients of the FIR filter 76 are stored in a data structure 78 that is indexed by input power or signal amplitude. This permits a piecewise linear approximation of the AM-AM and AM-PM characteristic exhibited by the amplifier. Naturally, frequency domain variations of this characteristic are represented within the FIR filter coefficients. A particular set of parameters within the data structure is selected by quantizing the input signal Vm(t) into a specific set of discrete levels.

Since the amplifier model 75 is only used during system identification and not during periods of operation, the computational burden upon the ACPCE is not particularly important and so the number of FIR filter coefficients can be expanded to a "quasi" impractical level (for real time operation) to provide maximum accuracy in generating the predicted power amplifier Vp(t) and hence minimizing the error floor between Vf(t) and Vm(t).

3.3.2.2.2. Second Order Extended Single Kernel Nonlinear Power Amplifier Model The simple wideband power amplifier model described in the previous section is appropriate for low power devices which exhibit very weak nonlinearities in which memory effects are minor. As the power rating of an amplifier increases and exceeds 1 watt RF power capability, several second order effects become sufficiently pronounced that the error floor associated with the previous model is generally too high to be used. That is, the FIG. 15 model does not represent the behavioral characteristics of the amplification chain 64 with sufficient accuracy that DCSP compensation parameters can be reliably computed.

Figure 16:
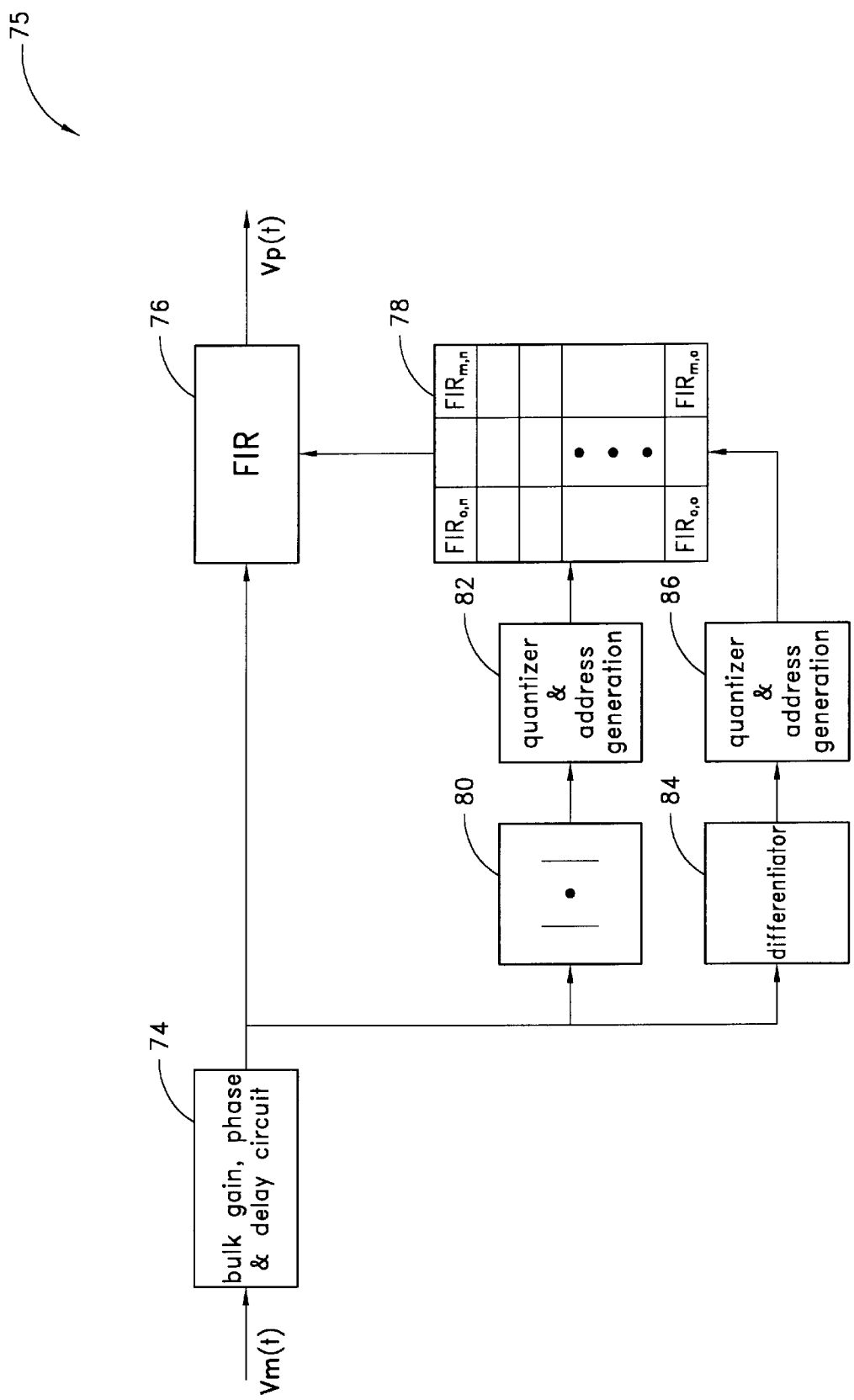

FIG. 16 illustrates the next level of wideband power amplifier model complexity. The model 75 introduces an additional dimension to the construction of the amplifier model's core data structure. This permits the FIR filter coefficients to be stored and retrieved as a function of two independent processes. However, it is important to note that while the data structure 78 may be accessed by multiple independent indices, the stored FIR filter coefficients represent a unique nonlinearity characteristic for that particular combination of input stimuli. That is, the behavior of the amplifier 64 cannot be accurately described as a set of independent correction coefficients for each independent input stimuli. As previously discussed, the data structure is indexed by signal amplitude or power, while the additional, new dimension is indexed by the rate of change of the signal's complex envelope.

The differential of the modulation envelope is an important process to consider when extending the range of independent variables over which the power amplifier's nonlinearity is modeled. Laboratory tests have shown that although the envelope PDF of two particular waveforms may be identical, the nonlinearity exhibited by a particular amplifier may vary significantly if the level crossing rates differ, i.e. one signal exhibits a different bandwidth. The key process is that envelope rectification within the power amplifier may occur, producing a DC signal level that modulates the transistor bias voltages and hence alters, in a time variant fashion, the nonlinearity exhibited by the amplifier. The model illustrated in FIG. 16 provides a mechanism by which this process can be isolated from the bulk AM-AM and AM-PM characteristic of the amplifier. In an analogous manner to the previous model, the signal envelope's rate of change is computed by the differentiator 84 and quantized to form an address to the two dimensional data structure 78. Each element of the data structure 78 contains a set of FIR filter coefficients. Since this effect is typically significantly smaller than the main AM-AM and AM-PM characteristic, the address span in the differential axis may be significantly smaller than the signal amplitude address span.

Figure 17:
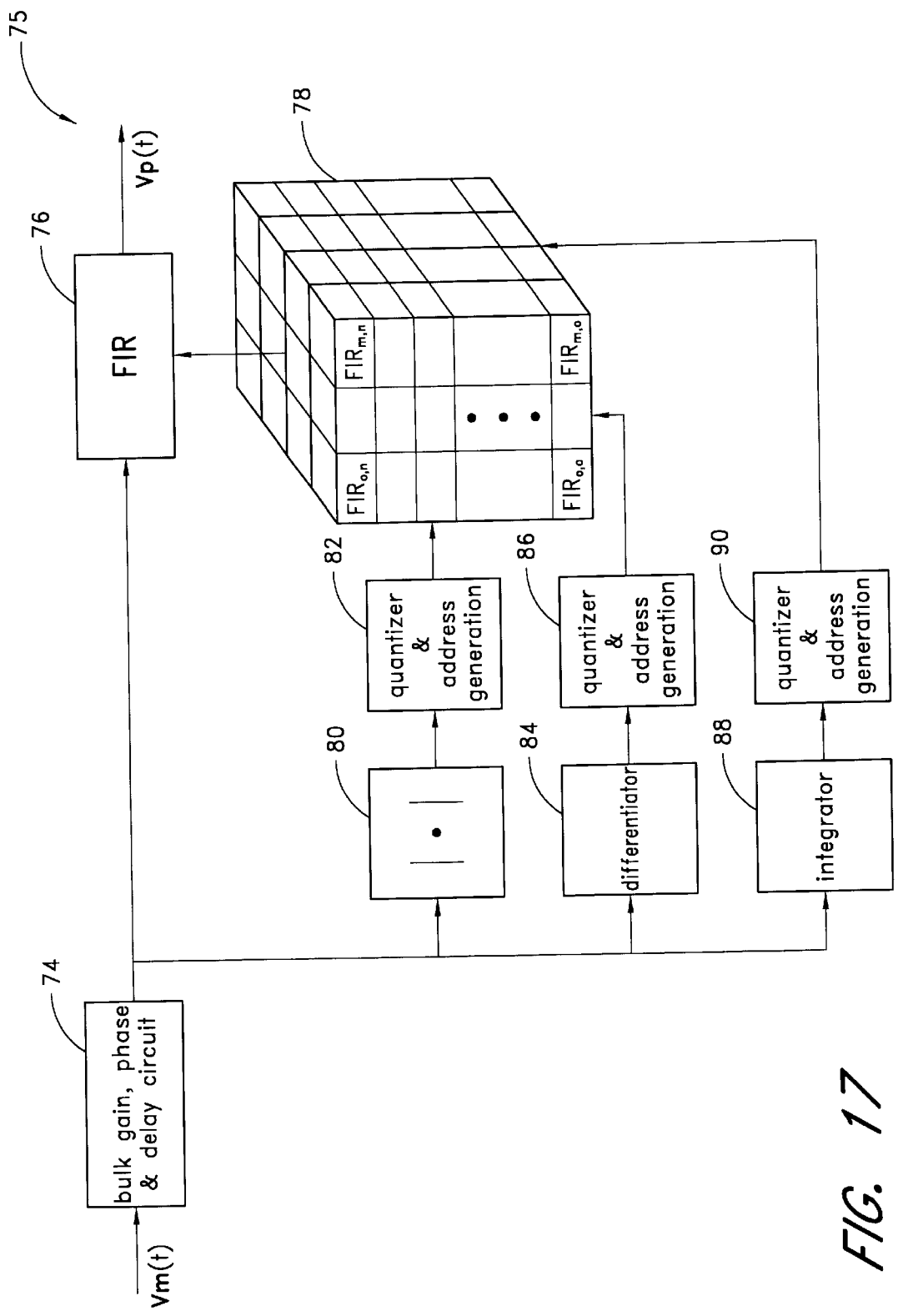

3.3.2.2.3. Third Order Extended Single Kernel Nonlinear Power Amplifier Model As the operating power level increases beyond 10 watts of RF power, the power amplifier's transistor junction die temperature fluctuates significantly as a function of the modulation envelope. Since the intrinsic AM-AM and AM-PM characteristic of the amplifier 64 is defined by the semiconductor physics of the transistor junction die and the die temperature, it is to be expected that variations in the nonlinear characteristic of the amplifier will be observed. As depicted in FIG. 17, these variations may be predicted by introducing a third independent degree of freedom into the model 75 of the amplifier 64, addressed as a function of the integrated signal amplitude or past average power generated by the amplifier. The integrated signal amplitude is directly proportional to the current drawn by the transistor junction die which is consequently proportional to the die operating temperature. An alternative implementation is to directly monitor the die temperature with an external temperature sensor, as discussed below.

In an analogous manner to the previous model, the averaged power level (die temperature) is computed by the integrator circuit 88 (or external temperature sensor output) and quantized to form an address to the three dimensional data storage structure 78. Each element of this data structure 78 contains a set of FIR filter coefficients that embodies the DCSP correction coefficients. Since this effect is typically significantly smaller than the main AM-AM and AM-PM characteristic, the address span in the integrated power axis may be significantly smaller than the signal amplitude address span. Thus it may be identified that this model permits the amplifier's nonlinearity to be characterized as a function of frequency, input signal level, rate of change of envelope and integrated past power profile (die temperature). The model permits the changes in nonlinearity to be predicted as the complex modulation trajectory travels through this multi-dimensional space. The order of this model 75 can be continually increased as new independent dependencies of the nonlinear amplifier characteristic are identified.

3.3.2.2.4. Third Order Extended Multi Kernel Nonlinear Power Amplifier Mode

Figure 18:
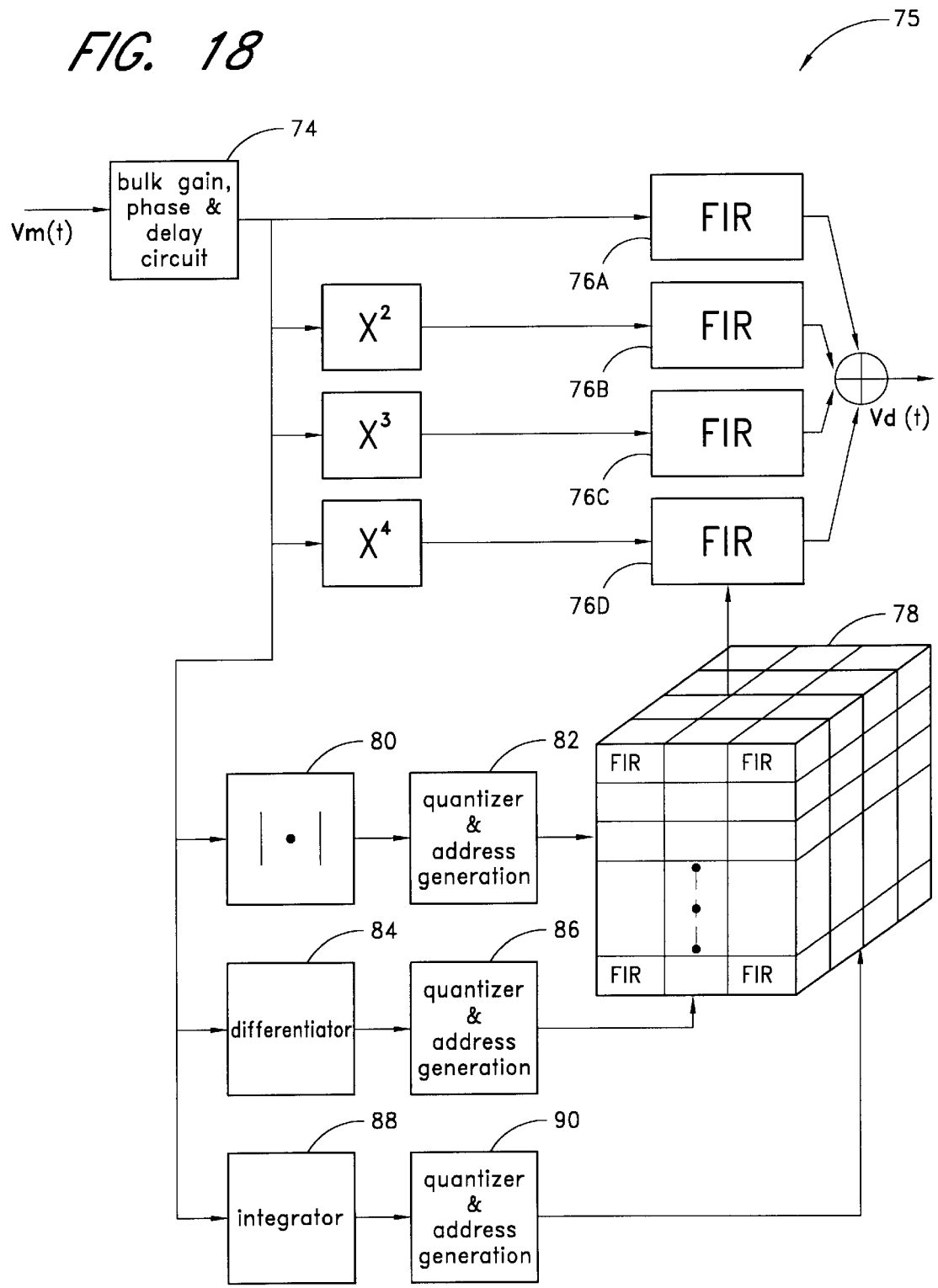

The previous sections described models 75 in which the stimulus to the amplifier 64 is broken into an increasing number of independent dependencies, i.e., model order. The construction of these models is based around a single FIR filter kernel. The logical extension of this model is to embody all possible nonlinear mechanisms. As illustrated in FIG. 18, this can be achieved by introducing second, third, fourth etc. kernels 76B–76D in which the amplifier's non-linearity causes an output signal to contain characteristics dependent upon higher order components of the input signal. In practice, only odd power nonlinearities would be expected to be observed. However, the model illustrated in FIG. 18 encompasses the most general nonlinearity that could be encountered.

The model simply requires that each element of the data structure 78 contain multiple sets of FIR filter coefficients, one set for each order filter 76A–76D included in the model. Although the diagram only illustrates four kernels, further extensions beyond the fourth power may also be included.

3.3.2.3. Computation of Model Parameters 3.3.2.3.1. Overview

Computation of the power amplifier's model parameters is a straightforward process consisting of three main steps. The first step computes the bulk gain, phase rotation and delay difference observed between the reference signal Vm(t) and the observed signal Vf(t). The resulting parameters are used to implement block 74 of the model 75. The next step is to compute the basic frequency response of the amplifier 64 so that an FIR filter 76 capturing the gain and phase variations through the amplifier as a function of frequency and amplitude is constructed. The coefficients of the FIR filter(s) are loaded into the data structure 78 of the model 75.

The third step invokes an adaptation engine that fine tunes the filter coefficients to minimize the mean square error between the observed power amplifier output signal Vf(t) and the predicted output signal Vp(t). Adaptation continues until an error floor is reached, which in turn causes the ACPCE to determine if the error floor is sufficiently small that the power amplifier model is sufficiently accurate for the particular application. If the error floor is deemed to be at a satisfactory level, the model coefficients are stored and the amplifier modeling process is considered to be complete. Alternatively, the amplifier model complexity may be increased and the adaptation engine re-engaged to fine tune the parameters until a lower error floor is reached. Multiple iterations of this process may be used with ever increasing amplifier model complexity until a satisfactory error floor is reached.

Each of these three steps will now be described in further detail.

3.3.2.3.2. Step 1: Bulk Gain, Phase and Delay Estimation

The bulk delay between the input reference signal Vm(t) and the observed amplifier output, Vf(t), is readily determined by examining the cross correlation between these two signals. The bulk delay is estimated by selecting the delay $\tau$ that maximizes the magnitude of the cross correlation function defined in Equation 3. Once this time delay has been computed, the bulk phase rotation may be estimated by examining the argument of the cross correlation function for the delay that maximizes the cross correlation function, Equation 4. In typical discrete time processing scenarios, the time delay $\tau$ may only be estimated in discrete sampling steps where the smallest time delay step is defined by the sampling/clock rate. In these scenarios, increased time delay estimation accuracy can be achieved by interpolating the observed waveform Vf(t) into secondary waveforms that are shifted by a fraction of a sampling period and subsequently recomputing Equation 3. Thus subsample time delay offsets in the correlation function may be examined. Consequently, the fractional time delay exhibiting the largest cross correlation magnitude defines the bulk time delay. Naturally, the bulk phase rotation can also be recomputed from the more accurate cross correlation value.

$$R(\tau) = \left| \sum_{t=-T}^{T} Vm(t)Vf(t-\tau)^* \right| \qquad \text{Equation 3}$$

$$\theta = \text{Arg}\left( \left( \sum_{t=-T}^{T} Vm(t)Vf(t-\tau)^* \right) \bigg|_{\tau=Rmax} \right) \qquad \text{Equation 4}$$

An alternative method for bulk delay estimation is to exploit cyclo-stationary properties of the input reference waveform Vm(t). This approach permits very accurate delay estimates to be computed but suffers from the inability to detect delay for certain classes of signal waveforms that do not exhibit band edge recovery properties, e.g. OQPSK. Correlation is generally preferred because it is reliable with signals that do not exploit cyclo-stationary properties.

The bulk gain of the system is readily computed by utilizing Equation 5 when the system is stimulated with the wideband signal stimulus. In essence, Equation 5 computes the average input and output power levels and estimates the amplitude ratio which by definition is the bulk gain of the system.

$$G = \sqrt{\frac{E\{Vm(t)^2\}}{E\{Vf(t)^2\}}} \qquad \text{Equation 5}$$

Once these three parameters have been computed, the power amplifier's observed signal output Vf(t) can be scaled, rotated and delayed to match the original input signal Vm(t). The differences that are now exhibited between these two signals represent the difference incurred due to the wideband frequency dependent nonlinear characteristics of the power amplifier. Thus, the first level of the amplifier model consists of a simple complex gain (scale and phase rotation) and a bulk propagation delay filter. The associated parameters of this circuit are precisely the values that have been computed in the above equations. This ensures that the predicted amplifier model's output waveform, Vp(t), is synchronized in time and matched in amplitude and phase with the output of the external amplifiers signal Vf(t).

3.3.2.3.3. Step 2: Wideband FIR Response Estimation

The second step in the development of the power amplifier model 75 is to compute the wideband frequency domain variations in gain and phase as a function of frequency and instantaneous input signal amplitude or power. This is readily achieved by comparing Vm(t) and Vf(t) for each of the individual narrowband signals that were used to stimulate the amplifier up to $P_{sat}$. For each frequency, a vector of gain, k, and phase, θ, responses is compiled which is indexed by the magnitude of the input signal, Vm(t). For a particular frequency and input amplitude level, the instantaneous gain and phase response may be computed from Equation 6.

$$k_{freq,amplitude} = \sqrt{\frac{E(Vf(t)(Vf(t)^*))}{E(Vm(t)(Vm(t)^*))}} \Bigg|_{|Vm(t)|=amplitude} \quad \text{Equation 6}$$

$$\theta_{freq,amplitude} = arg(Vf(t)(Vm(t)^*))|_{|Vm(t)|=amplitude} \quad \text{Equation 7}$$

Figure 19:
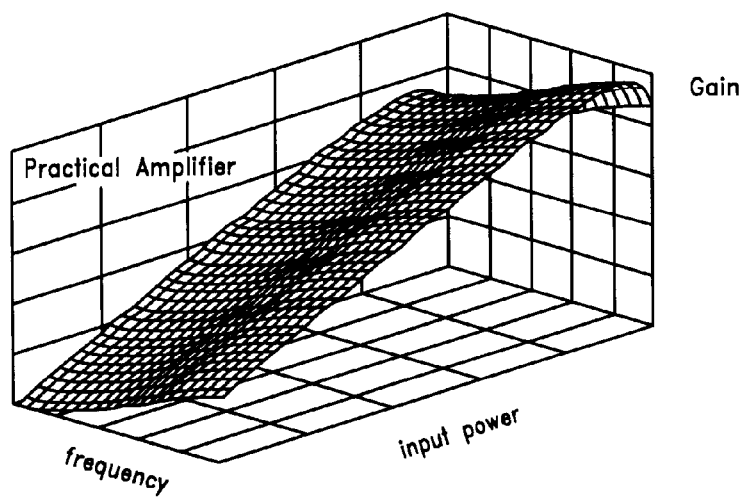
FIG. 19 illustrates a typical amplifier's nonlinear frequency domain AM-AM surface.

The set of resulting vectors are then stacked to form a 2-dimensional matrix with frequency and amplitude axes. Each element of the matrix stores the amplitude and gain response of the amplifier at a particular frequency and input amplitude level. FIG. 19 illustrates the gain response contained within the matrix.

Figure 20:
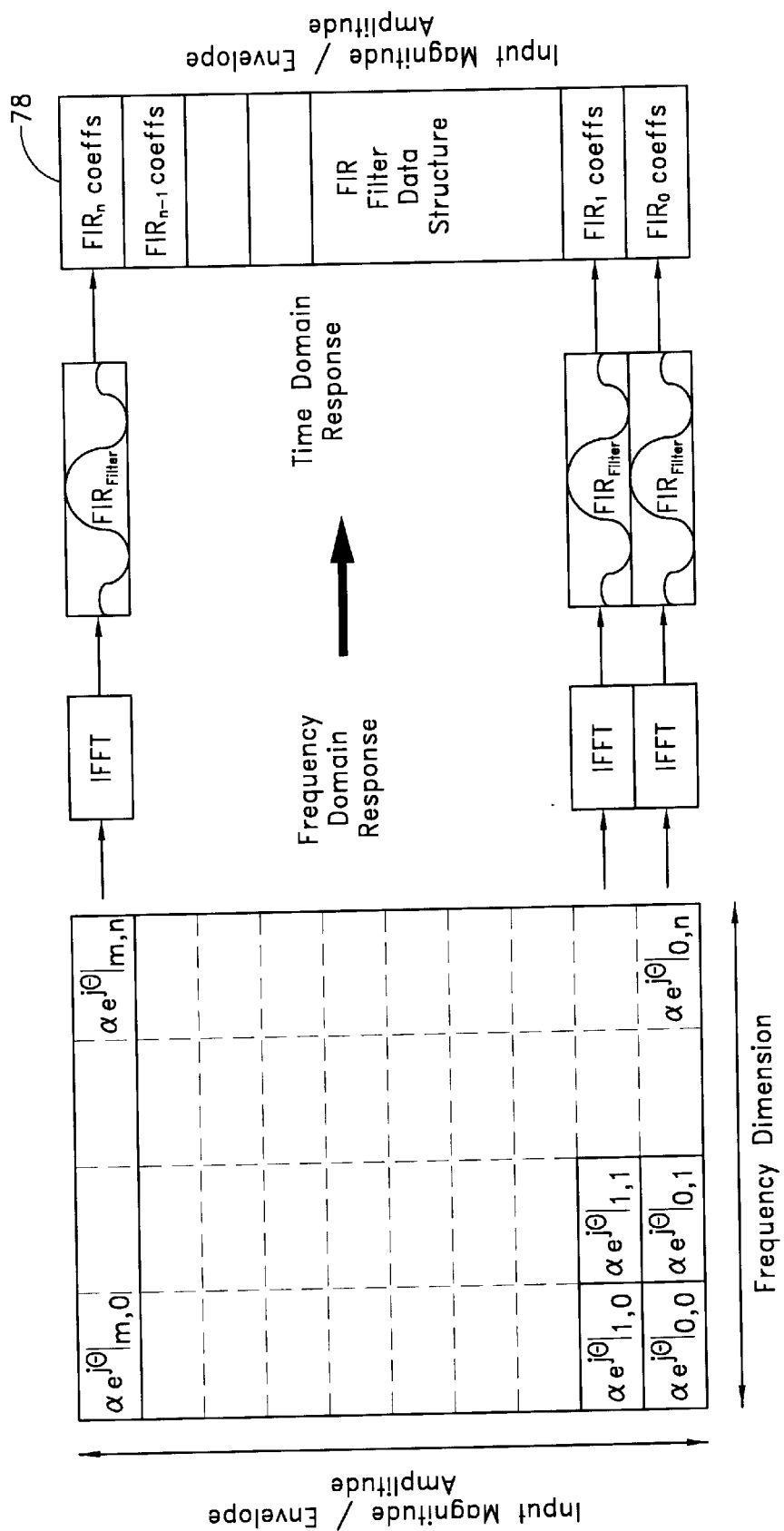
FIG. 20 illustrates a process for computing the FIR filter coefficients used by the power amplifier model.

The individual FIR filters that describe the wideband frequency domain response of the amplifier 64 are computed by taking a sub matrix or vector from the matrix in a cross dimension of constant amplitude and varying frequency. The FIR filter coefficients are computed by taking an inverse Fourier transform (IFFT) of this vector to compute the time domain filter taps. Although this process is straightforward for those skilled in the art, attention should be paid to IFFT scaling to ensure accurate gain response. This process is repeated for all input signal amplitude levels and the resultant FIR filter set is stored in the data structure 78 of the power amplifier model 75. The process is illustrated in FIG. 20.

The above procedure permits the least complex model illustrated in FIG. 15 to be estimated with potentially non-optimum taps values. Typically the inverse FFT will be computed assuming an excess of filter taps is permissible followed by truncation to a practical number after frequency to time domain conversion has occurred. However, because the model 75 is only used in estimating initial correction coefficients for the DCSP, and not real time operation, a larger number of taps may be employed. This ensures that the difference between the power amplifier's actual output Vf(t) and the model's predicted output Vp(t) is minimized. In a preferred embodiment, a 256 element IFFT is used to compute FIR filters with 256 taps, and the result is then truncated to 64 tap elements for use within the amplifier model.

3.3.2.3.4. Adaptation of Model Coefficients (for the purposes of increasing model accuracy)

Once the initial parameters for the basic model 75 have been computed, the wideband signal is repeatedly passed through the model and the difference between the actual power amplifier's response, Vf(t), and the model's predicted output, Vp(t), is compared. For each pass, FIR filter coefficients are adapted using a standard LMS, RLS or Kalman filter algorithm. Block oriented and nonlinear versions of these schemes may also be used to enhance convergence speed and reduce the number of iterations required to reach the error floor. The adaptation engine preferably optimizes the estimate of a particular FIR filter embedded within the power amplifier model's data matrix 78 only when the input signal's properties cause the indexing/addressing circuit to access the associated data element containing the FIR filter's coefficients. This is important because it permits a single FIR filter to be stored for multiple independent indexing variables. The ACPCE provides temporary storage during SID for intermediate calculation products that arise on a FIR filter by FIR filter basis if the extended adaptation algorithms such as RLS and Kalman filtering are used.

The adaptation process continues until no further improvement in reduction of the error floor is observed. At this juncture the overall waveform vector error magnitude is examined to determine the accuracy of the model 75. The waveform vector error magnitude is defined by Equation 8.

$$WVE = \frac{\sum_{i=0}^{N-1} |Vf(i) - Vp(i)|^2}{N} \quad \text{Equation 8}$$

If the waveform vector error magnitude is sufficiently low, the model 75 is considered sufficient for purposes of computing the initial DCSP coefficients. However, as discussed earlier, this is unlikely for particularly high powered amplifiers. Consequently, the model complexity is increased and the adaptation algorithm is permitted to further improve the FIR filter coefficients.

If a second order or greater model 75 is used, the dimensionality of the data structure 78 is immediately increased. When this occurs the previously computed FIR filter coefficients are initially propagated throughout the data structure 78 assuming that no variation in FIR coefficients occurs as a function of the new dimension. The change in coefficient values occurs when the adaptation engine is permitted to evolve the FIR coefficient values as a function of the new input dimension addressing variable. As the model complexity increases, differentiated and integrated functions 84, 88 are used to form addressing indices into the model. Since the time constant, span and associated parameters of these circuits are initially unknown, several sets of iterations may be required from the initial starting point as the parameter space is linearly explored.

Figure 21:
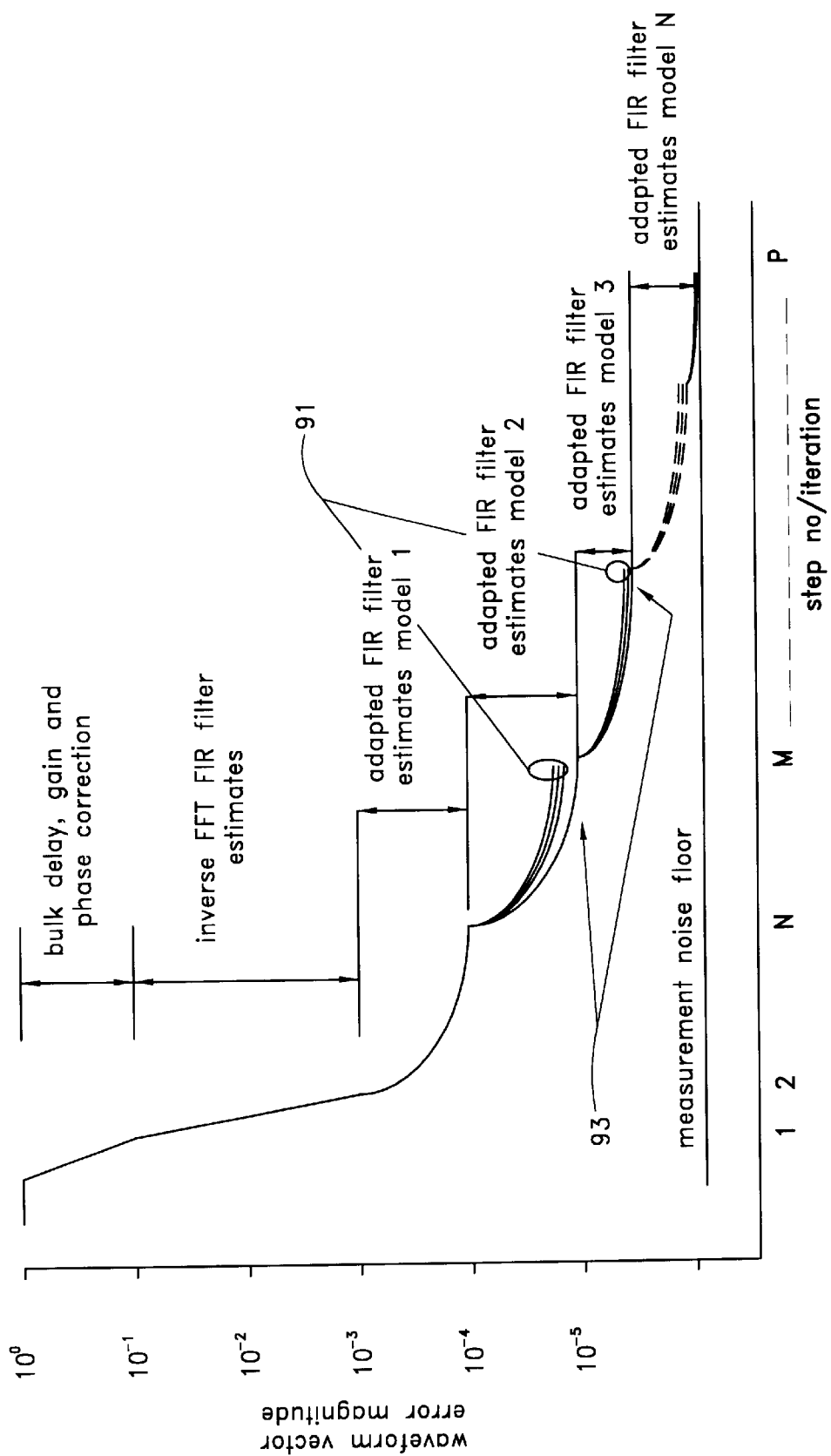
FIG. 21 illustrates a predicted waveform error magnitude trajectory during an iterative model adaptation process.

The error convergence floor is illustrated in FIG. 21. As depicted by FIG. 21, as the model complexity is increased, greater numbers of iterations may be required as the algorithm searches the parameter space while seeking the lowest error floor that can be converged upon. The uppermost curves 91 correspond to error floors associated with non-optimal estimates of integrator and differentiator span and time constant parameters. The lower curves 93 correspond to error floors associated with optimal estimates of such parameters.

After the parameter space has been searched, the FIR filter coefficients that correspond to the lowest error floor and circuit parameters are stored while the waveform vector error magnitude is computed to determine overall performance. If the performance is satisfactory, the model's final parameters are stored and the model estimation process is considered complete. Otherwise, the model complexity is increased and the process repeated. Naturally, this process can continually increase the complexity of the model 75 until the behavior of the amplifier 64 is fully characterized.

Examination of FIG. 21 reveals that the waveform vector error magnitude rapidly falls as the model 75 initially incorporates the bulk gain, phase and delay characteristics of the amplification chain 64. Further, impressive gains are made as the FIR filters incorporate the wideband frequency domain characteristics of the amplifier. Additional reductions in the error floor are increasingly harder to achieve as variations in the rate of change of the signal's envelope and the level of power dumped in the transistor die (as heat) are taken into account.

3.3.2.3.4.1. Flow Diagram

Figure 22:
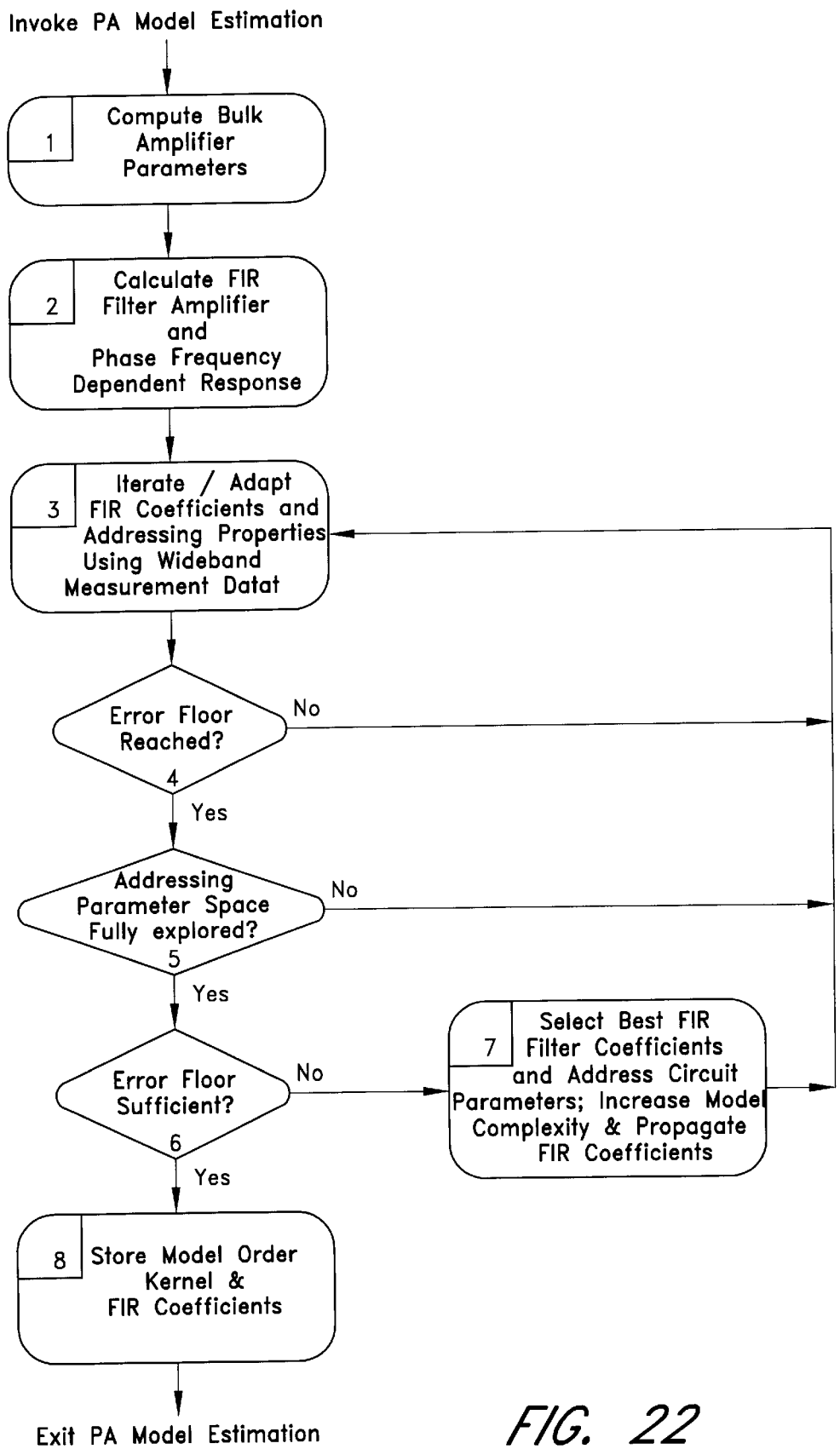
FIG. 22 is a flow diagram of the adaptation process depicted in FIG. 21.

The flow diagram for the adaptation process algorithm described in the previous section is detailed in FIG. 22.

3.3.2.3.4.2. Basic LMS Adaptation Engine for Model Parameters

FIG. 23 illustrates the aim of the adaptation process undertaken by the ACPCE as it adjusts the FIR filter coefficients of the wideband power amplifier model 75. The diagram shows that initially the actual power amplifier output Vf(t) differs from the output signal Vp(t) predicted by the wideband power amplifier model 75. The ACPCE adaptively updates the power amplifier model's FIR filter coefficients until either the difference between the observed and predicted signals is eliminated or an error/convergence floor has been reached. To achieve this goal, the ACPCE employs an LMS based algorithm to compute the iterative updates to the FIR filter coefficients. LMS is particularly attractive because of its simplicity; however, in applications in which convergence speed during SID is important, fast convergent algorithms such as momentum LMS, RLS and Kalman filtering techniques may be more desirable.

The complex coefficients of the FIR filter 76 represent the parameter values that have to be determined. This may be achieved utilizing Equations 9 and 10, in which: X(t) is the state vector of estimated FIR filter coefficients and the +/− nomenclature is used to indicate update vector parameters and current vector parameters; $V_{error}(t)$ is the current difference between the observed power amplifier signal sampled from the analog downconversion and the expected output that was predicted by the wideband power amplifier model 75 used for system identification; $\Delta$ is an update rate control parameter; and Vm(t) is a vector of captured wideband stimuli samples that were used to drive the input to the numerical model 75 at the same time instant as the implemented power amplifier.

$$\text{Verror} = Vf(t) - Vp(t) \quad \text{Equation 9}$$

$$[X_+] = [X_-] + \Delta \text{Verror}[Vm(t)] \quad \text{Equation 10}$$

For a three tap FIR filter example, Equation 10 would be represented as Equation 11.

$$\begin{bmatrix} Tap_{-1_+}(t) \\ Tap_{0_+}(t) \\ Tap_{+1_+}(t) \end{bmatrix} = \begin{bmatrix} Tap_{-1_-}(t) \\ Tap_{0_-}(t) \\ Tap_{+1_-}(t) \end{bmatrix} + \Delta Verror(t) \begin{bmatrix} Vm(t-1) \\ Vm(t) \\ Vm(t+1) \end{bmatrix} \quad \text{Equation 11}$$

This algorithm is a direct implementation of the standard LMS algorithm. It is important that the time index of the captured stimuli and observation waveforms be consistent, and that the delays in the compensation network be properly handled. This is a normal requirement that is known to those skilled in the use of this class of algorithms. The iteration explicitly defined within Equations 9 and 10 is repeatedly executed over the sampled wideband data set until the residual RMS value of the error voltage Verror(t) has finished converging i.e., reached an error floor.

As mentioned above, the adaptation engine preferably optimizes the estimate of a particular FIR filter embedded within the power amplifier model's data matrix 78 only when the input signal's properties cause the indexing/addressing circuit to access the associated data element. The ACPCE provides temporary storage during SID for intermediate calculation products that arise on a FIR filter by FIR filter basis if the extended adaptation algorithms such as LMS momentum, RLS and Kalman filtering are used to achieve faster convergence times. These algorithms are discussed in the following sections.

3.3.2.3.4.3. Recursive Least Squares (Direct Form) Also Known as the Kalman Filter Update Although the computational simplicity of the LMS algorithm is very attractive, its convergence speed can be prohibitively slow. This can be overcome by utilizing the RLS or Kalman filter algorithms. These algorithms exhibit significantly faster convergence rates but at the expense of increased computational complexity. These algorithms may be used within the wideband predistorter design as a direct replacement for the LMS algorithm and employed in an identical manner. These algorithms are widely defined and explained in the public domain literature, consequently the algorithm will simply be defined using the nomenclature of Proakis without further explanation.

$$s_{obs}(t) = Y\frac{T}{N}(t)C_N(t-1) \quad \text{Equation 12}$$

$$\text{Verror}(t) = s_{true}(t) - s_{obs}(t) \quad \text{Equation 13}$$

$$K_N(t) = \frac{P_N(t-1)Y_N^*(t)}{w + Y_N^T P_N(t-1)Y_N^*(t)} \quad \text{Equation 14}$$

$$P_N(t) = \frac{1}{w}[P_N(t-1) - K_n(t-1) - K_n(t)Y_N^T(t)P_N(t-1)] \quad \text{Equation 15}$$

$$C_N(t) = C_N(t-1) + P_N(t)Y_N(t)\text{Verror}(t) \quad \text{Equation 16}$$

3.3.2.3.4.4. Extended Kalman Filter for Nonlinear Estimation Scenarios

As indicated above, compensation circuitry may be included in the amplifier design to compensate for quadrature modulator and demodulator imperfections. These circuits may have internal interactions that cause the linear LMS and RLS algorithms to fail to correctly identify the true system parameters of the wideband amplifier. This occurs because the adjustment of the IQ modulator parameters will modify the gain and phase response of the circuit which is compensated for by the FIR filter coefficients. This interaction does not necessarily exhibit a linear characteristic, and as such, may cause the linear estimation algorithms to fail. This deficiency may be readily overcome by employing the extended Kalman filter algorithm which is designed to solve this class of problem. The ability of the extended Kalman filter to identify the system components despite the nonlinear interactions is achieved because the algorithm identifies the interactions between parameters as well as the parameters themselves. This naturally causes a significant increase in computational complexity. Consequently, this algorithm is preferably only used if it can be identified that nonlinear interactions between compensation parameters occur.

The extended Kalman filter algorithm for nonlinear estimation environments is widely defined and explained in the public domain literature, consequently the algorithm is simply specified below using the nomenclature of Proakis without further explanation.

$$s_{obs}(t)=Y_N(t)\{C_N(t-1)\} \quad \text{Equation 17}$$

$$V_{error}(t)=s_{true}(t)-s_{obs}(t) \quad \text{Equation 18}$$

$$C_N(t)=C_N(t-1)+Y_N^*(t)[\text{Verror}(t)] \quad \text{Equation 19}$$

$$P_N(t)[I-Y_N H_N(C_N(t-1))]P_N(t-1) \quad \text{Equation 20}$$

$$Y_N=P_N(t-1)H_N^T(C_N(t-1))[H_N(C_N(t-1))P_N(t-1)H_N^T(C_N(t-1))+R_N]^{-1} \quad \text{Equation 21}$$

$$H_N(C_N(t-1)) = \frac{\partial h_N(C_N(t-1))}{\partial C_N(t-1)} \quad \text{Equation 22}$$

3.3.3. State 3: Compute DCSP Model's Compensation Parameters

3.3.3.1. Overview

Figure 24A:
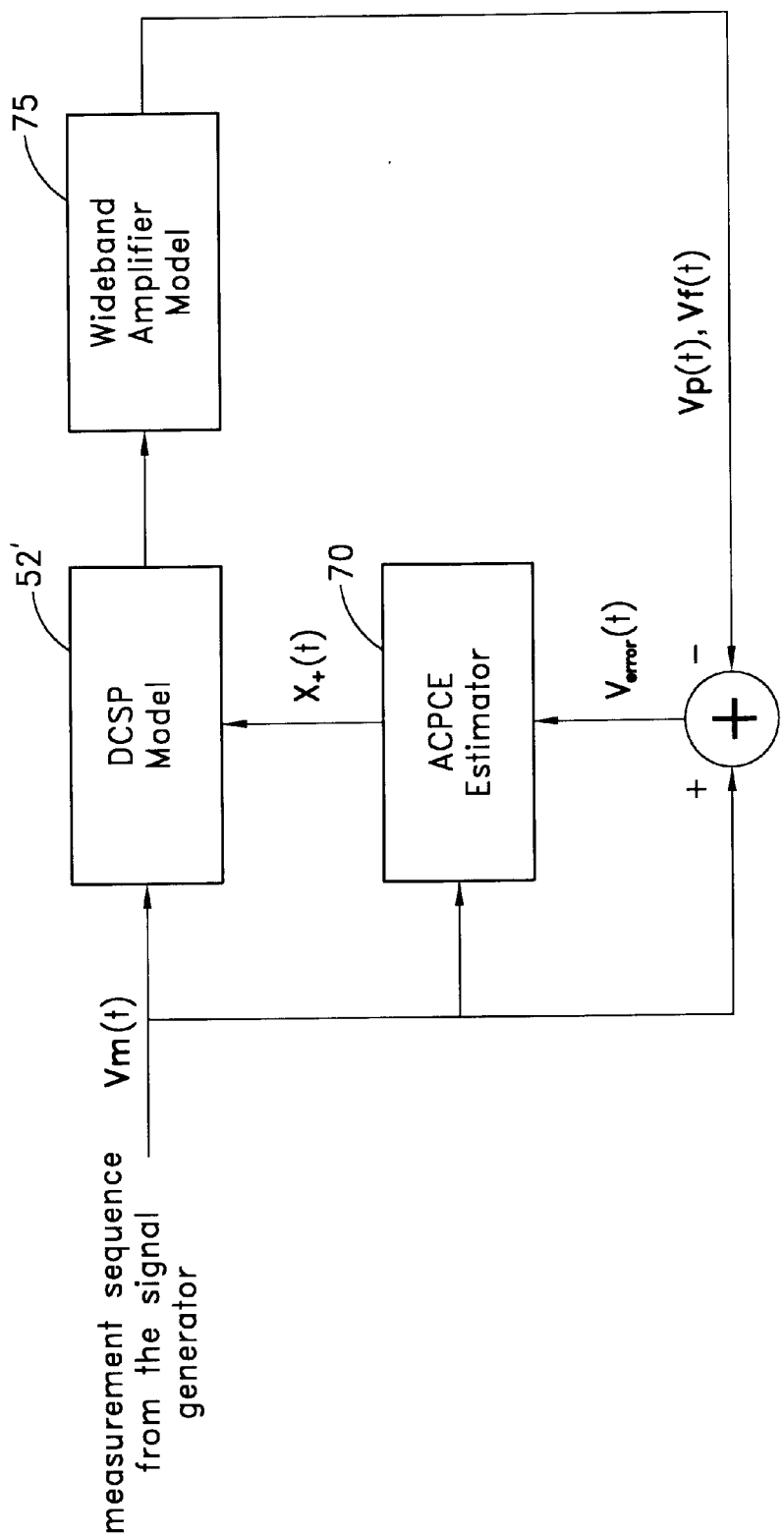
FIG. 24A illustrates a process for initially computing DCSP compensation parameters, and corresponds to state 3 in FIG. 10.
Figure 24B:
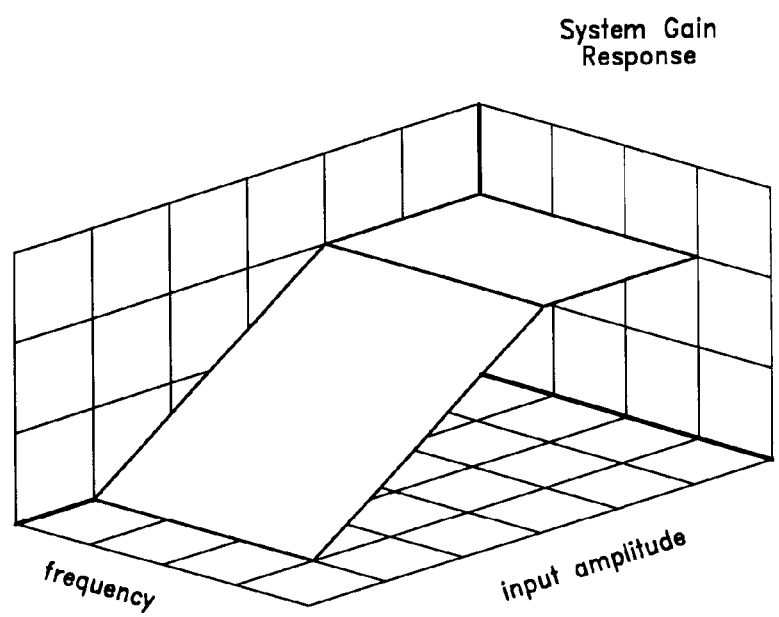
FIG. 24B illustrates a desired system response sought through adjustment of the DCSP parameters.

FIG. 24A illustrates states 3 and 4 of the SID process depicted in FIG. 10. A numerical model 52' of the DCSP, or alternatively the DCSP itself, is cascaded with the wideband amplifier model 75. The objective is to compute and/or adapt the coefficients of the DCSP 52 so that the output of the amplifier model, Vp(t), is an undistorted yet amplified replica of the input signal, Vm(t). The ACPCE 70 is responsible for computing or adjusting the coefficients of the DCSP compensation circuit. As illustrated in FIG. 24B, the overall objective of this process is to adjust the DCSP coefficients so that the overall system response is a pure linear function of the input signal's frequency and instantaneous amplitude. Naturally, the amplifier cannot source to the antenna load more energy than the saturated power level, so the diagram illustrates that the system's output power consolidates at a maximum level.

One of two alternative methods are preferably used to compute the DCSP's coefficients. A simple method, which may fail for very high power amplifier systems, is to select a DCSP structure that matches the complexity of the power amplifier model 75 and attempt to adapt the DCSP coefficients from initial default settings directly. Although this method is acceptable under most circumstances, it can fail to converge to the correct coefficients if the power amplifier 64 exhibits strong nonlinearity and memory effects.

A more reliable approach, referred to herein as direct estimation, is to initially reduce the power amplifier model 75 to a simple first order single kernel model (see FIG. 15), and directly compute the DCSP coefficients that combat the frequency dependent variations in the AM-AM and AM-PM characteristic of the amplifier model. The ACPCE then follows this process by increasing the DCSP complexity and adjusting its coefficients in an adaptive manner to mitigate the characteristics of the full wideband power amplifier model. With this approach, the parameters converge to the correct values as the frequency dependent AM-AM and AM-PM characteristic captures the bulk behavioral characteristic of the amplifier 64; in addition, the minimum error solution found by the adaptive process is the overall global minimum, not an undesirable local minimum. As mentioned earlier, this is illustrated in FIG. 21.

3.3.3.2. Initial Direct Estimation of the DCSP Coefficients

Direct estimation of the initial DCSP coefficients proceeds by reduction of the wideband power amplifier model 75 to a simple first order single kernel model of the type illustrated in FIG. 15. This provides a set of FIR filters that are indexed only by the instantaneous power or signal amplitude. Reduction of the amplifier model is readily undertaken for highly complex amplifier models by simply extracting a vector of FIR filter coefficients from the multi-dimensional data structure 78 by selecting that vector that is indexed by a variation in the signal power while the other indexing dimensions are held constant at nominal operating levels.

Embodied within the FIR filter coefficients is the complex gain, i.e., gain and phase response, of the amplifier at each frequency over which the amplifier may operate. This information is directly accessible if the FFT of each FIR filter is undertaken by the ACPCE to form a matrix of amplifier complex gains that are indexed by input amplitude and frequency. The ACPCE then creates an additional complex gain matrix that represents the behavior of the DCSP coefficients and attempts to compute the required complex gains such that the overall cascade of the DCSP and power amplifier provides a linear system gain. The procedure according to a preferred embodiment is described in the following paragraphs.

Figures 2, 25A:
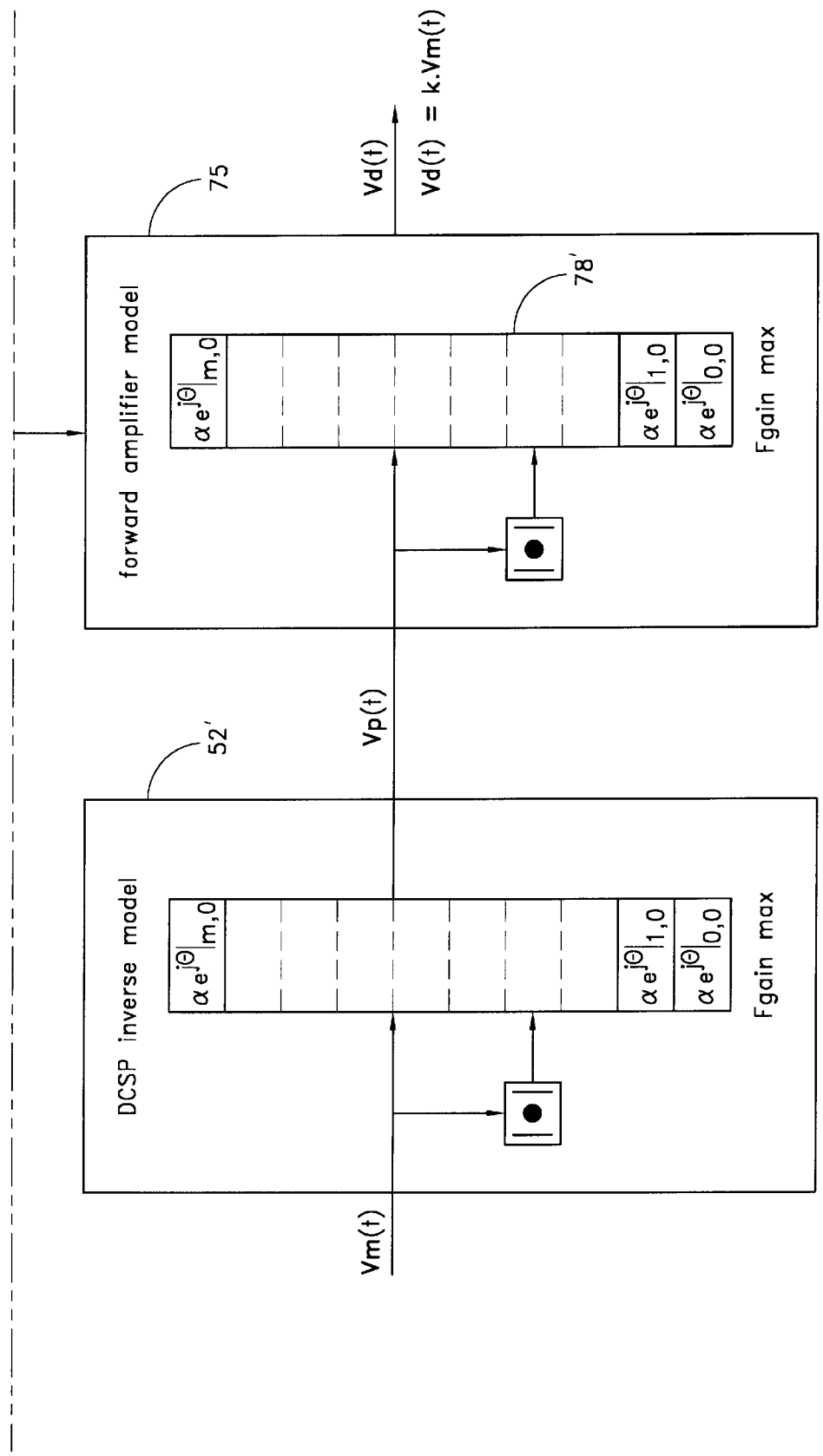
FIG. 25A illustrates a model inversion process.

FIG. 25A illustrates the first detailed step that is taken in the direct estimation of the DCSP predistortion correction coefficients during the SID process. As mentioned above, the entire forward amplifier model's multi-dimensional data structure 78 is temporarily collapsed to a single dimension data structure 78' that is indexed by the instantaneous amplitude of the amplifier's input signal. This will result in a vector that contains a set of complex FIR filter coefficients for each element of the vector. The diagram shows how the FFT is taken for each set of FIR filter coefficients to provide a two dimensional array that permits the amplifier's AM-AM and AM-PM response to be determined at different frequencies and input signal amplitudes. Computation of the DCSP predistortion coefficients proceeds by searching for the frequency at which the minimum saturated power output of the amplifier is observed. This operating point is then employed to set the normalized system gain, k, for the overall cascade of the DCSP and the power amplifier.

Once the system gain, k, has been set, the ACPCE selects a vector of AM-AM and AM-PM amplifier responses for a given operating frequency, as shown in FIG. 25A. For each frequency the ACPCE cascades a simple one dimensional data structure indexed by amplitude with the corresponding highly simplified amplifier model.

Figure 26C:
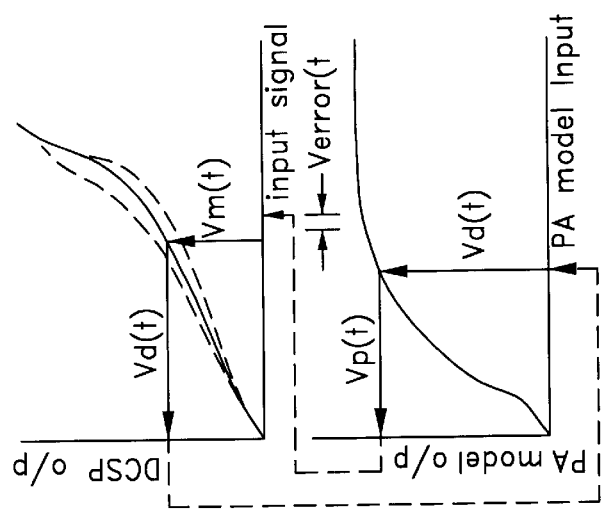
FIG. 26, which consists of FIGS. 26A–26C, illustrates the iterative adjustment of the DCSP parameters.
Figure 26B:
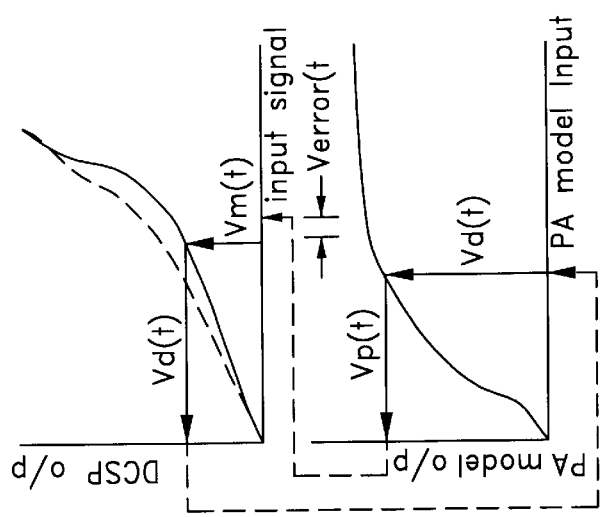
Figure 26A:
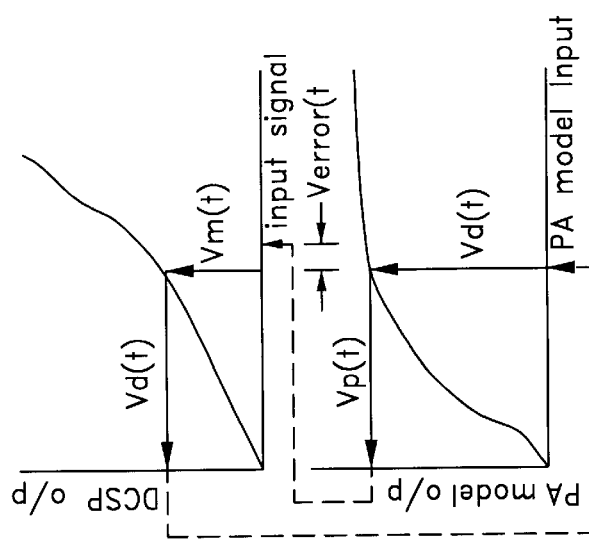

The ACPCE then seeks DCSP coefficients for which this linear gain is achieved for all frequencies and instantaneous amplitudes exhibited by the input signal. FIG. 26 illustrates how the DCSP coefficients are adjusted. Since the response of the system is the cascade of two highly nonlinear systems, it is difficult or impossible to directly solve for the DCSP coefficients. Therefore, the DCSP's complex gain is instead iteratively adjusted until the system gain, k, is achieved. This process may use the simple RASCAL algorithm (see Andrew S. Wright and Willem G. Durtler "Experimental performance of an Adaptive Digital Linearized Power Amplifier", IEEE Trans. Vehicular Technology, Vol 41, No. 4, November 1992) or simple application of a proportional control algorithm.

This process is undertaken for each element of the DCSP's frequency domain response matrix so that the following conditions are satisfied.

$$Vp(t)=Vm(t)F(|Vm(t)|)G(F(Vm(t))) \quad \text{Equation 23}$$

$$k \cdot Vm(t)-Vp(t)=0 \quad \text{Equation 24}$$

Figure 25B:
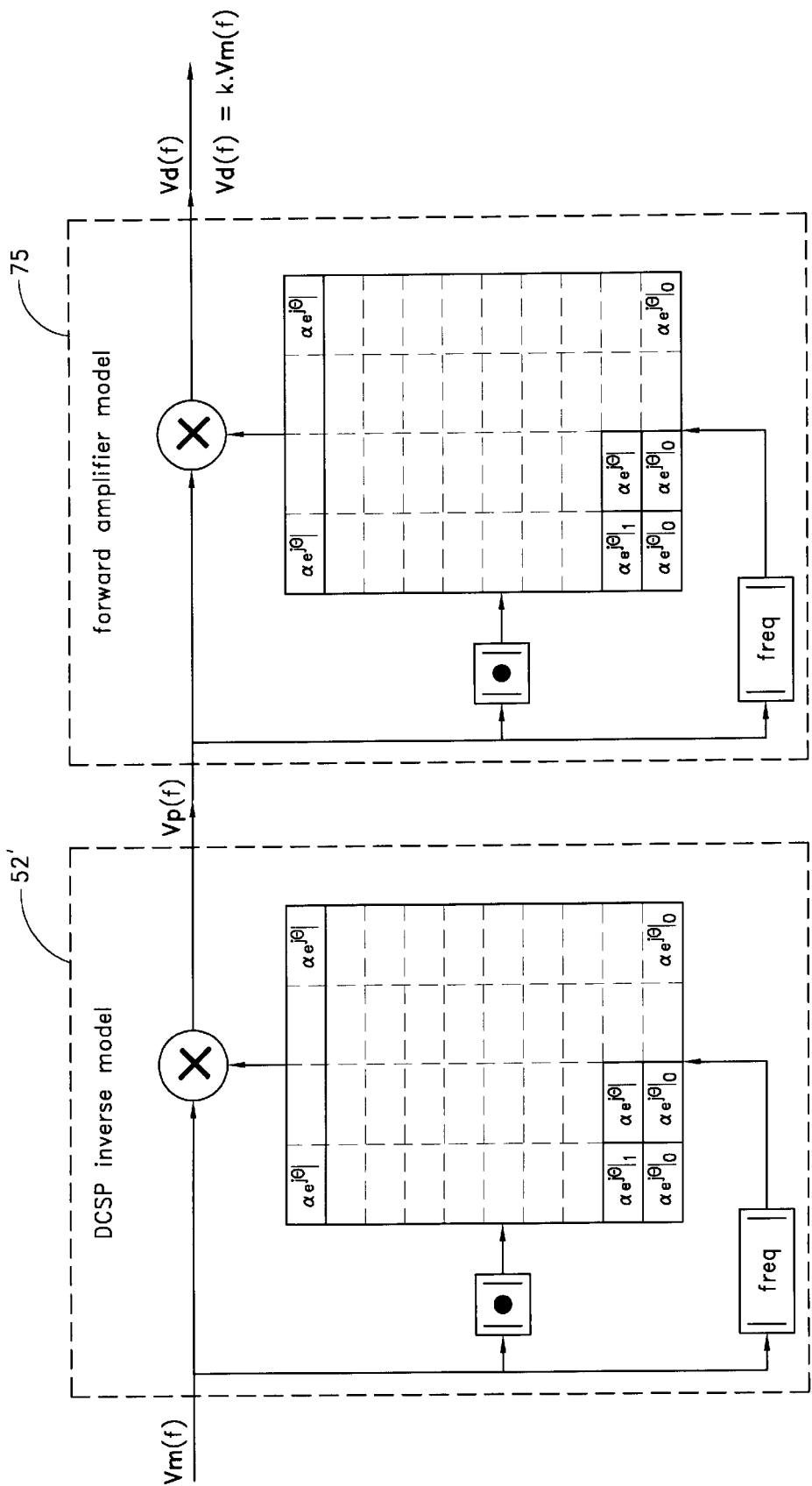
FIG. 25B illustrates a cascade of an inverse forward model and a simplified amplifier forward model.

This approach permits the ACPCE to compute a frequency and amplitude indexed matrix which contains the AM-AM and AM-PM response of the predistortion coefficients that will be utilized by the DCSP. FIG. 25B illustrates a descriptive/notional picture of the cascade of the predistortion inverse model 52' and the amplifier's model 75 in the frequency domain such that the overall response is linear.

Once the DCSP's frequency domain complex response matrix has been estimated, the ACPCE converts this back to the time domain by performing an inverse FFT upon a vector of complex gains indexed by a constant input amplitude and varying frequency extracted from the frequency domain complex response matrix. This creates a set of FIR filter coefficients that may be used in the DCSP 52 which are indexed/selected by the instantaneous amplitude of the input signal, Vm(t). This process is directly analogous to that discussed above and illustrated in FIG. 20. Thus the DCSP may now be used to correct for the major imperfections introduced by the frequency dependent AM-AM and AM-PM characteristic of the wideband power amplifier 64.

3.3.4. State 4: Algorithms;—Adaptively Seek DCSP Compensations Parameters 3.3.4.1. Overview The following sections outline the process by which the computed DCSP parameters are fine tuned using the numerical models of the DCSP and the amplification chain.

3.3.4.2. DCSP Parameter Expansion

Figure 27:
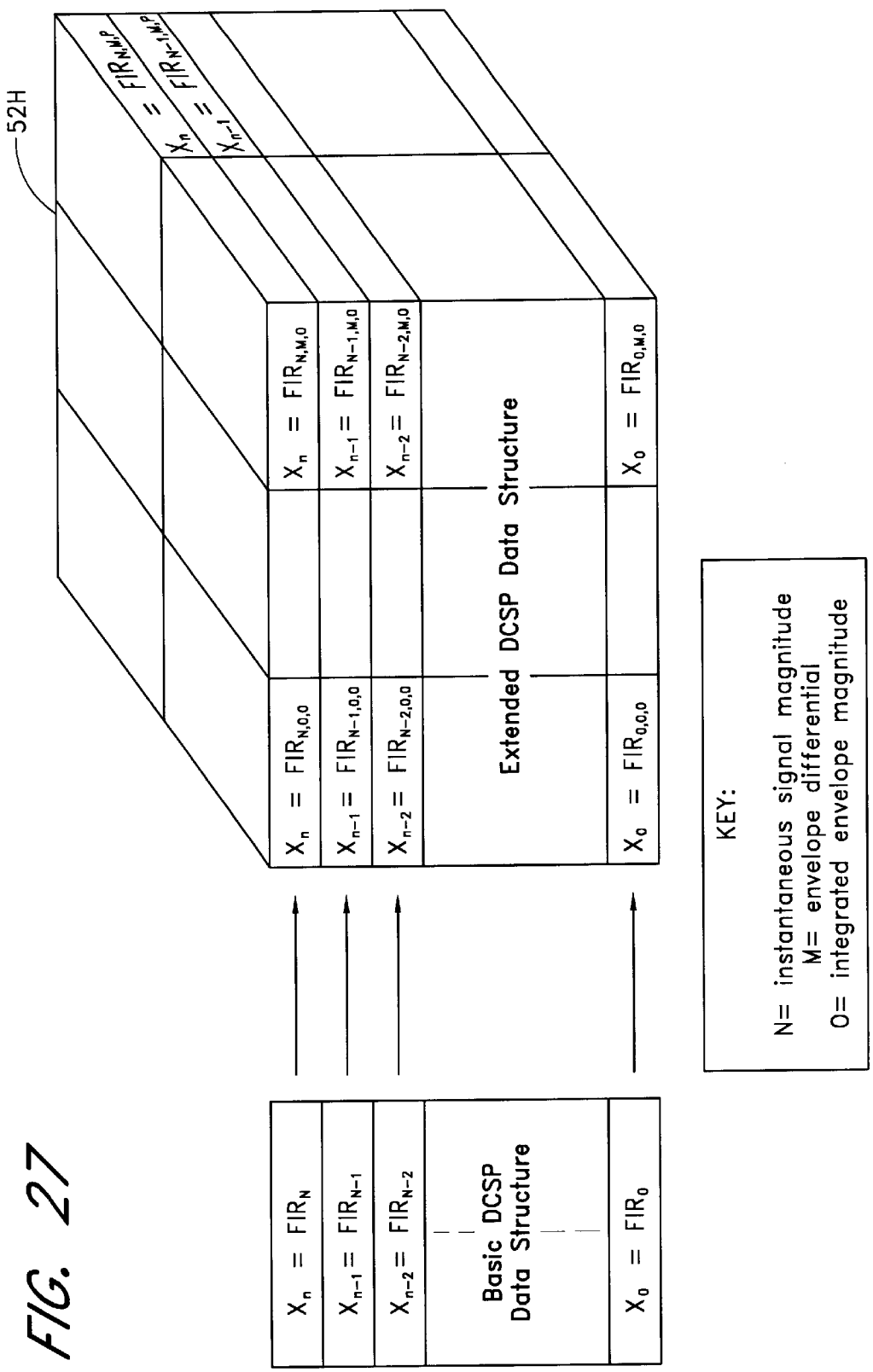
FIG. 27 illustrates the propagation of the computed DCSP parameters into the multi-dimensional data structure of the DCSP.

Once the FIR filter coefficients have been computed, they are propagated into the extended DCSP circuit's coefficient data structure 52H assuming that no variation is required other than a function of instantaneous input amplitude. Thus, for example, if the DCSP is provisioned with three dimensions of correction for the characteristics of the power amplifier, the coefficients of the data structure will appear to be static in the addressing direction of the second and third dimensions. This is illustrated in FIG. 27.

3.3.4.3. DCSP Parameter Adaptation

As depicted by FIG. 24A, once the basic DCSP FIR filter coefficients have been propagated into the extended DCSP data structure 52H, the coefficients of each FIR filter are adjusted/adapted under the control of the ACPCE adaptation engine (estimator) 70. The objective of this adjustment process is for the output Vp(t) of the cascaded DCSP model 52' and wideband power amplifier model 75 to be a scaled replica of the input signal Vm(t), exhibiting a minimum vector error magnitude. The algorithms used by the ACPCE adaptation engine 70 are set forth below.

3.3.4.3.1. Basic LMS Adaptation Engine for Model Parameters.

Figure 28D:
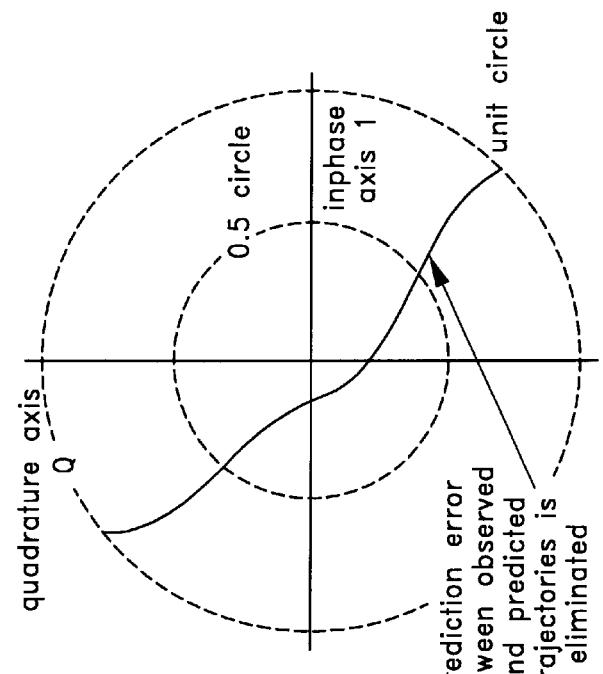
FIG. 28, which consists of FIGS. 28A–28D, illustrates the reduction in error between predicted and observed signal trajectories as the DCSP filter parameters are adjusted in state 4 of FIG. 10.
Figure 28C:
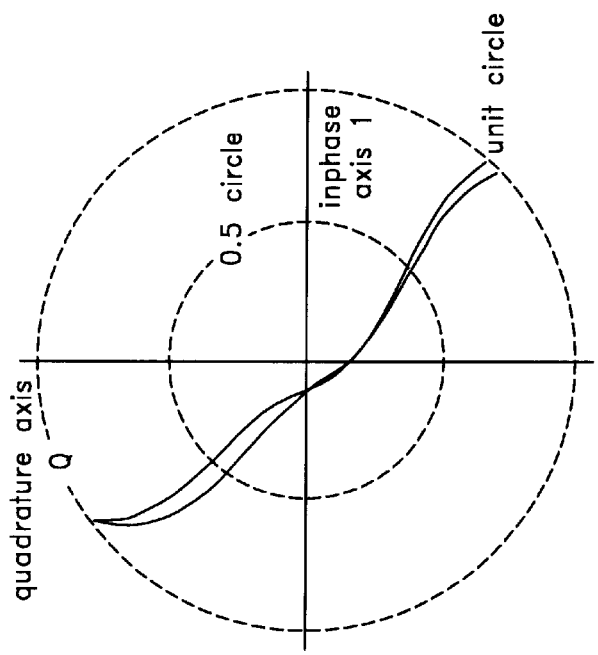

FIG. 28 illustrates the aim of the adaptation process undertaken by the ACPCE 70 as it adjusts the FIR filter coefficients of the DCSP circuit 52. The diagram shows that initially the actual output of the power amplifier model Vp(t) differs from the wideband input signal Vm(t). The ACPCE adaptively updates the DCSP's FIR filter coefficients until either the difference between the observed and input signals is eliminated or an error/convergence floor has been reached. To achieve this goal, the ACPCE employs an LMS based algorithm to compute the iterative updates to the FIR filters. LMS is particularly attractive because of its simplicity; however, in applications in which convergence speed during SID is important, fast convergent algorithms such as momentum LMS, RLS and Kalman filtering techniques may be used Equations 25 and 26 below represent a preferred LMS based algorithm for adjusting the complex filter coefficients, where: X(t) is the state vector of estimated FIR filter coefficients with the +/− nomenclature indicating update vector parameters and current vector parameters; $V_{error}(t)$ is the current difference between the wideband power amplifier model output Vp(t) and the wideband input signal; Δ is an update rate control parameter; and Vm(t) is a vector of wideband stimuli samples that were used to drive the input to the numerical model of the DCSP correction circuit. For a three tap FIR filter example, Equation 25 would be represented as Equation 27.

$$\text{Verror}=Vf(t)-Vp(t) \quad \text{Equation 25}$$

$$[X_+]=[X_-]+\Delta \text{Verror}[Vm(t)] \quad \text{Equation 26}$$

$$\begin{bmatrix} Tap_{-1_+}(t) \\ Tap_{0_+}(t) \\ Tap_{+1_+}(t) \end{bmatrix} = \begin{bmatrix} Tap_{-1_-}(t) \\ Tap_{0_-}(t) \\ Tap_{+1_-}(t) \end{bmatrix} + \Delta Verror(t) \begin{bmatrix} Vm(t-1) \\ Vm(t) \\ Vm(t+1) \end{bmatrix} \quad \text{Equation 27}$$

This algorithm is a direct implementation of the standard LMS algorithm. For successful operation, the time index of the captured stimuli and observation waveforms should be consistent, and the delays in the compensation network should be properly handled. This is a normal requirement that is known to those skilled in the utilization of this class of algorithms. The iteration defined within Equations 25 and 26 is repeatedly executed over the sampled wideband data set until the residual RMS value of the error voltage Verror (t) has finished converging i.e., reached an error floor.

In an identical manner to that incurred while seeking the FIR coefficients of the amplifier model 75, the computation and update of each FIR filter's coefficients occurs on a FIR filter by FIR filter basis, with selection of a particular FIR filter being governed by the addressing of the data structure 52H.

3.3.4.3.2. Recursive Least Squares (Direct Form) Also Known as the Kalman Filter Update Although the computational simplicity of the LMS algorithm is very attractive, as noted above, its convergence speed can be prohibitively slow. This can again be overcome by utilizing the RLS or Kalman filter algorithms, which exhibit significantly faster convergence rates but at the expense of increased computational complexity. These algorithms, which are summarized by Equations 12–16 above, may be used within the wideband predistorter design as a direct replacement for the LMS algorithm and employed in an identical manner.

3.3.4.3.3. Extended Kalman Filter for Nonlinear Estimation Scenarios.

As indicated above and shown in FIGS. 3 and 4, the DCSP may include a correction circuit 52B to compensate for quadrature modulator and demodulator imperfections. The correction circuit 52B may be desired because the quadrature modulator/demodulator processes may have internal interactions that prevent the linear LMS and RLS algorithms from correctly identifying the true system parameters for the amplifier model. This occurs because the adjustment of the IQ modulator parameters will modify the gain and phase response of the circuit which is compensated for by the FIR filter coefficients. This interaction does not necessarily have to exhibit a linear characteristic, and as such, may cause the linear estimation algorithms to fail.

This deficiency may be readily overcome by employing the extended Kalman filter algorithm which is designed to solve this class of problem. The ability of the extended Kalman filter to identify the system components despite the nonlinear interactions is achieved because the algorithm identifies the interactions between parameters as well as the parameters themselves. This naturally causes a significant increase in computational complexity. Consequently, this algorithm is preferably used only if it can be identified that nonlinear interactions between compensation parameters occur. The extended Kalman filter algorithms for nonlinear estimation environments summarized by Equations 17–22 above.

3.3.4.3.4. Convolution Update

Regardless of the actual adaptation algorithm used (see Sections 3.3.4.3.1–3), the iterative update of each FIR filter traditionally proceeds according to Equation 28, where $X_+$ represents the update FIR filter coefficients $X_-$ represents the existing values, and $\Delta X$ represents the update vector.

$$X_+ = X_- + \Delta X \qquad \text{Equation 28}$$

In the adaptive scenario illustrated in FIG. 24A, the ACPCE 70 compares the post distortion signal, Vp(t) [or Vf(t)], to an ideal reference signal, Vm(t), to create an error signal, Verror(t). The error signal is in turn used to adapt a pre-equalization structure.

A more effective update which permits a decrease in convergence time is to employ a convolutional update as defined by Equation 29. The difficulty associated with this approach is that the span of the FIR filter continues to grow with each update. This problem is readily overcome by simply truncating the length of the updated FIR filter coefficients $X_+$ to be identical the original length prior to the update, while retaining the most significant center taps of the FIR filter.

$$X_+ = X_- + X_- \hat{X} \Delta X \qquad \text{Equation 29}$$

3.3.5. State 5: Algorithms, Compute, Store and Load DCSP Correction Coefficient Parameters After the procedures of the previous sections have been completed, the SID process is considered complete. However, before engaging in active operation and entering the system acquisition and tracking phases (SAT), the ACPCE stores the computed DCSP coefficients in non-volatile memory so that the SID calibration need not be repeated if a power failure or system re-start occurs. Suitable memory technologies range from a field programmable metal mask, EEROM, flash ROM etc. Because the amplifier may operate at several different carrier frequencies, the SID process may be repeated several times before the SAT phase of operation is engaged. Under such a design requirement, several sets of SID DCSP parameters are stored in non-volatile memory so that rapid switches in the operating conditions can occur. In specific designs that are expected to display significant aging characteristics, periodic SID re-calibrations may be permissible, and as such, additional non-volatile storage such as FLASH ROM may be desirable to improve the reliability of the design.

3.3.6. ACPCE System Adaptation and Tracking Algorithms

Upon entering the track and update state (5) in FIG. 9, the ACPCE loads the previously computed compensation parameter values into the compensation circuit (DCSP). During the lifetime of the transmission event, the physical characteristics of the analog components may change as a function of temperature, aging, power supply droop etc.; consequently, the compensation parameters are adjusted to continually track and compensate for these changes.

Figure 29:
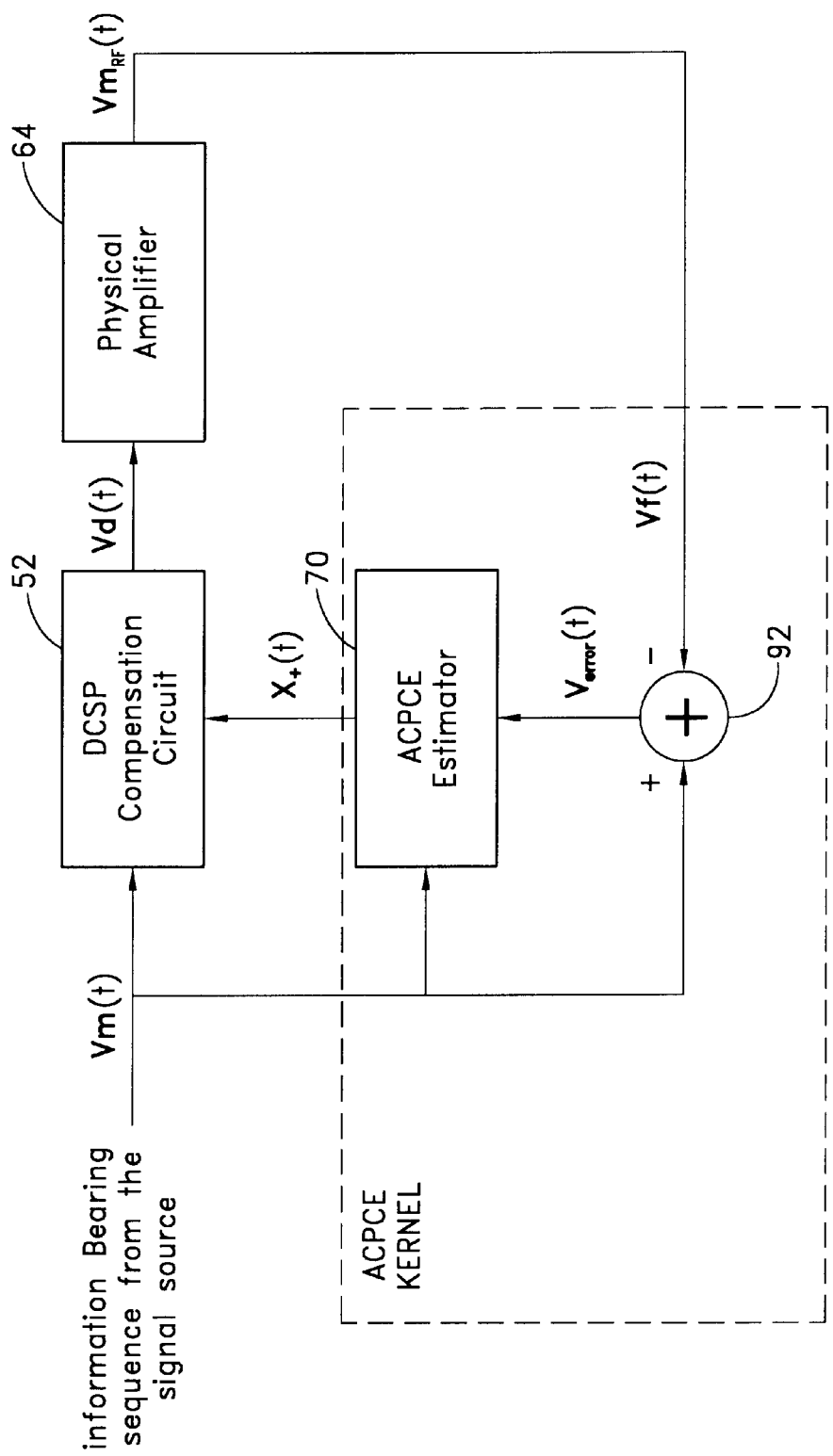
FIG. 29 illustrates the general process by which the ACPCE updates the DCSP's compensation parameters during transmission events.

The algorithms used to support this functionality are preferably identical to those used to initially evaluate the compensation parameters as described in the previous section. An important difference, however, is that the actual physical amplifier 64 is now used (as illustrated in FIG. 29) instead of the model. As a consequence, it is not practical for the compensation estimation algorithms to keep up with the large data rate and numeric processing power associated with the real time processes. As described above, sets of data samples are therefore preferably captured and processed off-line, as is possible since the amplifier characteristics change relatively slowly.

As illustrated in FIG. 29, the DCSP 52 is stimulated with a continuous data stream of the modulated signal Vm(t) from the signal source. The digital compensated signal is then applied directly to the amplification chain 64 (after D/A conversion), which outputs, $Vm_{RF}(t)$, a replica of the transmit signal. Initially, this signal should not deviate from the original baseband signal trajectory, $Vm_{true}(t)$, because the compensation parameters are set to accurate values which assume a perfectly compensated wideband nonlinear amplifier due to the previous SID process. Off-line captured data sample sequences of Vf(t) and Vm(t) are fed to the comparator 92 which generates an error vector which is utilized by the ACPCE 70 to compute adjustments to the compensation parameters. The update compensation parameters are provided to the DCSP via the parameter vector $X_+(t)$. The compensation estimator implemented by the ACPCE is a direct implementation of the LMS, RLS or Kalman filter algorithms which were discussed in the previous section. If, however, one or more of the compensation parameters exhibit nonlinear interactions, the extended Kalman filter is preferably used.

The above process of capturing observed data sequences, combined with numerical off-line computation, is repetitively used to ensure that the current values of the compensation parameters are sufficiently accurate to maintain regulatory power spectral emission, system modulation accuracy and amplifier NPR requirements. The accuracy of the parameter estimation can be enhanced by iterative updating of the parameters. Rather than calculating new parameters based only on the information in one sample sequence capture, the amount of change of the parameters can be controlled by calculating a weighted average of the current calculated values with progressively smaller contributions from previous parameter calculations. With this technique, the newly calculated parameters do not change significantly or suddenly on each training calculation due to non-ideal characteristics of the data of particular sample sets. This type of long term averaging helps to achieve a better overall correction rather than one that "jumps" around the ideal position.

As mentioned above, the transition from one parameter set to the next may be applied in steps spread over an interval of time to avoid sudden changes in the amplifier outputs. This may be done by looking at the new and previous parameter values, after the averaging described above (if used), and generating a sequence of parameter values on an interpolated path between the two sets of values. These would then be programmed into the filters and other correction systems in succession at intervals such that the change is made smooth and gradual. In an identical manner to that incurred while seeking the FIR coefficients of the amplifier model, the computation and update of each FIR filter's coefficients occurs on a FIR filter by FIR filter basis, with selection of a particular FIR filter being governed by the addressing of the data table 52H. As stated previously, the ACPCE preferably adjusts the estimate of a particular FIR filter embedded within the power amplifier model's data table only when the properties of the input signal, Vm(t), cause the indexing/addressing circuit to access the associated data structure element that contains the particular FIR filter's coefficients. This is important because it permits a single FIR filter to be stored for multiple independent indexing variables. The ACPCE provides temporary storage during SID for intermediate calculation products that arise on a FIR filter by FIR filter basis if the extended adaptation algorithms such as RLS and Kalman filtering are used to achieve faster convergence times.

In one embodiment, only the FIR filter coefficients of the DCSP data structure are evolved during the acquisition and tracking phase. It has been determined that due to the mechanical stability of the amplifier assemblies there is no requirement to adaptively adjust the time constant and span of the parameters of the differentiator 52J and integrator 52F that form part of the addressing function of the DCSP data structure 52H. However it should not be eliminated from consideration because future amplifier semiconductor technologies might exhibit significant variation in the required time constant and span of this particular system element. Consequently, adaptation of these parameters is a logical extension.

3.3.6.1. Summary of Update Algorithms

To summarize, the algorithms used during the system acquisition and tracking state for DCSP compensation parameter estimation are described in the following sections.

LMS Update: Sections 3.3.4.3.1 and 3.3.2.3.4.2

Recursive Least Squares (direct form) also known as Kalman Filter update: Sections 3.3.4.3.2 and 3.3.2.3.4.3.

Extended Kalman Filter for Nonlinear Estimation Scenarios: Section 3.3.4.3.3 and 3.3.2.3.4.4.

As discussed above, a convolution update may be used to achieve faster convergence during SID as a result of acknowledging particular attributes of the system architecture. In a similar manner, this technique can be directly applied during the SAT phase of operation. The discussion provided in Section 3.3.4.3.4 is directly applicable during SAT and as a consequence no further details are provided.

3.3.6.2. Non-linear Filtered-input Adaption Mode

FIG. 29, discussed above, illustrates a preferred embodiment for the operation of the SAT adaption algorithms that are utilized for normal operation during tracking mode. While in the tracking mode, the ACPCE adapts to the slowly changing amplifier effects that occur as a function of the age, temperature and operating conditions such as power supply variations. When compared to the direct non-linear pre-equalization structure illustrated in FIG. 29 it can be seen that a significant expansion of the ACPCE's signal processing requirements has occurred. This mode is regarded as the non-linear filtered-input adaption mode and consists of two mutually coupled adaption engines. The motivation for this approach occurs because this embodiment provides increased stability, less adaption jitter, resilience to system noise and rapid adaption rates. The adaption performance is sufficiently rapid that although more signal processing computation is required per iteration than the previously disclosed method, the total number of iterations is actually reduced, which actually results in a lower computation burden for the ACPCE DSP engine.

Figure 30:
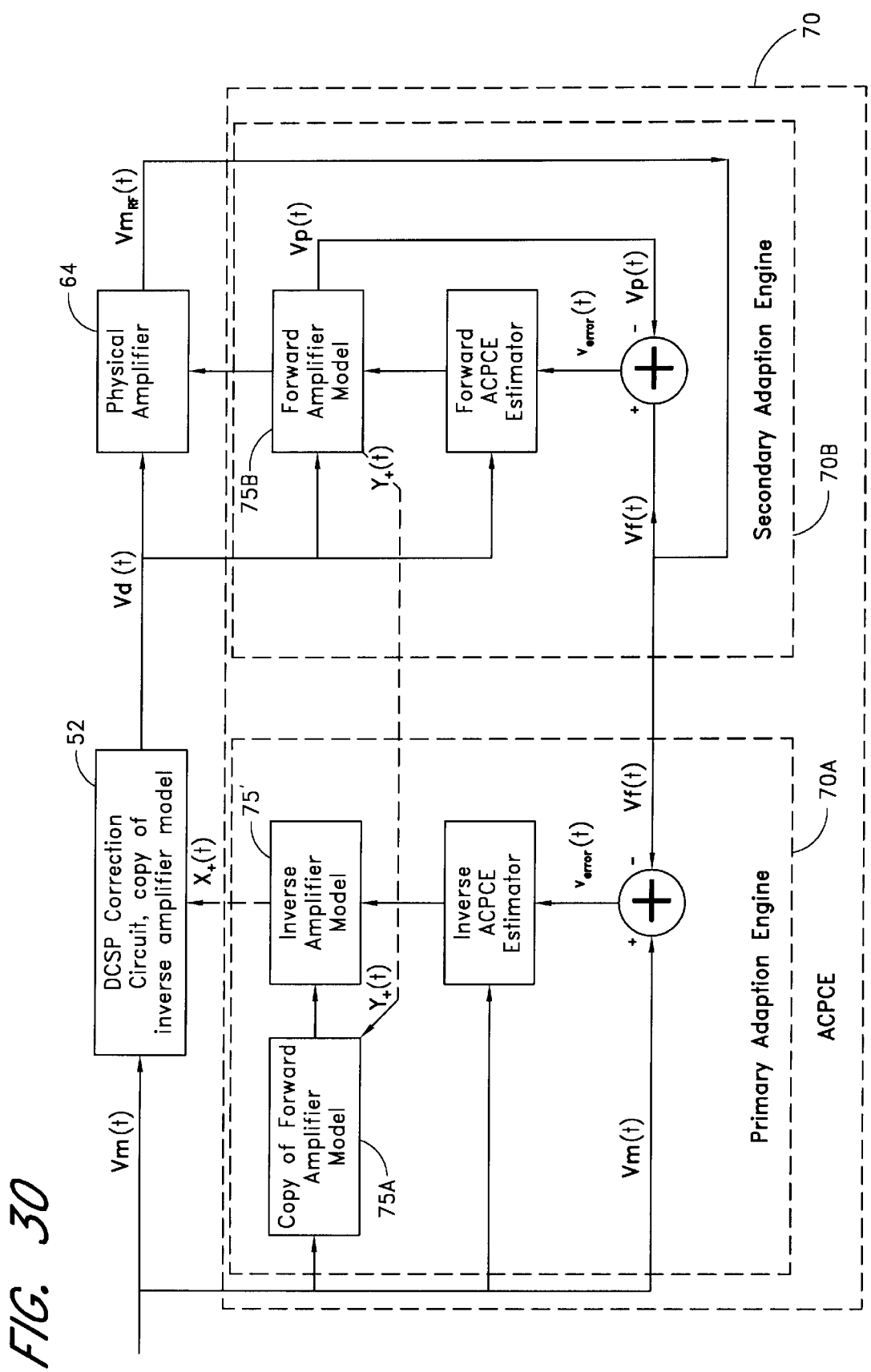

As depicted in FIG. 30, the ACPCE adaption engine's mutually coupled adaption engines consist of a primary engine 70A and a secondary engine 70B. The primary engine comprises a forward amplifier model 75A that is a copy of the amplifier model generated by the secondary loop, an inverse amplifier model 75' that is adapted by the ACPCE's inverse estimator, and a subtraction junction that generates an error signal between the physical amplifier's output signal Vf(t) and the input signal Vm(t). The secondary adaption engine comprises a forward amplifier model 75B that is adapted by the ACPCE's forward estimator, and a subtraction junction that generates an error signal between the physical amplifier's output signal Vf(t) and the forward amplifier model's output signal Vp(t).

The circuit also permits the secondary adaption engine 70B to pass coefficients of the forward amplifier model 75B to the primary adaption engine that utilizes a copy of the forward amplifier model 75A. The primary engine 70A is also permitted to pass updated inverse amplifier model coefficients to the DCSP correction circuit 52. This construction/circuit topology may be implemented within DSP or microprocessor code, or may be encapsulated in ASIC silicon or an FPGA. The inverse estimator and forward estimators may utilize the standard LMS, RLS, block average RLS and Kalman filter algorithms that have been previously disclosed.

The inverse and forward estimators are also utilized to adapt the inverse and forward amplifier models 75', 75B, respectively. These models may utilize any of the non-linear amplifier or predistorter models previously disclosed. That is, the multi-dimensional data structure core previously disclosed is well suited for representing both non-linearities.

The inverse and forward amplifier models are not required to be of equal complexity. For instance, the forward amplifier model 75B could utilize a simple AM-AM and AM-PM function represented by a single dimension data structure indexed by magnitude, while the inverse model 75' could utilize the full multi-dimensional data structure. All indexing and addressing utilized in the forward and inverse amplifier models is computed from a common reference to permit stable adaption between the mutual coupled loops. In this particular implementation, the input signal Vm(t) is utilized for this purpose, although other common signals within the system can be used. Coupling occurs because the secondary loop feeds forward model coefficients back to the primary loop.

FIG. 30 further schematically depicts the application of the filtered-input adaptation algorithm to the predistortion. Compared to the standard pre-equalizer configuration, the filtered-input pre-equalizer configuration adds a forward amplifier model which is simultaneously adapted by the secondary loop to model the unknown distortion generated by the physical power amplifier 64. The resultant forward amplifier model is then employed by the primary adaption engine to precondition or input filter the input source signal Vm(t) so that the adaptation of the inverse amplifier model by the inverse ACPCE estimator for the compensation of the unknown nonlinearity uses this preconditioned signal as input instead of the source signal Vm(t). Other than this modification, the adaptation of the DCSP correction coefficients in the inverse amplifier model 75' proceeds in the scenario as in the previously disclosed pre-equalizer case. In particular, note that the adaptation error, Verror(t), for the inverse amplifier model (DCSP correction coefficients) adaptation is still the difference between the desired input source signal, Vm(t), and the actual observed compensated system output, Vf(t), hence adaptation ceases only when perfect predistortion compensation is achieved. Ordinarily, adaption proceeds by exercising both inverse and forward estimators simultaneously. However, DSP resources can be conserved by alternating adaption of the forward and inverse models on a 50/50 or other duty cycle basis.

4. EXAMPLE HARDWARE IMPLEMENTATIONS

FIG. 31 A illustrates a typical implementation of the wideband predistortion amplifier system 50. Due to the fast signal processing requirements, the DCSP 52 is preferably implemented using dedicated hardware such as a field programmable gate array or dedicated silicon in an ASIC.

Because the ACPCE operates in non-real-time, the ACPCE is preferably implemented using a general purpose DSP or microprocessor 94 such as a TMS320C54/ TMS320C60/TMS320C40/ARM 7 or Motorola 68000 device. This processor 94 is preferably augmented with non-volatile ROM 94A for both program storage and factory installed SID default parameters. Both ROM and Flash ROM are particularly suitable for this purpose. As with most DSP or microprocessor designs, a proportional amount of RAM 94B is used for general purpose program execution.

As depicted in FIG. 31A, the DCSP core 52 has fast access to the compensation parameters which are stored in RAM 96. This RAM structure is also accessible by the ACPCE (processor 94), which provides updated/adapted parameters on a regular basis. The ASIC's RAM 96 or a separate RAM is used to temporarily store the sets of observed amplifier input and output signal sequences used by the ACPCE. Thus it may be identified that the core DCSP process lies within the ASIC core block 98 in FIG. 31A. As digital signal processors evolve in speed, this process may be computed by a processor such as a TMS320C60 from Texas Instruments or a SHARC processor from Analog Devices. However, such processing rates are currently beyond the capabilities of DSPs.

The ASIC or FPGA includes a modest amount of 'glue logic' 100 to interface the DCSP to the microprocessor or DSP 94. Future evolution of the design will permit the DSP/microprocessor core 94 and the ASIC/FPGA to be integrated onto a single ASIC chip, as shown by the dashed border in FIG. 31A. ARM7, TEAK, OAK and ARC DSP and microprocessor cores are particularly suited to this approach and will yield a one chip solution if on board RAM, ROM and Flash ROM are provided.

The implementation shown in FIG. 31 A uses direct conversion upconversion (block 58) combined with RF to IF downconversion. (block 66). The output of the downconversion block 66 is appropriately sampled by the ADC 68 to capture IF data, and is then converted to complex baseband by digital quadrature conversion circuitry (not shown). To those skilled in the art it is readily apparent that this embodiment could readily use direct conversion for both RF up and downconversion or use digital to IF conversion followed by IF to RF and vice versa for the frequency translation process.

FIG. 31B illustrates an alternate RF-in/RF-out embodiment that may be used if a digital baseband data source is not available. Naturally the core DCSP and ACPCE processes are identical with a few minor modifications to accommodate the imperfections of the input downconversion process and the digital drive circuitry.

5. VARIATIONS, ENHANCEMENTS AND APPLICATIONS

This section details several example variations, enhancements and applications of the predistortion architecture and methods set forth above.

Figure 32:
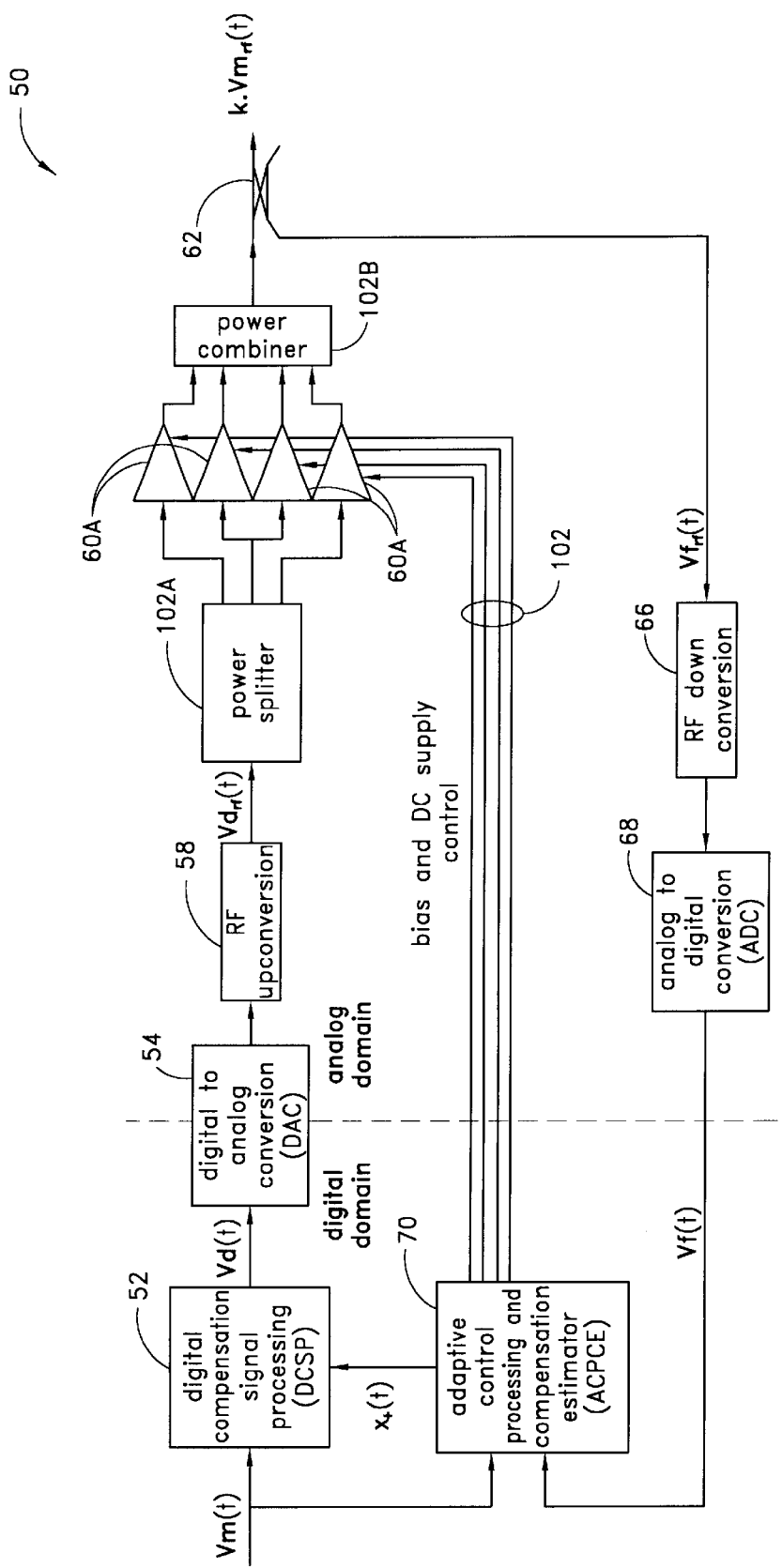
FIG. 32 illustrates an embodiment in which the individual nonlinear amplifiers are separately controlled.

5.1. Control of Multiple Amplifiers in a Predistorter for Maximizing Power Efficiency FIG. 32 illustrates an embodiment that may be employed in CDMA third generation cellular systems which use a multicarrier-multibearer airlink structure. The amplification chain 64 in this embodiment includes a power splitter 102A that divides the predistorted RF signal into multiple components, an array of nonlinear amplifiers 60A which each amplify a respective component signal, and a power combiner 102B that combines the amplified signals.

By way of background, in periods of high calling rates, the amplifier system may be required to support in excess of 64 users for which each user signal is multiplexed onto a shared RF carrier. Each user may require up to 4 watts of RF power, so the aggregate peak power of the amplifier may readily exceed 256 watts. In practice such power levels are generated by employing multiple power amplifier modules, as depicted in FIG. 32. During periods of low traffic activity, i.e., a low number of active users, the power amplifier 60 would normally consume excess DC power which is dissipated and wasted as heat energy. This occurs because each power amplifier module 60A consumes quiescent current even when the amplifier is provided without an input signal.

In accordance with one aspect of the invention, this wasted energy is eliminated or significantly reduced by utilizing the ACPCE 70, or another control module, to observe the drop in input signal level associated with low traffic conditions and turn on and off specific amplifier modules 60A. The amplifier modules 60A are switched on and off such that the resulting peak power capability of the amplifier assembly 60 is just sufficient to service the observed traffic load. This permits significant savings in power utilization and hence increases system efficiency. Alternatively, the base station in which the amplifier system is used may command the ACPCE directly to the optimum peak power capability.

The individual amplifiers 60A are preferably controlled through direct bias and DC power supply control lines 102. Alternatively, variable power supply and bias controls can be used that manipulate the amplifier 60A to intermediate operating points.

Although this strategy of separately controlling the individual amplifiers 60A can be exploited without the utilization of the wideband predistortion concept, the overall linearity performance of the combination offers significant advantages. Primarily, as each amplifier module 60A is turned on or off (or otherwise varied in operating point), the composite nonlinearity of the entire amplifier assembly 60 rapidly changes. The ACPCE and DCSP immediately compensate for these rapid changes, avoiding the degradation in system linearity and increase in spectral regrowth that would otherwise occur.

The ACPCE can store or generate separate DCSP compensation parameters for each of the possible operating states associated with the manipulation of the amplifier operating points. This may be-accomplished, for example, by adding an additional dimension to the multi-dimensional data structure 52H that corresponds to such states, and by using the current state as an additional index for retrieving parameters from the data structure. To provide a simple example, if the amplifier 60 contains two non-linear amplifiers 60A that can assume the operational states ON/ON, ON/OFF, and OFF/ON only, a total of three levels would preferably be added to the multi-dimensional data structure 52H along the new dimension.

An important artifact of this multi-amplifier control strategy is that the DCSP coefficients should reflect a gain increase or decrease to compensate for the change in average power that occurs when an amplifier module's state is changed. In practice this is straightforward since the DCSP coefficients maintain the overall loop gain at a constant value despite the reduction in maximum peak power capability.

Figure 33B:
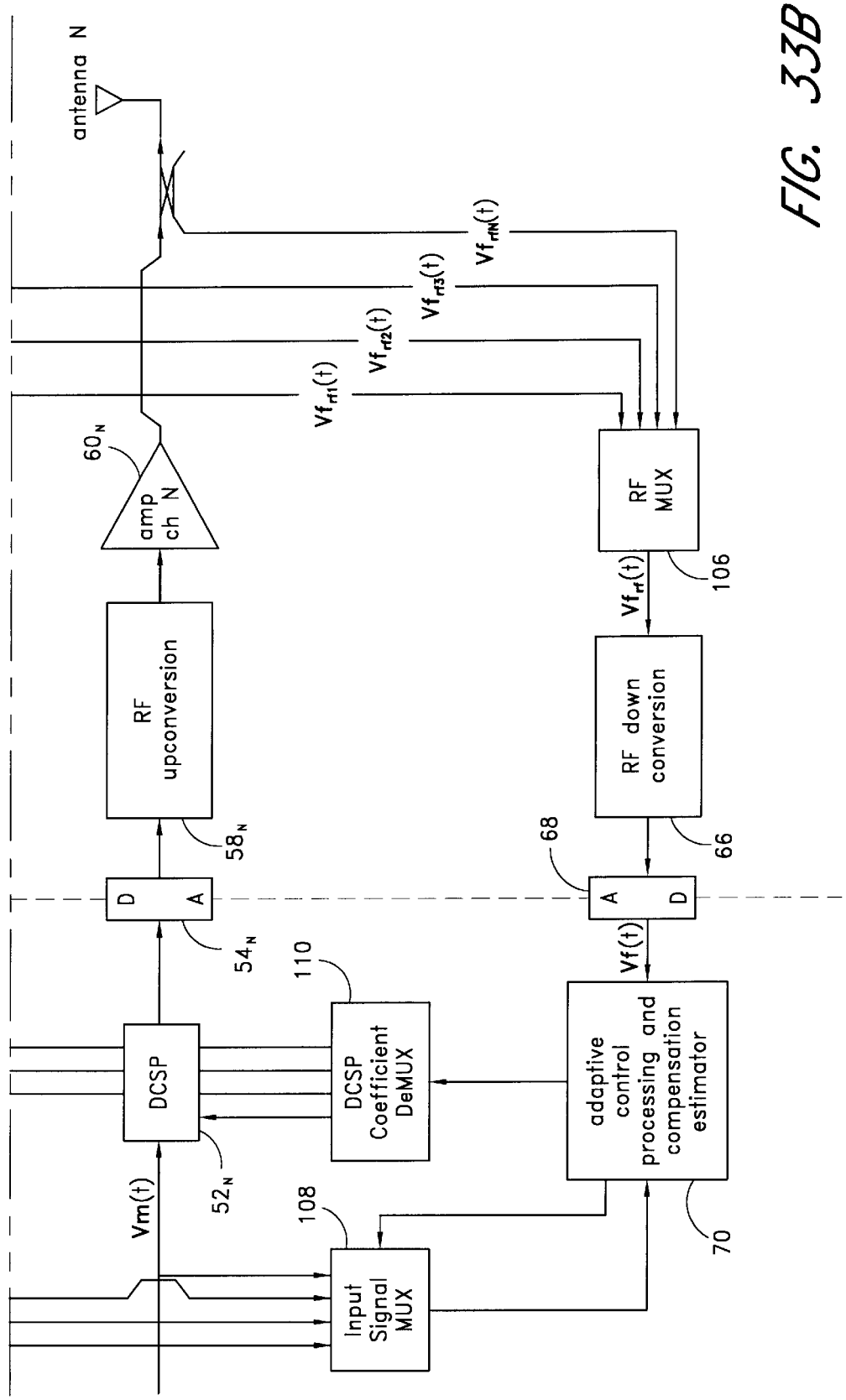
FIG. 33, which consists of FIGS. 33A and 33B, illustrates an embodiment in which input signals are predistorted along each amplification path of an antenna array system using a single ACPCE.

5.2. Control of Multiple Independent Amplifiers for Antenna Array Applications FIG. 33A illustrates how the predistortion architecture may be employed in a transmission antenna array system 50. The use of antenna arrays is referenced in the design of third generation cellular systems such as W-CDMA and CDMA-2000 for the purpose of maximizing system capacity via space division multiple access, beamforming, null steering, interference and space-time processing techniques. All of these techniques generally require linear independent power amplification of each signal fed to each antenna.

The predistortion architecture as described above can be applied directly to each antenna section independently; however, such an approach is costly because excess components and physical space are required. Because the nonlinear power amplifier's characteristics change very slowly as a function of temperature, aging and mechanical stress, it is feasible to use a single ACPCE which computes updated parameters for multiple DCSP compensation circuits $52_1$–$52_N$ on a time shared basis. This permits significant reductions in the number of components used because only one DSP or microprocessor is required to service all the amplifiers $60_{1-N}$. Furthermore, only a single RF to baseband downconverter 66 is required because the ACPCE can control an RF multiplexer 106 which is set to observe only the output of the amplifier that is being controlled at a particular instant. An input signal multiplexer 108 may similarly be provided so that ACPCE and select a particular input signal $Vm_1(t)$–$Vm_N(t)$ to sample. In addition, a demultiplexer 110 allows the ACPCE to select a particular destination DCSP $52_{1-N}$ from the group.

Figure 34B:
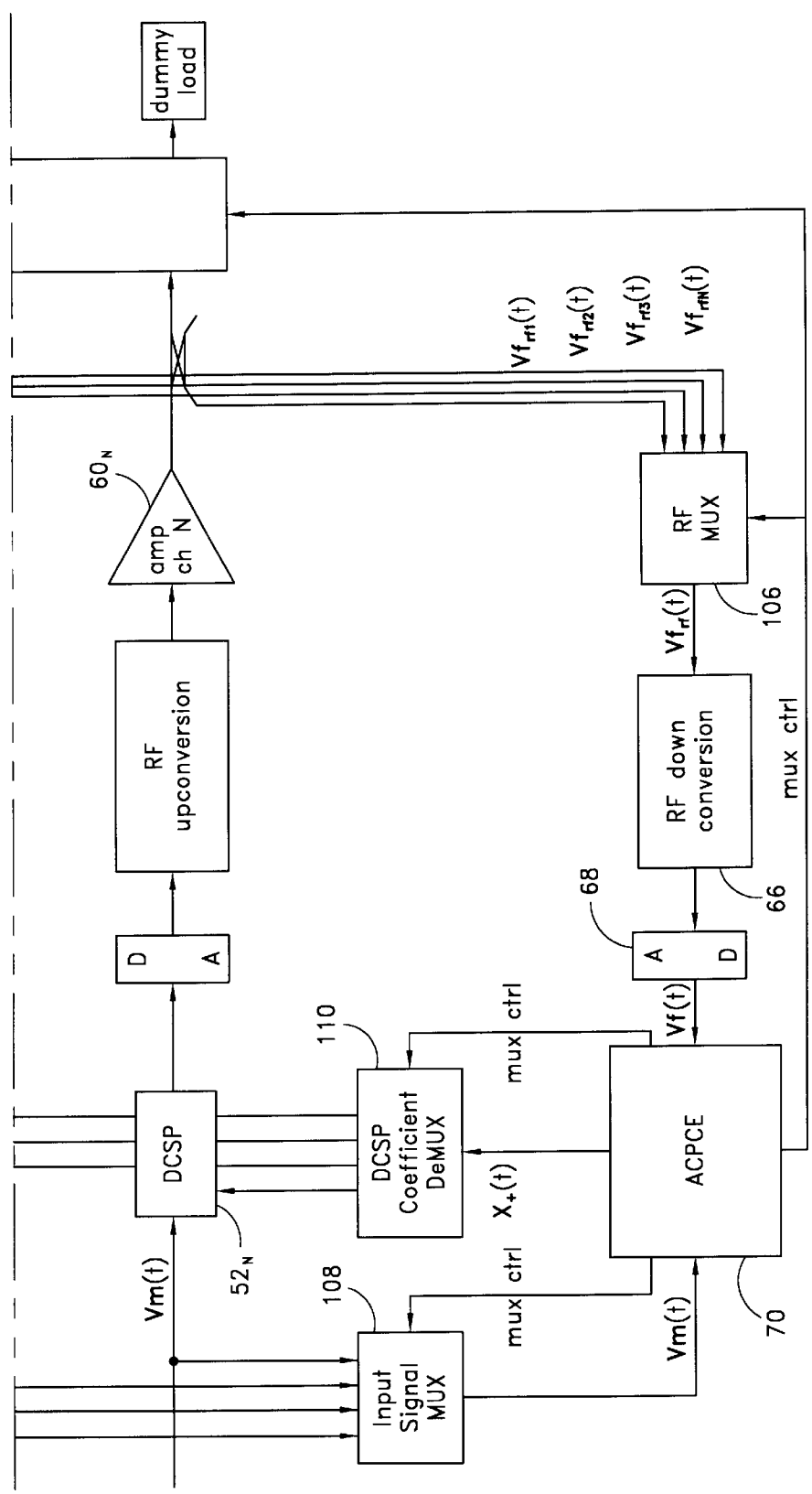
FIG. 34 illustrates an architecture for controlling multiple independent amplifiers for hot swap redundant applications.

5.3. Control of Multiple Independent Amplifiers for Hot Swap Redundant Applications FIG. 34 illustrates how the predistortion architecture may be employed in a hot swap redundant power amplifier assembly. Redundant hot swap amplifier assemblies are frequently utilized in cellular systems, and will be a prime requirement in multicarrier-multibearer systems such as W-CDMA and CDMA-2000 cellular systems. Redundant designs ensure that call availability is not compromised. This requires each amplifier assembly to support redundant amplifiers that are continually stimulated with a drive signal but with the generated power dumped in a dummy load. Should an amplifier fail or degrade in performance beyond the control of the predistortion system, the ACPCE can readily switch input signal streams and RF routing networks to ensure that the redundant amplifier is used while the failing amplifier is taken out of operation.

Since the non-linear power amplifier's characteristics change very slowly as a function of temperature, aging and mechanical stress, it is feasible to utilize a single ACPCE which computes updated parameters for multiple DCSP compensation circuits $52_{1-N}$ as described above. This permits significant reductions in the number of components because only one DSP or microprocessor is required to service all the amplifiers $60_{1-N}$. Furthermore, only a single RF-to-baseband downconvertor 66 is required because the ACPCE can control an RF multiplexer 106 which is set to observe only the output of the amplifier that is being controlled at a particular instant. The approach is further augmented by providing the data pathways with multiplexers 108, 110 so that the associated input signal and appropriate destination DCSP can be accessed by the ACPCE.

5.4. Signal Pre-conditioning Algorithms

The predistortion architecture described above also permit an amplifier system to be created which exhibits a perfect or near-perfect linear response up to the nonlinear amplifier's maximum output power. If the input signal is appropriately scaled such that its maximum input amplitude/power corresponds to the amplifier's maximum output power, then the power spectral density of the amplifier's output signal will be the same as that of the input signal. This permits a system designer the freedom to use spectral (radio) resources in an aggressive manner in an effort to maximize system capacity.

Figure 35:
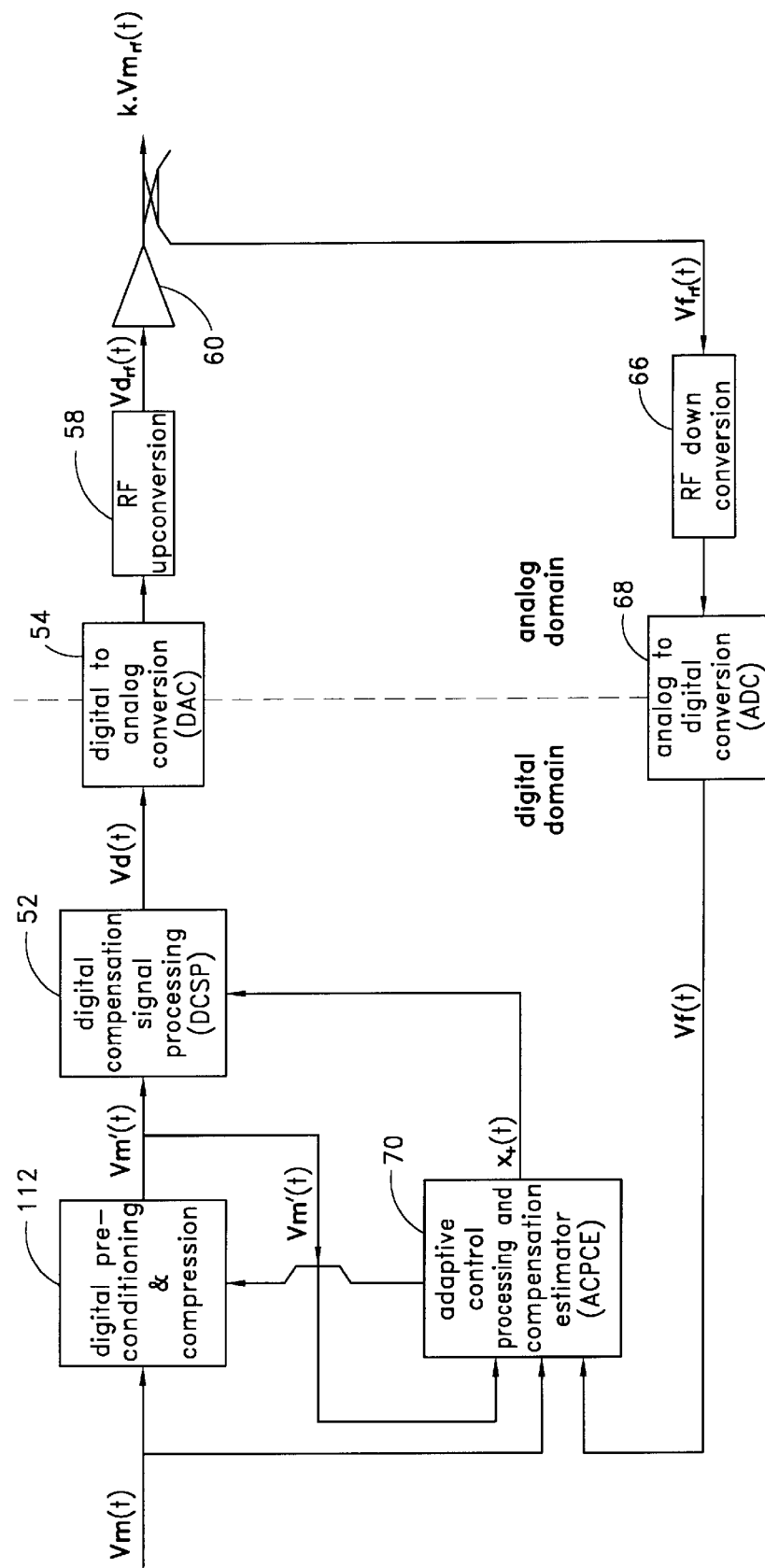
FIG. 35 illustrates an embodiment which uses digital pre-conditioning and compression of the input signal.

In third generation CDMA systems, the amplifier is commonly employed to amplify signals with a very high peak-to-average ratio, typically greater than 12 dB. In such scenarios, the average output power of the amplifier is 12 dB lower than the maximum power of the amplifier and, as a consequence, amplifier efficiency is significantly reduced. As depicted in FIG. 35, system power efficiency may be increased in such scenarios by adding a signal pre-conditioning and compression circuit 112 to the architecture of FIG. 1.

The circuit 112 operates by deliberately manipulating the amplitude probability density function of the input signal waveform so that the peak-to-average ratio of the waveform is significantly lower than that of the original input waveform. This manipulation forces spectral regrowth to occur, which immediately undermines the original purpose of linearizing the amplifier. However, because the signal manipulation occurs in the digital domain, the spectral regrowth levels can be precisely controlled from amplifier to amplifier without allowing for manufacturing margin. Furthermore, because the digital pre-conditioning and compression circuit acts upon a digital signal, the process can utilize amplitude-only distortion which can be controlled in a very benign manner.

Figure 36:
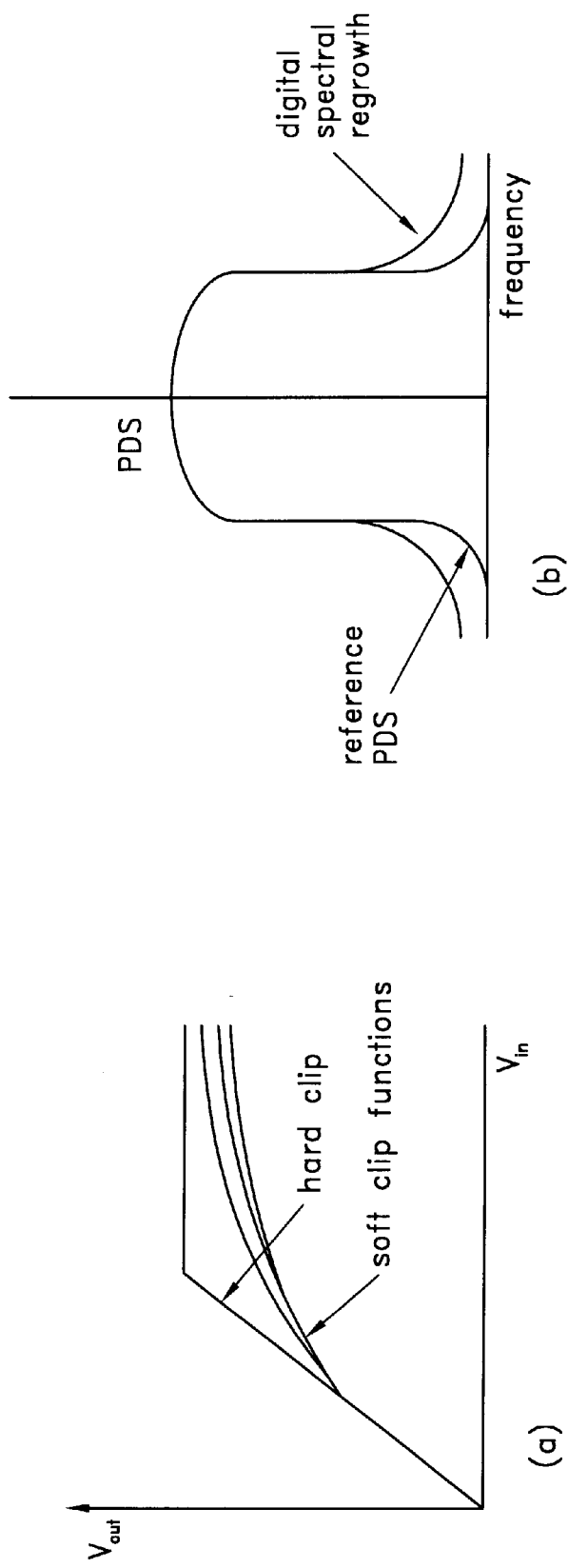
FIG. 36, which consists of FIG. 36(a) and 36(b), illustrates pre-conditioning compression functions and their effect on power spectral density.

As illustrated in FIG. 36(a), a family of soft predistortion functions may be used as well as deliberate overdriving of the amplifier so that a hard digital clipping function is used. FIG. 36(b) illustrates the impact of the pre-conditioning and compression circuit upon the power spectral density of the applied waveform or input signal.

An important feature of the digital pre-conditioning and compression circuit 112 in a preferred embodiment is that the system operator or designer can set an effective digital operating point that trades amplifier efficiency against the level of spectral re-growth. Thus, a direct relation between system capacity and amplifier linearity and efficiency may be established. In lightly loaded networks, more spectral regrowth and distortion products may be tolerated in favor of higher amplifier efficiencies. In highly used networks where system interference limits system capacity, amplifier efficiency may be degraded ensuring minimum spectral re-growth occurs. This luxury is permitted primarily because of the extreme repeatability of digital circuits.

Equation 30 defines a family of soft compression functions which only invoke AM-AM distortion in the input signal. The equation has parameters $\alpha$ and $\beta$ which correspond to the degree of non-linearity invoked and maximum input power.

$$Vm(t) = \frac{|Vm(t)|}{\left(1 + \left(\frac{|Vm(t)|}{\beta}\right)^\alpha\right)^{1/\alpha}} e^{j(\arg(Vm(t)))} \qquad \text{Equation 30}$$

Clearly, as $\alpha$ increases the amplifier's efficiency increases with an associated increase in spectral regrowth. Manipulation of $\beta$ permits a hard clipping level to set. Equation 30 is disclosed as an exemplary function providing a non-linear pre-conditioning and pre-compression function. In practice, any function or non-linear equation that exhibits behavior that incurs desirable changes in the waveform may be employed. It is not unreasonable to imagine that deliberate insertion of AM-PM may, on occasion, be an attribute requiring an alternate function.

The DCSP compensation parameters should be computed and adaptively adjusted assuming that the output of the pre-conditioning circuit 112 is the input signal to the amplifier. In an enhanced version of this concept, the ACPCE monitors the incoming signal statistics and adaptively adjusts $\alpha$ and $\beta$ to meet a predetermined range of efficiency and distortion operating conditions as traffic and signal statistics change. This is illustrated in FIG. 35.

5.4.1. Implementations Modes

FIG. 35, discussed above, illustrates a circuit topology that would permit the inclusion of signal pre-compression/pre-conditioning signal processing to be readily utilized in conjunction with the digital predistortion architecture. A practical design would be to construct the circuit using a simple non-linear hardware function constructed from a set of multipliers and coefficients that provide a polynomial representation of the pre-conditioning/pre-conditioning function. Such a design is illustrated in FIG. 37.

Figure 37:
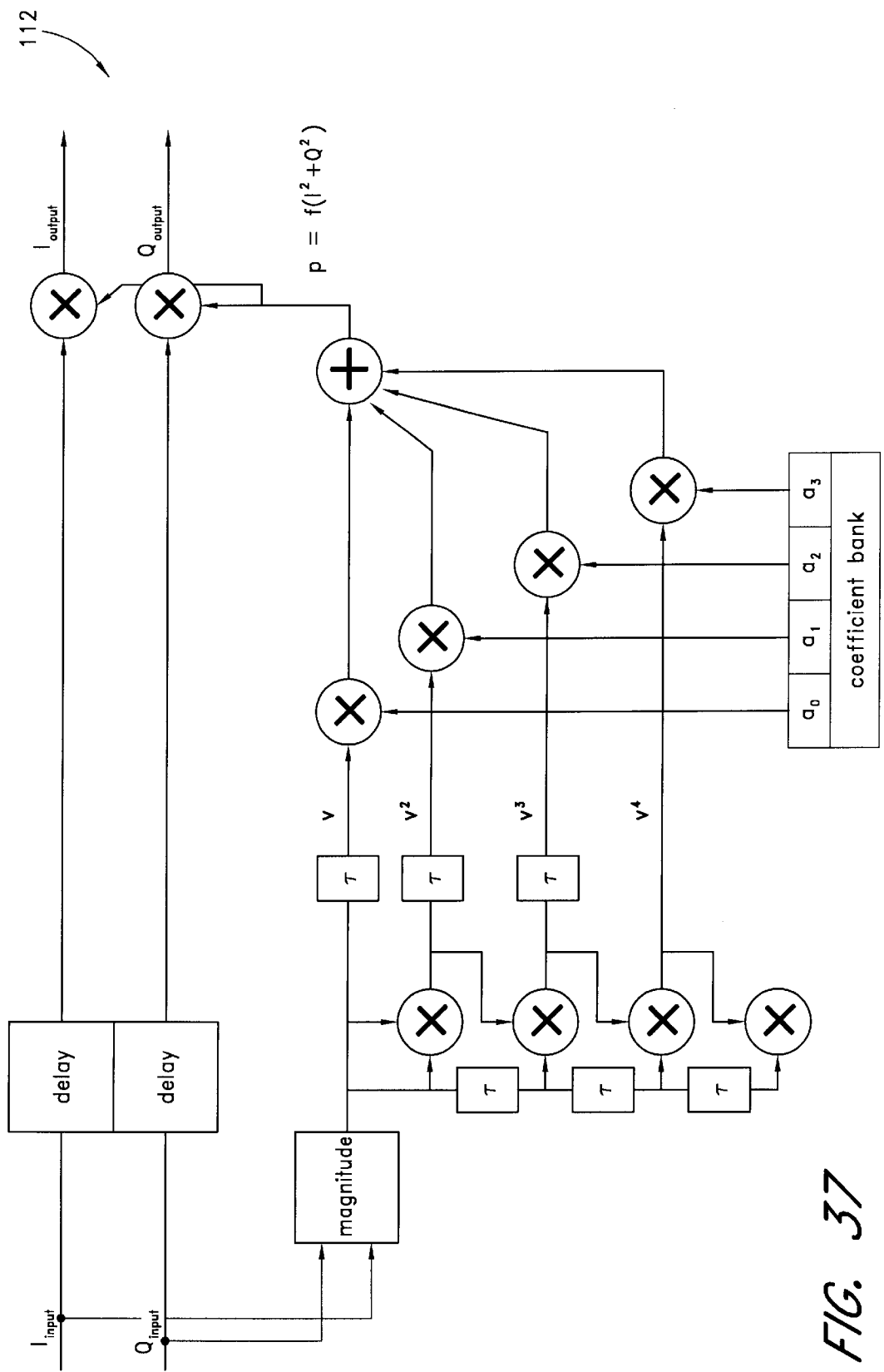
FIG. 37 illustrates a hardware implementation of the digital pre-conditioning and compression block in FIG. 35.

As illustrated in FIG. 37, the pre-conditioning/pre-compression function of Equation 30 has been effectively implemented as a hardware representation 112 of the Taylor series expansion of the function. This approach uses extensive delay balancing between each of the signal processing paths to ensure that the pre-conditioning function p applied to the input waveform corresponds correctly to the input signal samples. This approach is burdened with three engineering compromises: (1) delay latency through the circuit is increased as a function of the order of the Taylor series, i.e. the number of multipliers stages, (2) the power consumption increases as the number of multipliers is increased and (3) the pre-conditioning/pre-compression function can only be approximated if only a few low order terms of the Taylor series are exploited. Naturally, for slower rate applications where general purpose DSP and microprocessors are utilized to embody the design, software instructions can be used to calculate the pre-conditioning/pre-compression function directly or as a Taylor series expansion equivalent.

Figure 38:
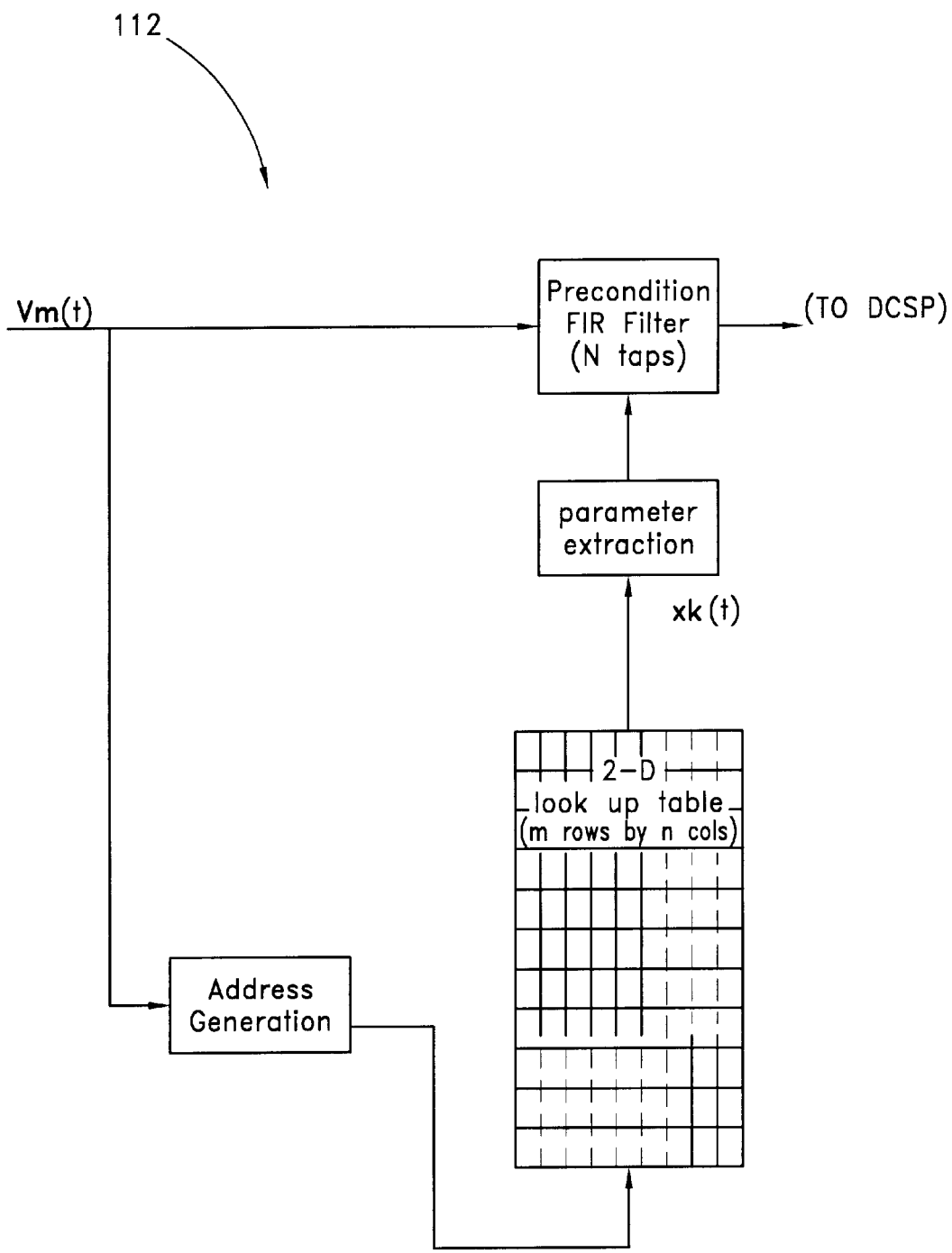
FIG. 38 illustrates an alternative implementation of the digital pre-conditioning and compression block in FIG. 35.

An alternate design to obviate the increase in latency is to realize that the basic multidimensional predistortion data structure 52 can be utilized to build a pre-conditioning/pre-compression system. This approach does not sacrifice pre-conditioning function accuracy. This design 112 is illustrated FIG. 38.

The design illustrated in FIG. 37 can be implemented in software running on a DSP, but for wideband applications, the design is preferably implemented within a circuit of an FPGA, ASIC, or other automated hardware device. Since the ACPCE can be utilized to capture the input signal stream or the pre-conditioned input signal stream, operation of the predistortion and pre-conditioning circuits can proceed as normal because the ACPCE will be provisioned with software copies of the entire structure that it is controlling. In practice, the extensive capabilities of these cascade non-linear functions exceeds the necessities of typical pre-conditioning/pre-compression functions. This permits the pre-conditioning/pre-compression multi-dimensional data structure to be reduced to a single dimension, indexed by the input signal magnitude, and furthermore, store only a single pre-conditioning coefficient that is multiplied with the input signal data. That is, the pre-conditioning filter reduces to a single tap FIR filter.

Although, the above design approach reduces the latency and power consumption of the previous pre-conditioning/pre-compression circuit 112 it still consumes a finite level of power which is dissipated as heat. Furthermore, the latency is, still, also finite. The design also requires a finite amount of resources in, e.g., ASIC/FPGA gates or software instructions and memory. However, the advantage of the approach is that the accuracy of the pre-conditioning/pre-compression function is not compromised, whilst the multidimensional data structure does permit arbitrary functions to be utilized.

Figure 39A:
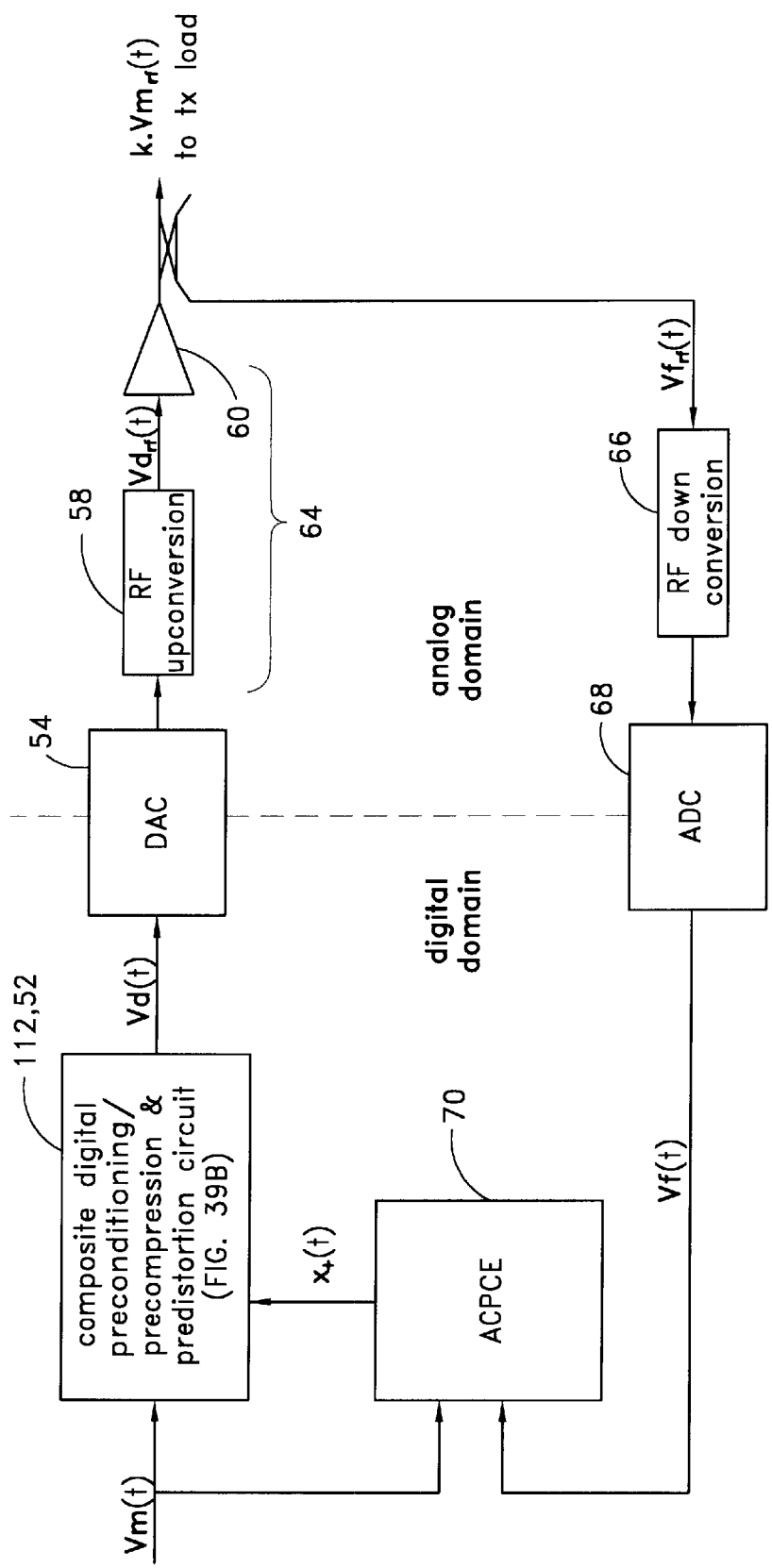
FIG. 39 illustrates a composite implementation of the digital pre-conditioning/compression and DCSP blocks of FIG. 35.
Figure 39B:
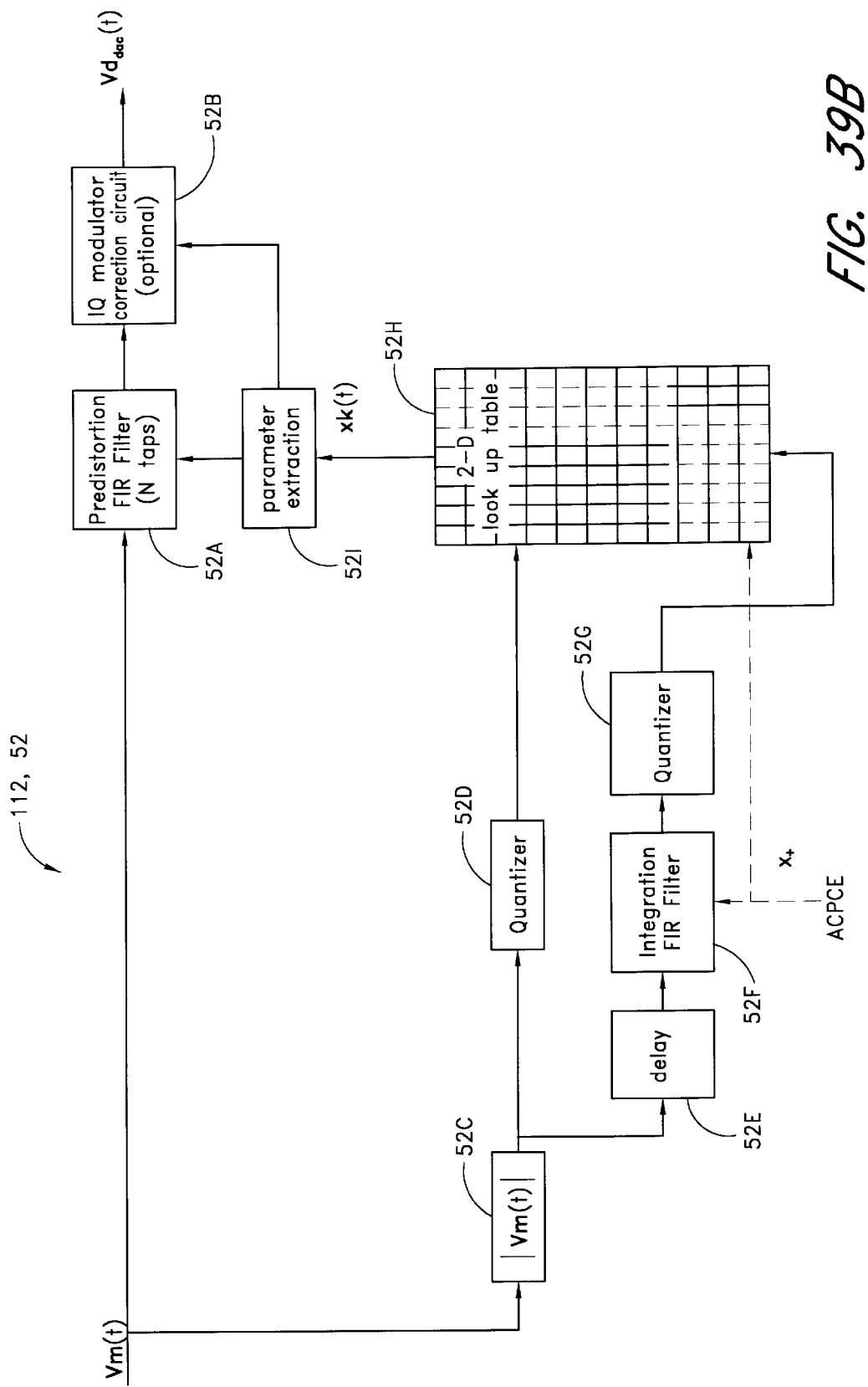

The multi-dimensional data structure design approach (FIG. 38) for the pre-conditioning/pre-compression circuit 112 does, however, provide impetus for a superior design. Recall that the basic premise of the predistortion approach is to cascade two non-linearities to reproduce a specific response, typically a linear overall transfer function. The introduction of the pre-conditioning/pre-compression circuit 112 into the design results in the cascading of three non-linearities to achieve a new overall response. However, since the parameters that define the two digital baseband signal processing non-linearities are defined explicitly by the ACPCE, there is no reason why the pre-conditioning and pre-compensation non-linearities cannot be combined into one single complex baseband non-linearity. This new linearity will be furnished with coefficients that would replicate the processing that would be invoked by the two cascaded non-linearities. This approach is illustrated in FIG. 39.

It will be noticed that the composite circuit, which implements both the pre-conditioning/pre-compression circuit and the DCSP, is identical in structure to the multi-dimensional predistorter (DCSP) design 52 disclosed above; however, the calculation of the numerical coefficients stored in the multi-dimensional data structure 52H by the ACPCE will now exhibit different values. These values are computed such that the cascaded/composite response of the pre-distortion and pre-conditioning/pre-compression functions is realized. This approach is preferred because no additional system latency, power consumption or functional representation accuracy impairments are incurred. Furthermore, in practical fixed point mathematical implementations, no additional quantization noise due to numerical rounding is incurred. This approach thus allows smaller and more power efficient predistortion designs with low latency to be produced.

Figure 40:
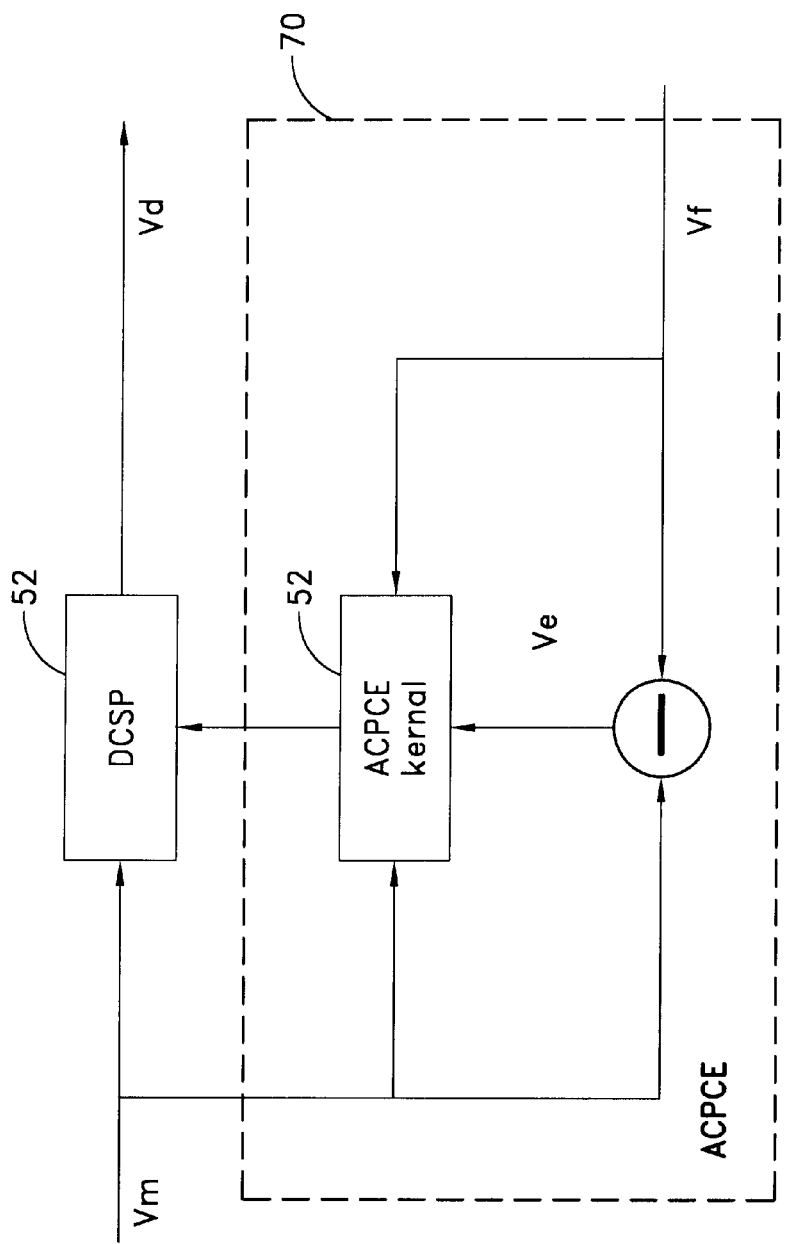
FIG. 40 illustrates a process flow with no signal pre-conditioning.
Figure 41:
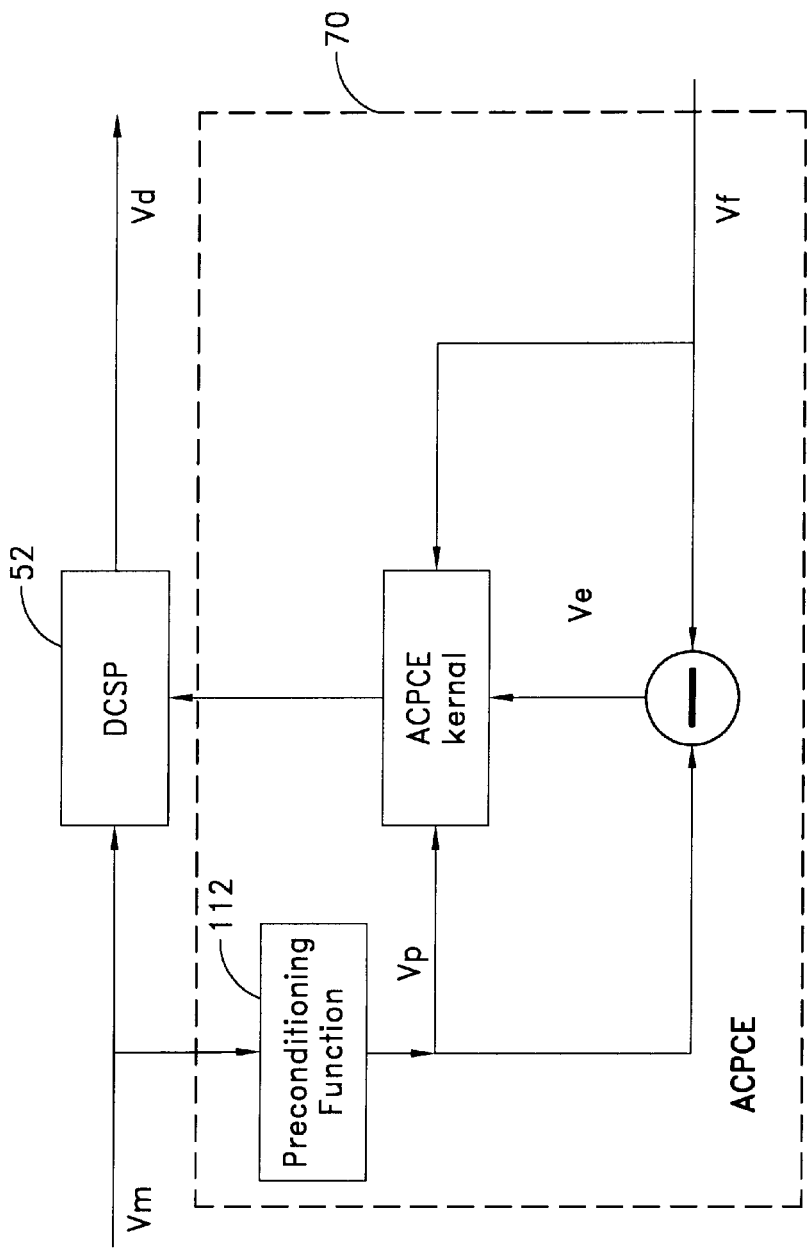
FIGS. 41 and 42 illustrate process flows with signal preconditioning.

5.4.2. Adaptive Computation and Modeling for the Composite Pre-condition/Pre-compression and Predistortion System by the ACPCE The adaption and computation of the DCSP's coefficients when operating in the cascaded pre-conditioning and pre-distortion mode precedes as shown in FIG. 41. As illustrated in FIG. 40, in the normal predistortion mode (no pre-conditioning), the ACPCE would ordinarily capture the input signal Vm(t) and the observed output of the amplifier Vf(t) sample sequences. These captured sequences would be processed in non-real time to form the error sequence Ve(t) by subtracting the time, phase and gain aligned sequences Vm(t) and Vf(t). These three sequences would then be processed by the ACPCE to compute, in an adaptive manner, DCSP coefficients that could be downloaded to the DCSP. The repetition of this process results in a set of DCSP coefficients that causes the error sequence to converge to the noise floor of the system, i.e., the error free condition.

As illustrated in FIG. 41, introduction of a preconditioning non-linearity is readily achieved by first modifying the captured input signal sequence Vm(t) by the pre-conditioning function 112. This will then force the ACPCE to compute DCSP coefficients that eliminate the error between the output of the amplifier and the output of the pre-conditioning circuit 112. Naturally, the ACPCE can pre-process the captured input signal, Vm(t), to form Vp(t) in a non real time manner. Thus, this simple extension to the basic ACPCE signal processing algorithms permits the cascade of three non-linearities (pre-conditioning, predistortion and the amplifier) and the adaption of the center non-linearity (and potentially first non-linearity, if required).

Direct application of the above approach will cause a failure in the system to converge. The convergence failure can easily be identified and appropriate simple correction steps taken. The convergence failure occurs because the hardware (or software implementation) of the DCSP is operating in real time and utilizes the input signal Vm(t) to compute the indexes/address values into the multi-dimensional data structure, while the non-real-time ACPCE, if a literal interpretation of the proceeding argument is adopted, would utilize Vp(t) as the input signal to the entire adaption process. The disconnect occurs because the DCSP would utilize Vm(t) to generate indices while the ACPCE would utilize Vp(t). This disconnect between the real time process and the non-real-time adaptive process is easily eliminated if slight changes are taken, as portrayed in FIG. 42.

Figure 42:
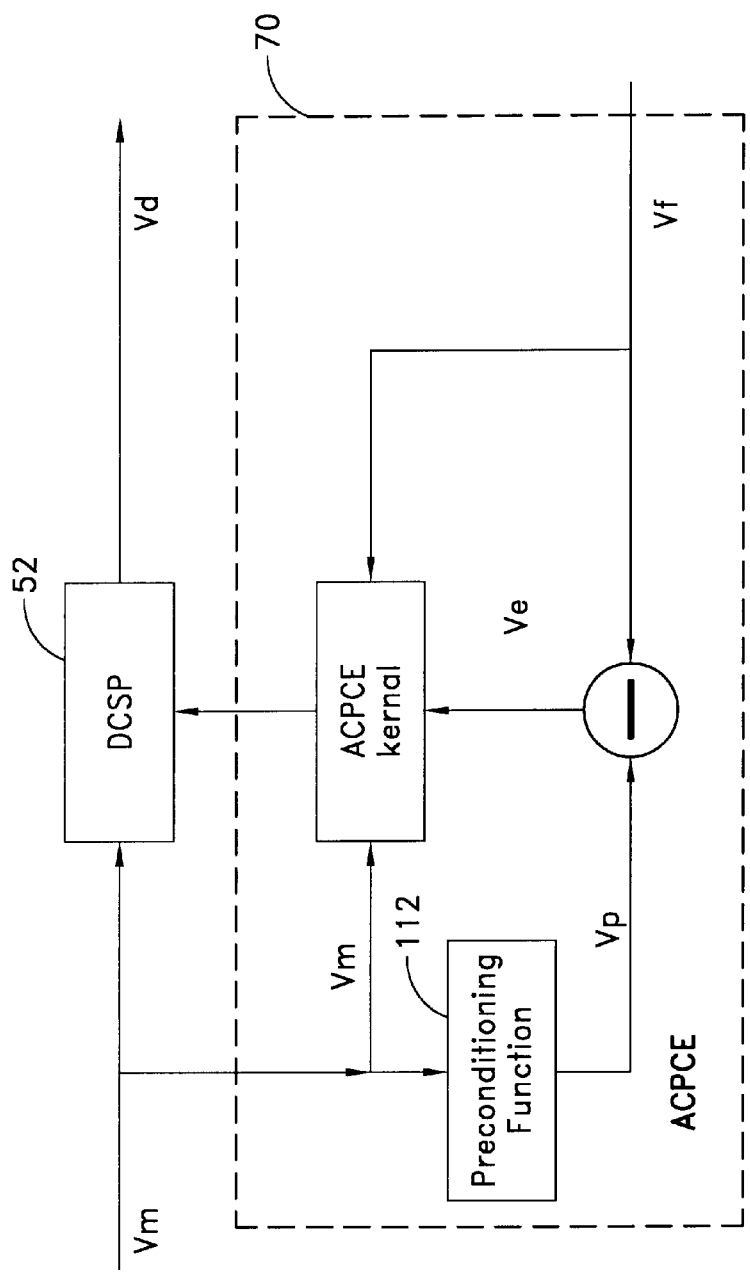

As illustrated by the modified process flow of FIG. 42, the ACPCE utilizes Vm(t) to generate all index/address values computed as a function of the instantaneous and past properties of the input waveform employed to address the multi-dimensional data structure. However, Vm(t) is pre-conditioned to form Vp(t), which is utilized to generate the error function. This forces the ACPCE to compute DCSP coefficients that generate the desired system response from the cascade of non-linearities. This occurs because Ve(t) is still reduced to a zero mean error condition by adaptively adjusting the DCSP coefficients.

5.5. Table Updating Techniques

Figure 43:
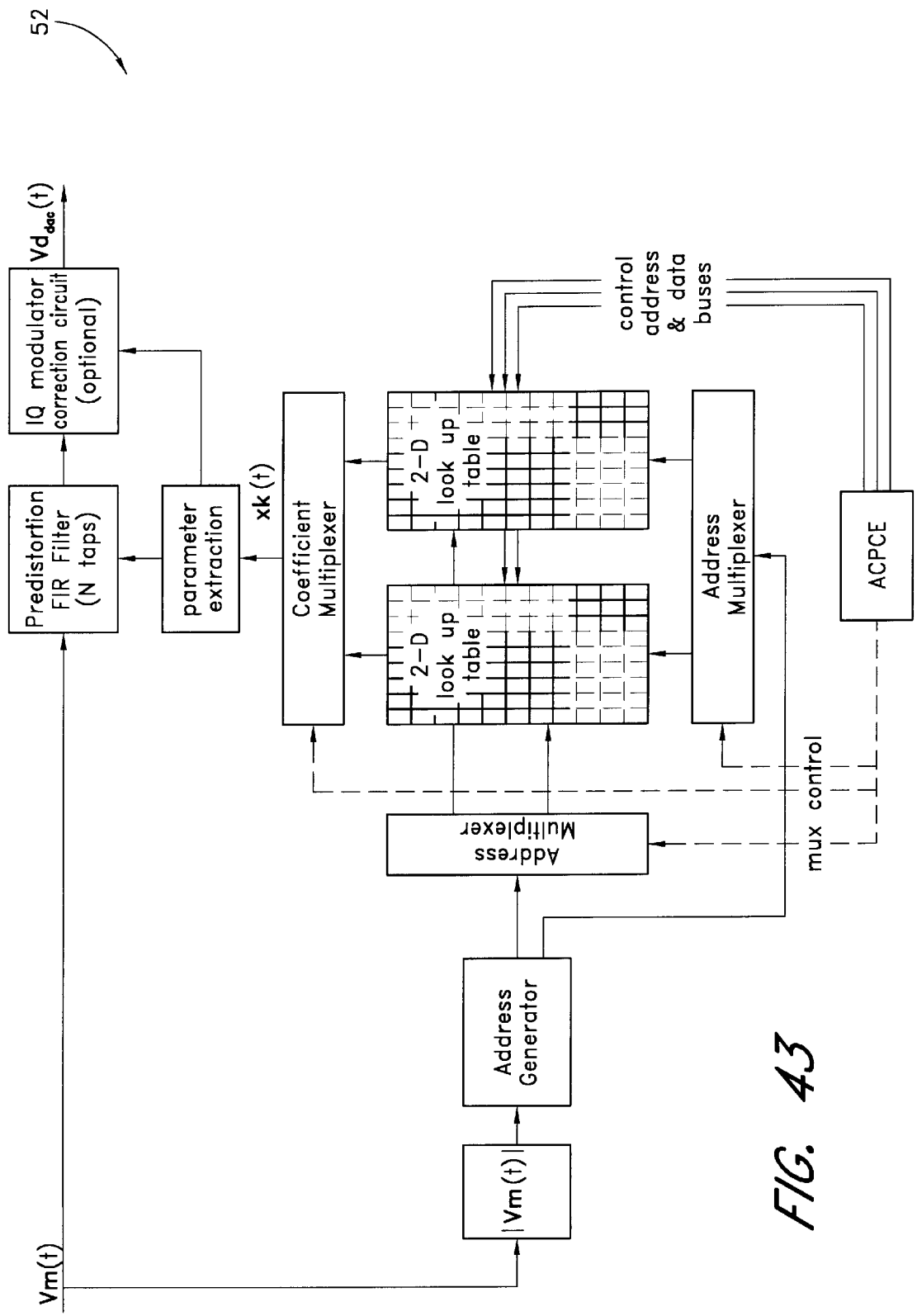
FIGS. 43 and 44 illustrate respective DCSP circuits for updating the multi-dimensional data structure.

A practical implementation of the DCSP 52 would be to provide a design in which two copies of the multi-dimensional data structure 52H are provided within the DCSP furnished from equal amount of random access memory. If a silicon ASIC or FPGA is utilized to implement the DCSP, the multi-dimensional data structure can easily be embedded within the core chip structure. The dual implementation approach permits the real time operations of the DCSP to proceed unabated while the ACPCE downloads update sets of correction coefficient parameters to the second and temporarily redundant copy of the data structure. Once the ACPCE has provided a complete update to the second data structure it may command the DCSP via a simple binary register, or select/set an appropriate switch, to release the first instantiation of the multi-dimensional data structure and to adopt the second copy as the current working multi-dimensional data structure. Thus new coefficients can be utilized with a seamless transition causing no disruption to the predistortion function being imposed upon the input signal. Naturally, each iteration of the ACPCE's adaptive processing provides a new set of correction coefficient parameters which are computed and stored in the 'free' multi-dimensional data structure. Once the full set has been downloaded to the multi-dimensional data structure, the ACPCE instructs the DCSP to swap data structures. Continuous operation causes this process to inexorably repeat. FIG. 43 illustrates this basic design approach.

If this design approach is taken, the amount of memory utilized by the entire design will equate to three times that required for a single copy of the multi-dimensional data structure 52H. Two copies will be used by the real time DCSP processing engine while the ACPCE may potentially utilize its own local copy populated with the most current correction coefficient values. However, the ACPCE could potentially, in some designs, utilize the DCSP's latest copy. A disadvantage to this approach is that the DCSP has two full copies of the multi-dimensional data structure 52H, causing the power consumption to rise. Further, if the design is instantiated in an ASIC or FPGA, the die sizes will significantly increase due to the doubling of the memory requirements. These two factors result in a more expensive product because thermal management of the excess heat requires more expensive packaging, while increased die size results in lower yields at the foundry which also cause cost increases.

These disadvantages can potentially be overcome by employing dual port RAM which permits two external devices to read and write to the memory at the same time. However, the internal dual port RAM actually delays either the read command until the write command is complete, or vice versa, in the advent of timing contention. Since the DCSP preferably operates on a clock cycle by clock cycle basis without any interruption of the flow of correction coefficients (that are provided on a sample by sample basis), dual port RAM is not appropriate unless the device is over clocked (e.g., by a 2× factor). Because overclocking increases power consumption, it is not preferred unless possibly the overall clock speed of the application is quite slow.

Figure 44:
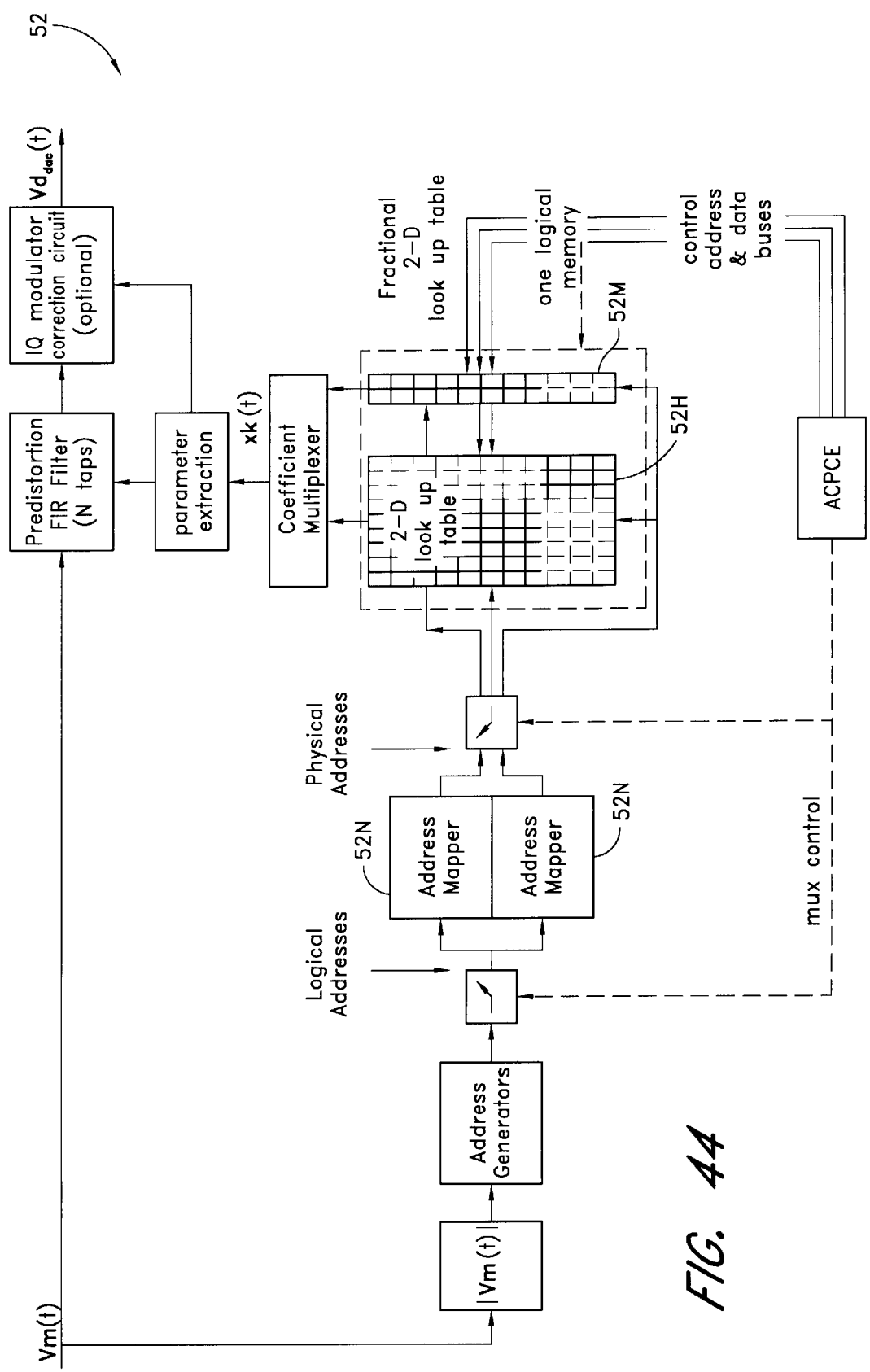

FIG. 44 illustrates a preferred multi-dimensional data structure design that overcomes the deficiencies described above, including providing reduced silicon area and power consumption. The DCSP 52 comprises a single, full, multi-dimensional data structure 52H augmented with an additional fraction or segment 52M of a multi-dimensional data structure. This segment 52M may, for example, constitute merely $\frac{1}{128}$ of the full entity 52H. This segment is utilized by the ACPCE to download a fraction of the new correction coefficients, such that when instructed, the DCSP address mapper will now use this newly updated segment while releasing an old segment for the ACPCE. The address mappers operate in a similar manner to the previous design (FIG. 43) in that two copies are present in the DCSP, and the ACPCE toggles or selects which one should be used.

After new coefficients are downloaded to the multi-dimensional data structure segment 52M, the ACPCE re-programs the 'free' address mapper 52N with an address map that now includes the new segment while releasing the replaced multi-dimensional data structure segment for further updating with new coefficients. This approach is highly effective because the address mappers can be built with significantly smaller silicon resources which yield a compact, power efficient design. This is a preferred approach to replicating a full multi-dimensional data structure.

The address mappers 52N can parse any input (logical) address(es) to any output (physical) address(es); thus the 'free' data structure segment will appear to steadily rotate through the entire data structure as new coefficients are computed and downloaded by the ACPCE. A strict rotation through the multi-dimensional data structure 52H, however, is not required. Should a region of the multi-dimensional data structure require more frequent updating due to the characteristics of the amplifier 64, then the ACPCE can schedule more computational resources to ensure that those associated correction coefficients are updated more frequently.

Each time the ACPCE downloads new coefficients to the 'free' segment, the entire memory address map of the 'free' address mapper 52N (logical to physical address parsing) does not need to be updated—just the sub-fraction of addresses that correspond to the swapped segment of the data structure. In this particular example only ¹⁄₁₂₈ of the address mapper would require updating. Thus the process is not significantly slower than that offered by the direct implementation of an entire second copy of the multi-dimensional data structure 52H. When the power and die savings are considered, this provides a significant commercial advantage.

The address mappers 52N may be constructed from re-programmable combinatorial logic or memory based look-up tables. Furthermore, the two address mappers may be reduced to a single address mapper which exploits a dual port memory architecture, provided steps are taken to arbitrate contention. In the event of a read and write contention scenario, the read command by the DCSP may be given higher priority so that the real time data flow is impaired. This design approach is feasible because the power requirements of the very small amount of dual port memory needed to implement the address mappers does not over burden the entire design.

The multi-dimensional data structure 52H and augmented segment 52M are preferably constructed from a single memory. Segmentation may therefore by considered an absttraction utilized for descriptive clarity.

5.6. Event Driven Capture Apparatus and Modes of Operation

Figure 45:
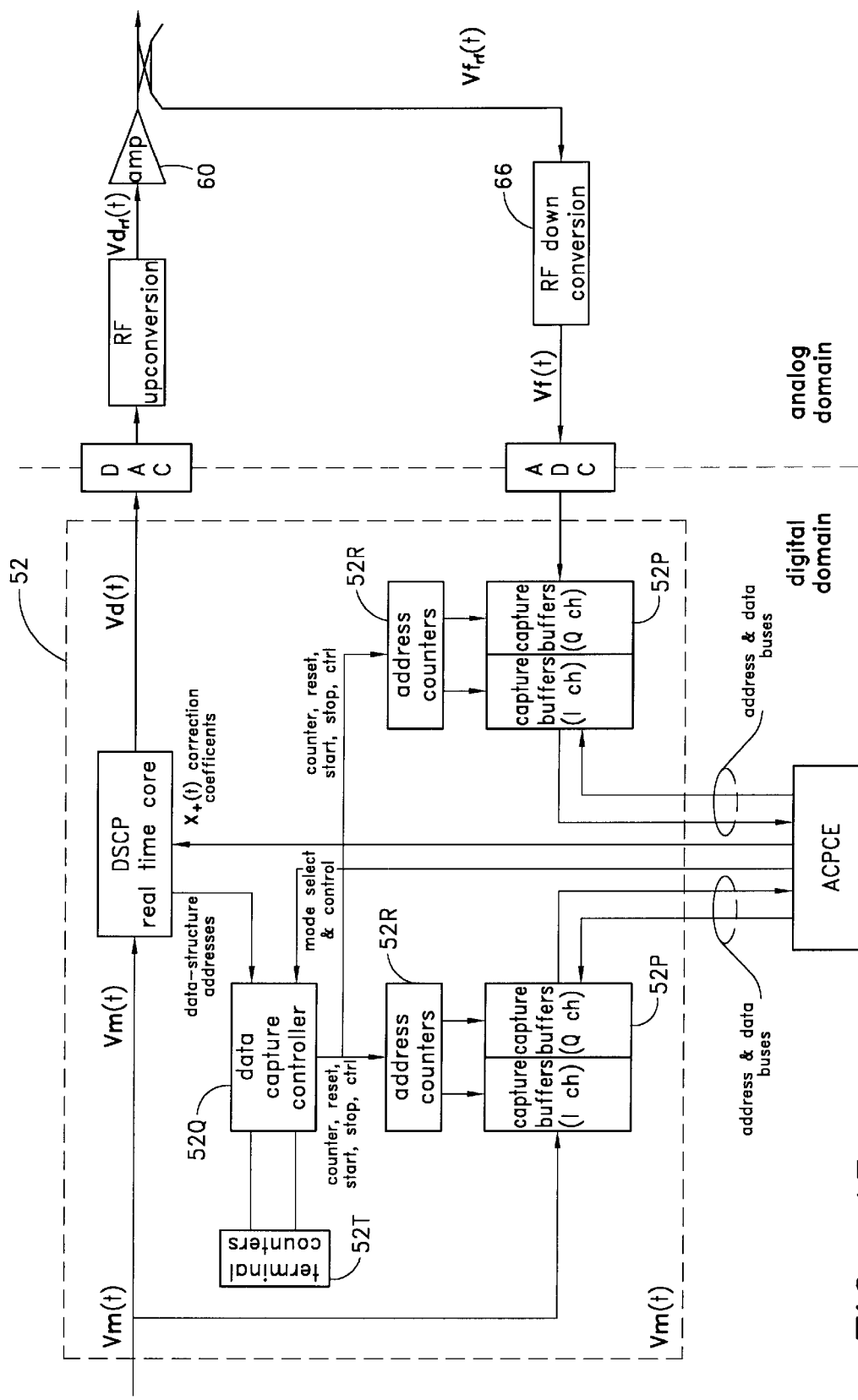
FIG. 45 illustrates a DCSP augmented with event-driven data capture circuitry.

As discussed in Section 2.2, operation of the predistortion system ordinarily proceeds with the ACPCE capturing sequences of digital input signal samples and sequences of the digitized observed feedback signal from the power amplifier 64. This could ordinarily be achieved by augmenting the ACPCE, which is preferably a programmed DSP or microprocessor, with input FIFO's or other memory data buffers which are fed with the appropriate data streams. An alternative approach, which is illustrated in FIG. 45, is to fabricate the DCSP fast signal processing engine with internal signal capture buffers 52P. This approach is desirable because it permits a smaller, highly integrated solution that is ultimately more power efficient than a discrete component design. Furthermore, as will be subsequently disclosed, embedding the signal capture buffers within the DCSP permits additional enhanced functionality to be easily implemented. FIG. 45 illustrates the DCSP augmented with digitized input signal and observation signal capture buffers and a simple data capture controller that permits different operational modes to be invoked.

As illustrated in FIG. 45, the DCSP is augmented with two capture buffers/memories 52P, each being able to store sequences of IQ complex baseband data or a stream of real digital IF signal sequences. These buffers are under the direct control of a data capture controller 52Q that is resident within the DCSP ASIC or FPGA. The hardware is constructed so that the ACPCE can directly read the contents of each individual data buffer 52P over an address and data bus. Although these buses are illustrated as separate entities in FIG. 45, it will be recognized that the entire internal organization of the DCSP may be designed such that all individual functions are resident peripherals on a single address, data and control bus. Separate control, data and address buses are shown for descriptive clarity.

An important feature of the design is that the address counters 52R are controlled by the data capture controller 52Q which may be reset, started, stopped and reset with a new increment rate. A useful function also provided by the data capture controller is to insure that the input and observational signal buffers remain synchronized throughout their operation. This permits the ACPCE to compute the integer and fractional delay that occurs between the two sample streams due to the external analog circuitry only once. Independent address counters may be utilized to permit the ACPCE the luxury to align the captured data streams to the nearest integer by programming counter offsets into the address counters. This function helps to ease the data manipulation software burden for the DSP. The data capture controller also monitors the addressing circuitry that is utilized within the DCSP real time kernel to access specific correction coefficients as a function of the input waveform. Specifically, the DCSP core provides the exact address(es) that are used to index the multi-dimensional data structure 52H that contains the correction coefficients.

In a preferred embodiment, the ACPCE may command this data capture controller to operate in one of four modes:

mode 1:—free run mode 2:—capture upon command mode 3:—free run event driven capture with delayed cessation mode 4:—event driven capture Each mode is described below with further reference to FIG. 45.

5.6.1. Capture Mode 1

Mode 1 is the free running mode, and operation occurs in the following manner. The address counters 52R are set to run continuously, incrementing with each sample period. At each sample instant (clock tick) the digitized input and observed signals (complex baseband or digital IF) are stored in the appropriate buffers 52P. If the address counters exceed the maximum address, they automatically reset to the base address and start incrementing upward with each sample period (clock tick). Thus the buffers are continually filled with data as the cyclic addressing proceeds.

This mechanism is continually exercised until the ACPCE issues a command to the data capture controller 52Q to cease capture. This permits the ACPCE the ability to read the captured data from the buffers 52P. The cessation of data capture can occur immediately, or alternatively the counters can be permitted to allow data collection to continue until the base address is next encountered. Both mechanisms permit the ACPCE to collect a full buffer of sampled signals, however the second approach provides an implied reference point to the effective starting point of the continuous data sequence.

If the first approach is used, the ACPCE can read the address counters' state to determine when the data captured ceased. Naturally, when the ACPCE has uploaded the sequences, integer and fractional delay differences between the two sequences need to be computed before error signal sequences can be derived. Once the ACPCE has up loaded the data, it may command the data capture controller 52Q to resume collecting data by restarting the address counters 52R. This mode of operation is attractive because it permits the processing latency between capturing and analyzing data to be minimized. This occurs because the buffers will be full, with the very latest data that passed through the DCSP core, the moment the ACPCE has finished processing and analyzing the previous data set.

5.6.2. Capture Mode 2

Mode 2 is the "capture upon command" mode. This operating mode permits the DCSP to be utilized in a power saving mode. The data capture controller 52Q suspends collection of data by freezing the address counters 52R, and data collection is only re-enabled by command from the ACPCE. This saves power consumption because the memories which constitute the capture buffers 52P are not continually exercised with writing the latest data sample captured to a particular address location (and by inference over writing the previously stored data). This saves a significant amount of power because the memories are not being continually exercised with changes in data state.

Typically this mode is utilized in applications where the ACPCE is used to control multiple DCSP entities, such as in smart antenna arrays and hot swap architectures as described above. When operating in such a system, the ACPCE initiates data collection by commanding a specific DCSP's data capture controller 52Q when adaption is required or scheduled. In practice, the ACPCE may set a register bit embedded within the DCSP that is monitored by the data capture controller; in response, the data capture controller 52Q may interrupt or set a flag bit when the data capture process has been completed, alerting the ACPCE of data availability.

5.6.3. Capture Mode 3

Mode 3 is the "free run event driven capture with delayed cessation" mode. This mode of operation is important to overcoming a particular difficulty that is encountered when using multi-dimensional data structures 52H in the predistortion system. That is, particular combinations of an amplifier and signal source characteristics may result in certain regions of the multi-dimensional data structure being rarely accessed. This causes problems because the majority of the data storage elements may be updated on a regular basis, but unfortunately the rarely exercised regions may be populated with incorrect coefficients.

A particular example is when the EDGE waveform is utilized. This waveform is designed to have a very low probability of a low envelope absolute magnitude, thus nearly eliminating the probability that the lower amplitude and integrated past amplitude regions of the data structure are exercised. This problem is exacerbated when, while operating in mode 1 or 2, the ACPCE only processes a fraction of the input data and thus captures and uploads data less frequently.

Mode 3 operation obviates this problem by continually capturing data in a manner identical to mode 1 while searching for a rare events. This is achieved by permitting the ACPCE to program the data capture controller 52Q with a range of address/data structure indices that define a sub region within the multi-dimensional data structure 52H. The data capture controller operates by continually comparing this specified region with the sub region of the multiple dimension data structure that is instantaneously utilized by the DCSP core. Should the characteristics of the input signal exercise the specified sub region, the data capture controller starts a terminal counter 52T with a period set to exactly one half the time (number of samples periods) required to fill the data buffers 52P.

When the terminal counter 52T expires, the data capture controller 52Q stops the address counters 52R and freezes the data in the buffers 52P. This permits status flags or interrupts to be set which alerts the ACPCE to retrieve the captured data (and address counter values) that includes the rare transmission event. The delayed suspension/cessation of the data capture process is an important element because it enables data prior to and after the rare event to be captured. This permits the ACPCE algorithms to compute the most optimal coefficients for the rarely exercised region within the multi-dimensional data space. Depending upon the application, the terminal counter 52T that defines the suspension point may be re-programmed with a different value so that more pre-event and/or post-event data can be captured.

5.6.4. Capture Mode 4

Mode 4 is the event driven capture mode, and operation occurs in a manner very similar to mode 3. Mode 4 operates by freezing the address counters 52R until the specified rare sub-region of the multi-dimensional data structure 52H is exercised. Once the sub-region has been entered, the data capture controller 52Q immediately releases the address counters 52R while simultaneously starting the terminal counter 52T. Once a full buffer of data has been captured i.e., the terminal counter has expired, the data capture controller suspends the data capture process and sets the appropriate flags or interrupts to alert the ACPCE to the availability of data. Mode 4 is primarily utilized as a power saving mode where permanent data collection is not desired. The approach is suboptimal in the sense that post rare event data can only be captured. This compromise could be obviated if small input signal FIFO's prior to the data capture buffer inputs are utilized to delay the captured data from the transition event.

5.6.5. Technology Summary

The approach outlined above for modes 2 and 3 is a highly optimal solution because it directly utilizes the DCSP's multi-dimensional data structure's addressing computations to distinguish rare events. The comparison is easily achieved by utilizing programmable logic to create simple bitmaps that need to be compared for logical equivalence. This is also attractive because the power consumption utilized by the device is also reduced because independent circuitry is not required to detect the rare events.

The ACPCE can identify the infrequently accessed areas of the data structure 52H by, for example, maintaining a multi-dimensional access histogram which reveals the frequency with which each region has been accessed.

5.7. Temperature Sensor LUT operation

Figure 46:
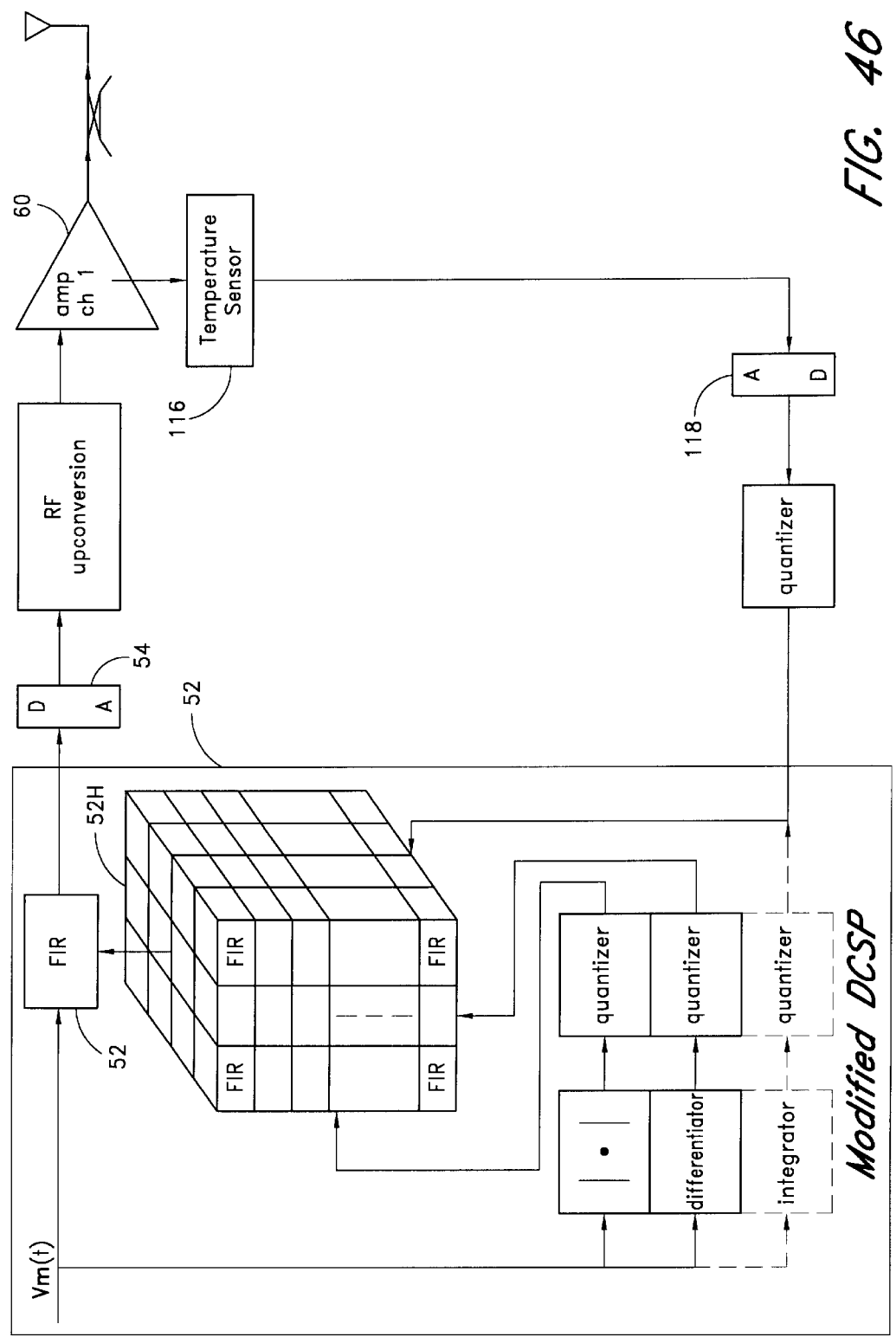
FIG. 46 illustrates an embodiment in which the amplifier's transistor die temperature is measured and provided to the ACPCE.

FIG. 46 illustrates a modified DCSP system 52 in which the estimation of the amplifier transistor's die temperature is obviated by directly utilizing a temperature sensor 116 embedded in the transistor/amplifier assembly. As depicted in the drawing, the temperature sensor and associated A-to-D converter 118 take the place of the signal integrator. This approach reduces the amount of signal processing and ACPCE estimation processing that has to be undertaken. The approach is attractive because the sampling rate of the transistor die temperature is quite slow, for it is defined by the thermal time constant (typically hundreds of milliseconds) of the amplifier assembly.

In operation, the temperature sensor's output is sampled by an A/D converter 118, quantized, time stamped to enable correlation with the stimulating input signal Vm(t), and then stored in memory. This stored temperature data is subsequently used by the ACPCE compute DCSP compensation parameters as a function of amplifier die temperature. In addition, as illustrated in FIG. 46, real time temperature readings are quantized and then used as a third index to the multi-dimensional data structure 52H.

5.8. Utilization of Interpolation in the DCSP for Improved Noise Floor and Linearity As explained above, the wideband predistorter system operates by repeatedly observing the wideband amplifier's output signal Vf(t) and the input information bearing signal Vm(t). The ACPCE then computes the errors between the observed and ideal signals to create an updated set of DCSP compensation parameters that should reduce the error between the ideal and observed signals. In practice, any change in the DCSP compensation parameters, when downloaded will cause a step change in the waveform fed to the amplifier input.

In highly specialized scenarios where the small step change causes an unacceptable short term rise in spurious component generation, the effect can be reduced by interpolation of the DCSP compensation parameters. When interpolation is used, the normal update vector $X_+$ of new compensation parameters, as defined by Equation 31, is not directly downloaded to the DCSP.

$$[X_t]=[X_-]+\Delta \text{Verror}[Vm(t)] \qquad \text{Equation 31}$$

Rather, the downloaded vector is modified by interpolation, and multiple downloads occur for a period of time with the final download being defined by the target update $X_+$. The downloaded update vector is defined by Equation 32 where $\alpha$ and $\beta$ represent the scaling coefficients and N represents the number of iterations over which the total download process will occur.

Equation 33 defines that the overall update process provides update vectors which do not exhibit overall gain changes as a result of interpolation. To those familiar with numerical interpolation, Equations 32 and 33 define simple linear interpolation. Higher order interpolation functions could alternatively be used, but experimental experience has shown that linear interpolation is adequate for suppressing spurious responses in critical applications such as Motorola's InFlexion paging system.

$$X_t = \frac{\alpha X_+}{N} + \frac{\beta X_-}{N} \qquad \text{Equation 32}$$

$$N=\alpha+\beta \qquad \text{Equation 33}$$

$$X_+ = \frac{NX_+}{N} + \frac{0X_-}{N} = X_+ \qquad \text{Equation 34}$$

The iterative download approach proceeds by computing $X'_+$ on the basis that the $\alpha$ and $\beta$ coefficient weights the overall download to favor the current state vector $X_-$ whilst including a modest contribution from the new update vector $X_+$. As the process proceeds, $\alpha$ and $\beta$ are adjusted to increasingly favor the new update vector $X_+$. Equation 34 defines the last interpolated download which identifies that the last update is the desired overall update $X_+$ without any contribution from the current parameter vector $X_-$, ($\alpha$=n, $\beta$=0).

Figure 47:
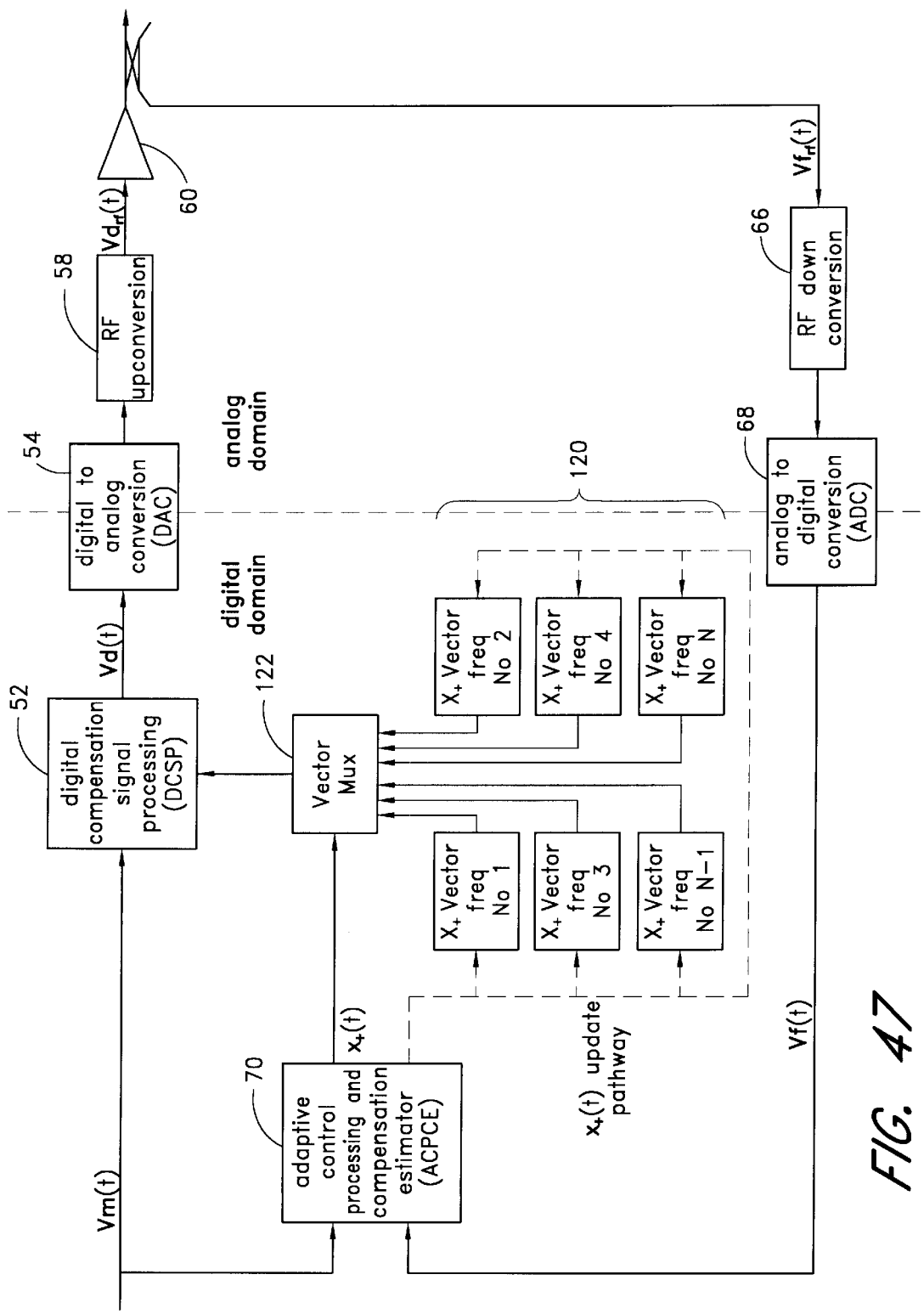
FIG. 47 illustrates an embodiment in which compensation parameters are stored and provided to the DCSP for each carrier frequency within a hopping sequence.

5.9. Multiple Memory Allocations for Different PSD Combinations/Channel Allocations Frequency hopped spread spectrum systems, such as the second generation GSM and EDGE cellular system, operate over very wide operating bandwidth. In many systems, and especially those operating at LMDS frequencies (40 GHz), the operating bandwidth exceeds the correcting bandwidth of the basic wideband predistorter design described above. FIG. 47 illustrates an extension to the basic design where the ACPCE is enhanced by providing extended memory storage capabilities 120 which permit the ACPCE to store a set of DCSP coefficients for each carrier frequency (or a subset of close carrier frequencies) within the frequency hopping sequence. This may be accomplished by adding an additional dimension to the data structure 52H that represents the carrier frequency. As the carrier frequency hops throughout its operating bandwidth, a vector multiplexer 122 selects, under the control of the ACPCE, the appropriate DCSP parameters (vector) to be loaded into the DCSP for the next frequency in the sequence. The parameters may be loaded into the DCSP during the dwell time between transmission bursts.

In simple systems, the ACPCE may be provided with explicit new frequency commands from the base station's radio resource management entity which identifies the hopping sequence and current hop frequency. Alternatively, the ACPCE may determine the hopping sequence executed by the base station. This is readily achieved by the ACPCE because each unique hopping frequency will identified by a specific loop gain and phase shift. Furthermore, each carrier frequency of operation will be identified by a unique distortion signature which the ACPCE may compute and use to identify a particular carrier frequency.

5.10. Dual FIR Filter Wideband Predistorter Construction

The nonlinearity characteristic exhibited by an amplifier becomes increasingly complex as the power handling capability of the amplifier increases. In very high power applications, the DCSP architecture outlined above may become prohibitively large, and as such, prevent effective implementation. Specifically, if the dimensionality of the FIR filter's data structure 52H becomes too large, data routing pathways in the ASIC may prevent the desired level of DCSP complexity from being implemented.

Figure 48:
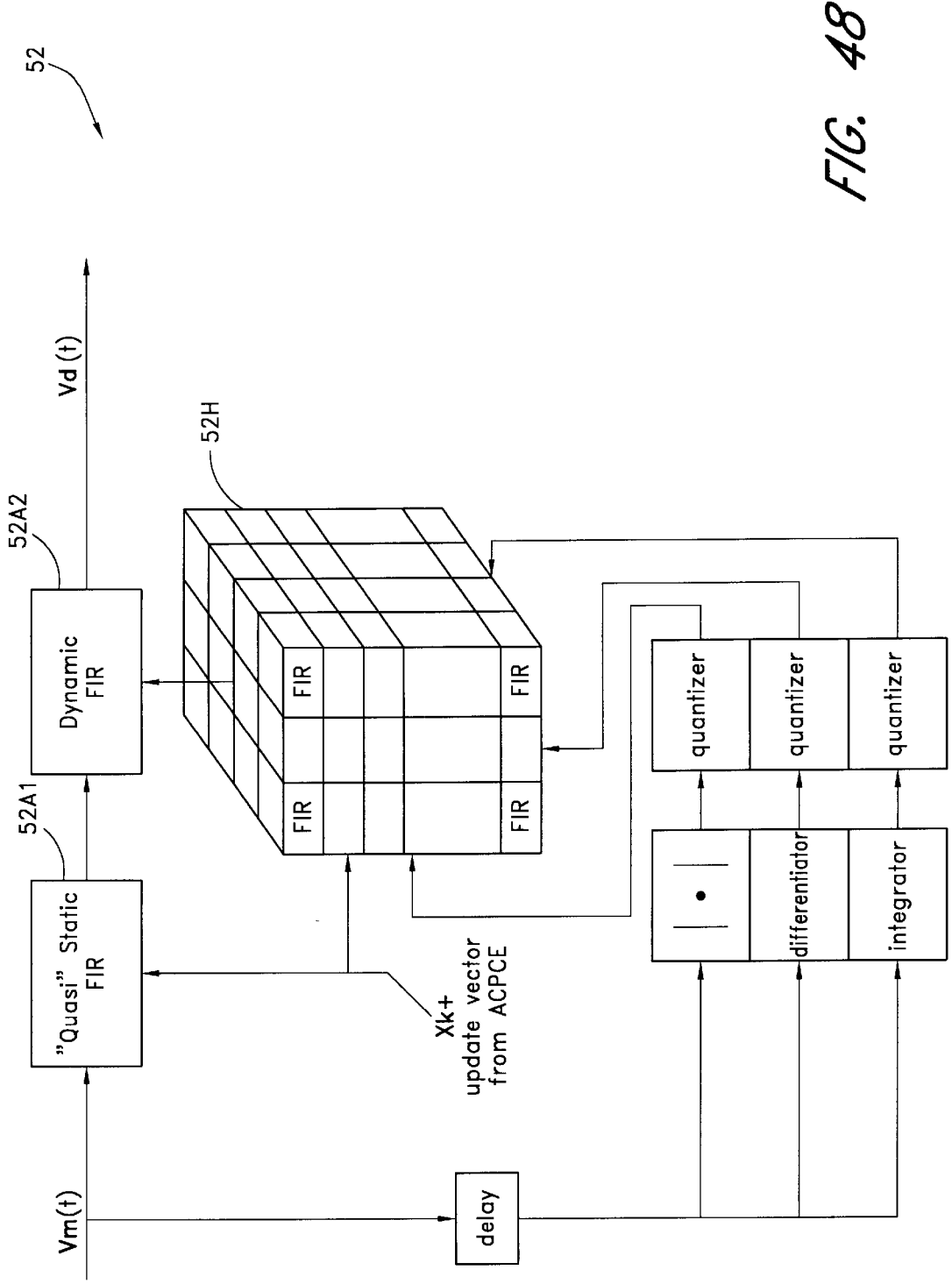
FIGS. 48 and 49 illustrate embodiments in which the DCSP's filtering function is performed by a quasi static filter cascaded with a dynamic filter.

FIG. 48 illustrates an alternate design in which the FIR filter coefficients stored in the data structure locations are separated into a bulk "quasi" static FIR filter 52A1 and a dynamic FIR filter 52A2. As with the previously described DCSP structure, the dynamic FIR filter's coefficients may be updated for each sample instant. The coefficients of the quasi static FIR filter, on the other hand, are updated by the ACPCE on a significantly less frequent basis, at the direction of the ACPCE. With this approach, the static FIR filter 52A1 provides a bulk frequency dependent correction, and the dynamic FIR filter 52A2 provides fine adjustments. For example, a standard DCSP design may be based around an 11 tap FIR filter, where as the design illustrated in FIG. 48 may use a 9 tap quasi static FIR filter followed by a 3 tap dynamic FIR filter. Such an approach dramatically reduces the storage and data pathway complexity for implementation of the DCSP. The orders of the filters are largely driven by the characteristic of the nonlinearity exhibited by the amplifier.

Figure 49:
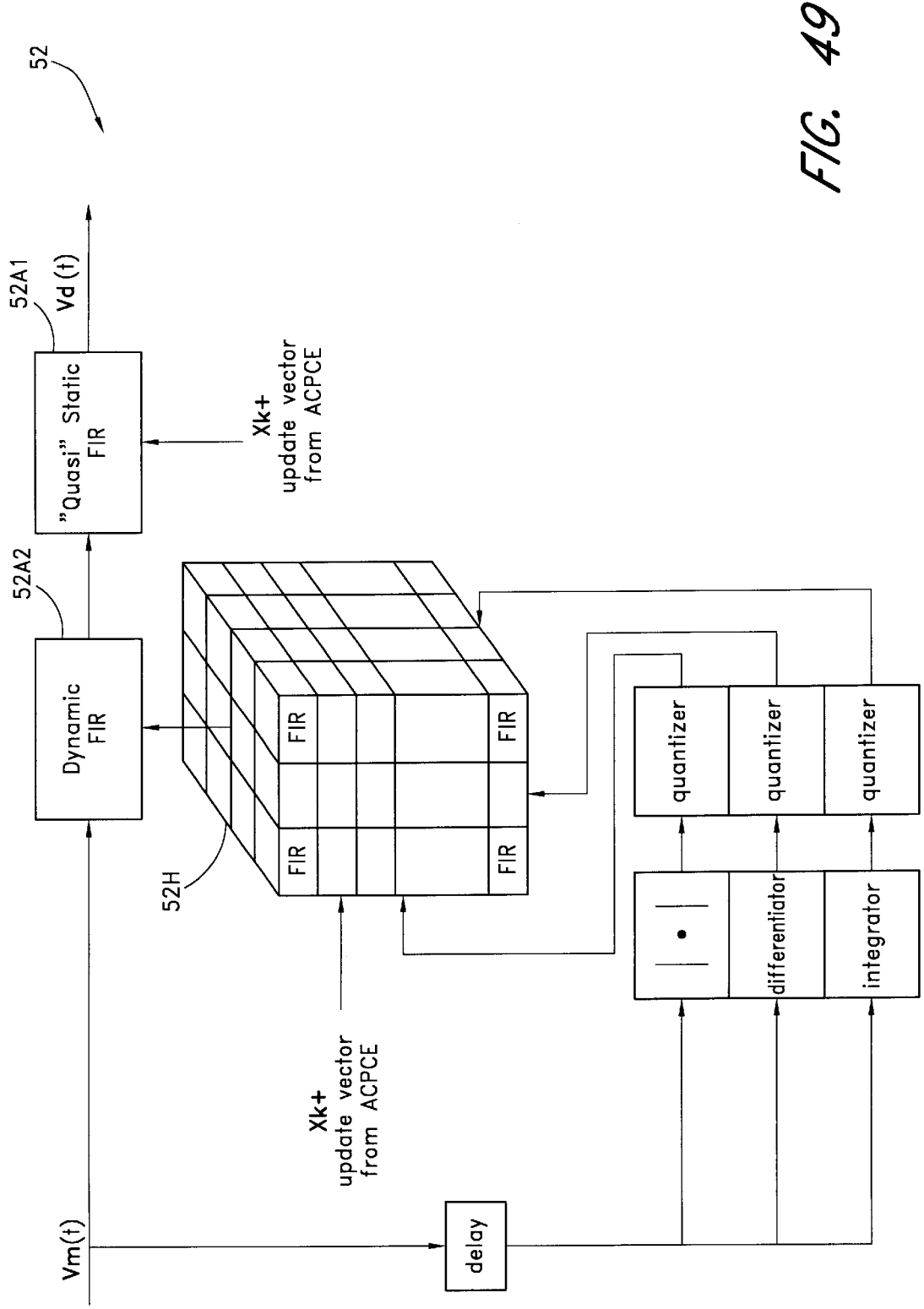

The two filters 52A1, 52A2 may be cascaded in reverse order, as in FIG. 49, without impact since the convolution of the two filters reproduces an identical result.

A further enhancement is to permit the quasi static filter 52A1 to be driven from a data structure of significantly smaller dimension than that of the main nonlinearity compensation data structure 52H. With this approach, the original predistortion data structure 52A is effectively transformed into a cascade of predistortion structures.

5.11. Functional Wideband Predistorter Construction Approach

If the nonlinearity exhibited by the amplifier is exceptionally severe, then the size and complexity of the DCSP's data structure 52H increases in a commensurate manner. An alternate approach to utilizing a large memory structure is to realize that at some point it is actually more efficient to compute the tap values dynamically rather than store the pre-computed values for all possible input scenarios. In this case, the ACPCE computes the shape of the tap coefficient values over some multi-dimensional surface and reduces these values to a simple multi-variable function. The coefficients of this function are then loaded into the DCSP, where each tap of the dynamic filter is recomputed on a sample-by-sample basis.

Figure 50:
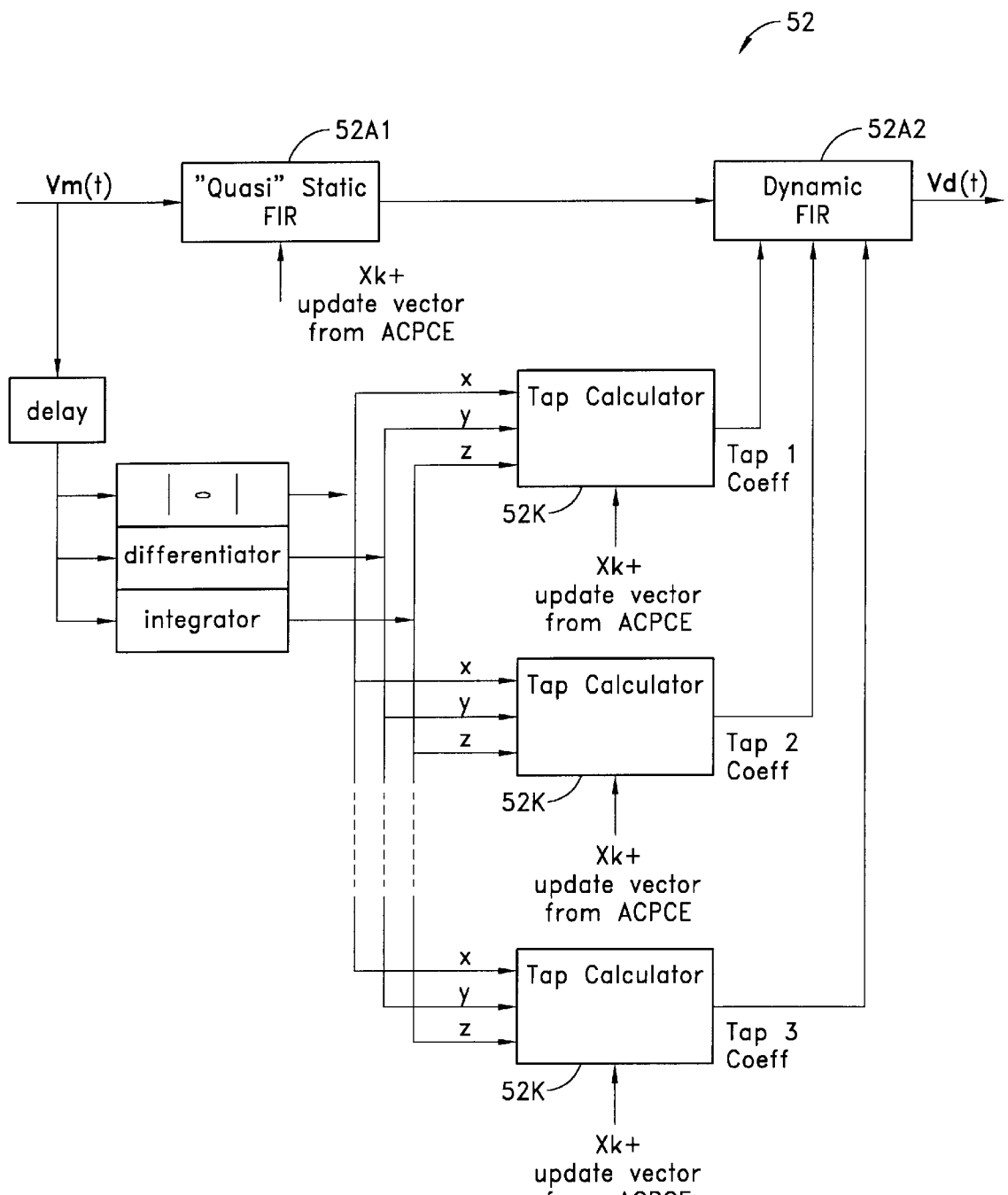
FIG. 50 illustrates an embodiment in which compensation parameters are generated on-the-fly, rather than being retrieved from a data structure.

FIG. 50 illustrates an embodiment which uses this approach combined with the use of dynamic and quasi static FIR filters as described in the previous section. The data structure 52H is replaced in-whole or in-part with tap calculators 52K. The tap calculators calculate the correction coefficients on-the-fly using the same signal characteristics that were used to index the data structure 52H, and using bulk coefficient data provided by the ACPCE. These dynamically updated coefficients are loaded into the dynamic FIR filter 52A2 (preferably on a sample-by-sample basis), while the quasi static filter 52A1 receives less frequent updates from the ACPCE.

This technique represents a computationally more complex approach but yields a design that is potentially easier and smaller to implement in silicon. Typically a 12×12 multiplier in silicon requires 2000 transistor gates and each bit of memory storage requires a minimum of 4 gates. Thus, for a given level of complexity, it is relatively easy to determine whether the DCSP should be constructed from a functional tap computation approach or from a mass data structure approach (or a hybrid approach). Naturally, the approach outlined in this section increases the computational burden upon the ACPCE because of the surface functional fitting requirement. The approach is also attractive because the tap coefficients will not be subject to quantization noise due to the continuous function that is used to compute the tap values as a function of the variation in envelope properties.

5.12. Fast AGC Loop for Constant Operating Point

It is not uncommon for very high power amplifiers (typically greater than 10 Watt peak power capability) to exhibit small variations or oscillations in bulk gain and phase response as a function of time. Typically, these oscillations have periods that span several seconds to several minutes. Ordinarily, such oscillations are eliminated by the adaptation process executed by the ACPCE. The ACPCE continually adjusts the DCSP's compensation parameters so that the loop gain, and hence amplifier's response, maintains a constant bulk phase and gain response. However, in scenarios where the amplifier may oscillate faster than the ACPCE can adapt, the inclusion of a fast automatic gain control (AGC) is highly desirable for maintaining performance. A typical scenario is the antenna array application (Section 5.2) where the ACPCE is responsible for supervising and ensuring that the DCSP's compensation parameters for multiple amplifier assemblies are current.

Figure 51:
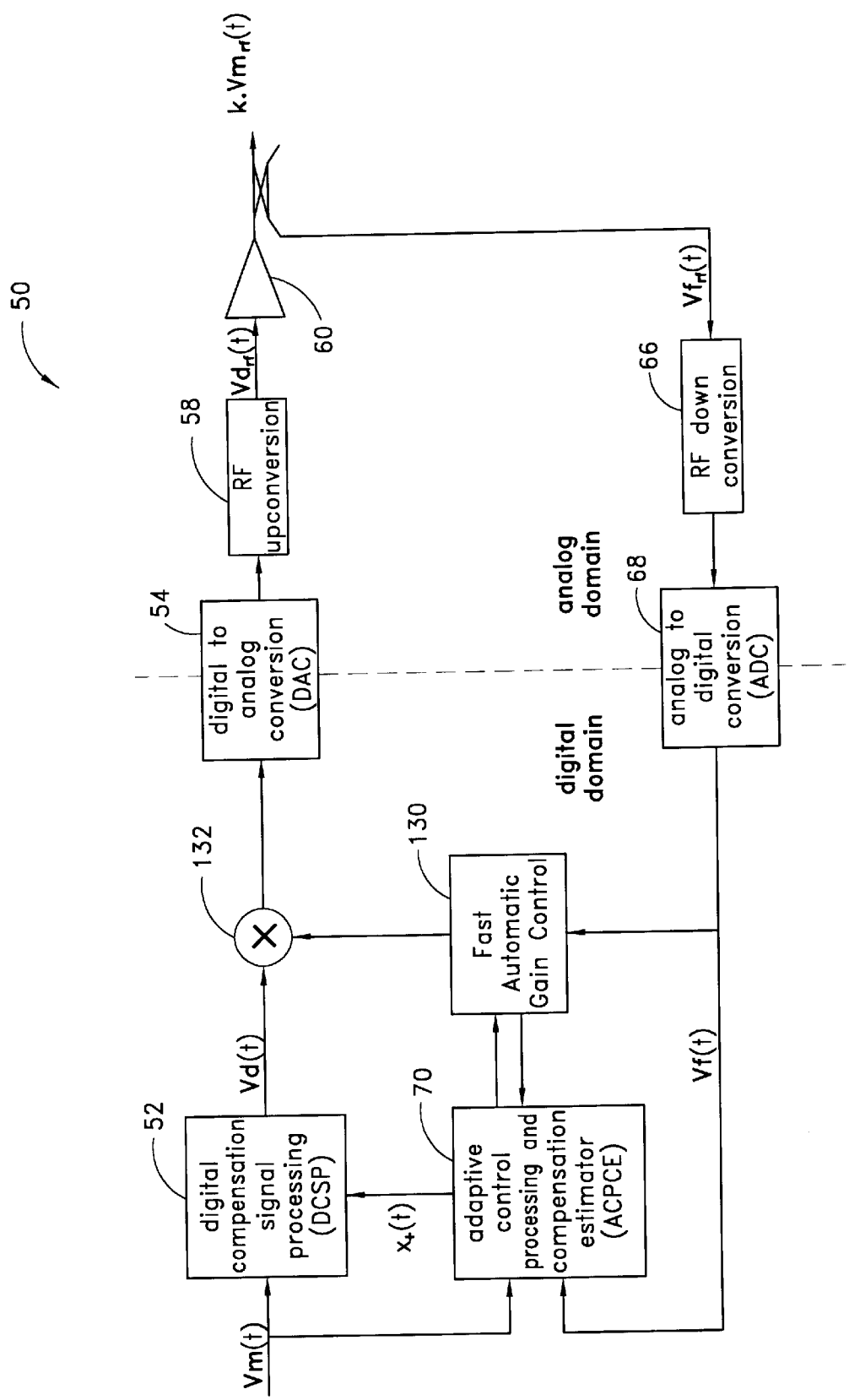
FIG. 51 illustrates an embodiment which uses fast automatic gain control.

FIG. 51 illustrates how a fast AGC component 130 can be incorporated into the basic amplifier system 50 for this purpose. The AGC 130 manipulates the bulk loop gain via a multiplier 132 so that the bulk loop gain observed by the DCSP 52 does not appear to drift or oscillate. The ACPCE thus computes coefficients that merely eliminate the variations in the multi-variable dependency of the amplifier upon the input signal's envelope, such as frequency dependent or past average power profile or the rate of change of the complex envelope.

This approach is attractive because it permits the ACPCE to rapidly adjust a single AGC parameter and return to the detailed and extended computations used for the update of an alternate amplifier's DCSP's compensation parameters. That is, the ACPCE could rapidly adjust 8 independent amplifiers of an antenna array and then return to adapting the DCSP's coefficients of the first amplifier. Prior to computing the DCSP coefficients for the second amplifier, the ACPCE could rapidly readjust the AGC parameters of an entire set of antenna array amplifiers. The antenna design described in Section 5.2 can be used for this purpose.

5.13. Reduction in Data Structure Noise by Localized Dimension Updating

The wideband noise floor exhibited by the wideband predistortion architecture is partially defined by the adaptation noise contained within the DCSP's data structure 52H. That is, the DCSP compensation coefficients contained within the data structure are point estimates of the true nonlinearity needed to compensate for the amplifier's characteristic. Furthermore, because of the adaptation process, these estimates are all subject to independent random errors. These inaccuracies cause the overall system response to exhibit wideband noise, because as the signal trajectory traces a loci through the data structure, each set of used compensation parameters imparts an error contribution which is independent of the error incurred by the previous set of compensation parameters.

This contribution to the overall wideband noise characteristic of the design can be overcome by expanding the DCSP compensation coefficient update process. Ordinarily, the input signal trajectory and associated second order statistics cause a specific entry in the DCSP's data structure 52H to be selected for use and subsequent updating. The update is defined by Equation 35, where X represents a single data structure entry for a set of compensation parameters, the product of Verror and the signal vector Vm(t) represent the overall magnitude and direction of the update vector, and A represents the update gain.

$$[X_+] = [X_-] + \Delta \text{Verror}[Vm(t)] \quad \text{Equation 35}$$

Ordinarily, this update is applied to the single data structure entry. However, since the amplifier is characterized by a smooth nonlinear function with continuous partial derivatives, an update vector applied at a particular point in the multi-variate space is also strongly applicable to points closely located. Thus, the update equation defined by Equation 46 may be updated according to Equation 36.

$$[X_+]_{x,y,z} = [X_-]_{x,y,z} + \Delta(f((x-n)^2+(y-m)^2+(z-p)^2))\text{Verror} [Vm(t)]|_{n,m,p} \quad \text{Equation 36}$$

The equation defines that if the point (n,m,p) in the data structure space has been selected for updating, then all other points within the data space are also updated. However, the update gain $\Delta$ is now a function of the distance between the initial indexed point (n,m,p) and the updated entry (x,y,z). Naturally, this function equals unity when the initial indexed point and the updated entry are identical. Otherwise, the function rapidly decays to zero so that only the very localized data structure points surrounding the initial indexed point are updated.

This approach is attractive because the updates now become correlated and connected to the neighboring entries within the data structure 52H. This serves two purposes because it ensures the partial derivatives of the quantized multi-variate space captured by the DCSP data structure are continuous. Furthermore, because the error contributions are now correlated from entry to entry, the wideband noise generated by adaptation errors is significantly reduced.

The ACPCE preferably does not blindly execute all updates, but rather performs updates for which the update gain is non zero. In practice, Gaussian functions have proven to be ideal for the update gain. Naturally, a decaying function may also be used.

5.14. Frequency Domain Smoothing

Management of overall system noise is an important consideration when dealing with digitally controlled amplifier designs. As discussed in the previous section 5.13, the wideband predistorter can introduce wideband noise due to independent adaptation errors that are associated with individual sets of FIR filter compensation coefficients stored within the DCSP data structure. An alternative method of reducing these effects is to use frequency domain smoothing upon the DCSP coefficients. This function is preferably undertaken by the ACPCE which symmetrically zero pads the time domain FIR filter coefficients and converts each FIR filter's impulse response, h(t), to its frequency domain, H(w), counterpart via the FFT. In the frequency domain, the filter's frequency domain response, H(w), is modified by computing a new H(w) that is derived from a weighted sum of the frequency domain response of the neighboring filters. This process is carried out in an identical manner for each filter stored in the DCSP's data structure 52H. When the process is complete, each new H(w) FIR filter response is converted back to the time domain, via the inverse FFT, and truncated to form a modified version of the original FIR filter's time domain impulse response.

The purpose of filtering in the frequency domain is to ensure that upon the re-computation of each filter's updated time domain impulse response, h(t), the partial derivatives of the nonlinear function approximated by the DCSP's data structure 52H are continuous. The result of this process is a suppression of the noise floor. Specifically, the errors in the nonlinear compensation process that are invoked as the input signal trajectory traces a loci through the DCSP's data structure are correlated, which suppresses the generation of wideband noise.

6. CONCLUSION

This inventive predistortion architecture, methods and components set forth above are applicable generally to any amplifier for bandlimited wideband RF signals. The techniques can be used for multiple signals and for any modulation scheme or combination of modulations. Where multiple signals are amplified, the signals can each have any modulation type.

The bandwidth of operation preferably does not exceed one octave of carrier frequency because of the harmonics generated in the nonlinear amplifiers. This is a normal limitation on the use of any nonlinear amplifier. In most applications at high RF frequencies the bandwidth will be limited by the maximum clocking frequency of the digital processing hardware.

The predistortion architecture provides an alternative to the existing techniques of Cartesian feedback, LINC and feedforward. Each technology has its advantages and disadvantages. A system which uses the predistortion techniques set forth herein is generally simpler to implement than the other linearized amplifier types. Furthermore, the approach provides linearization performance that surpasses previously known and documented predistortion linearized power amplifiers.

The power conversion efficiency is determined in large part by the type of signals to be amplified. For amplifying a single channel of a QAM or PSK type signal, the wideband digital predistortion efficiency is better than for other amplifier types. For high peak-to-average ratio signals, the efficiency is not significantly different from the other methods. The purity of the output signal is excellent and is better than the current feedforward products.

The digital control features of the invention could be implemented in a custom integrated circuit for application to a variety of amplifier combinations and in supporting various up and downconversion systems.

The predistortion architecture is commercially significant because, for example, wideband third generation cellular basestation designs for W-CDMA, IMT-2000 and UMTS-2000 require ultra linear power efficient multicarrier amplification. Currently, this requirement is not fulfilled by commercially available amplifier designs. The preferred embodiments of the invention fulfil this commercial requirement. The design is also applicable to other commercial systems such as point-to-point, point-to-multipoint, wireless local loop, MMDS and LDMS wireless systems. The approach is also applicable to existing cellular systems and may be used to reduce the cost of design in subsequent manufacturing cost reductions. The predistortion techniques will also find utility in the satellite, cable broadcast and terrestrial broadcast industries where linear amplification is required. The design is particularly suitable for applications where digital radio and television signals require amplification without incurring distortion. Other embodiments and applications for the inventions will be apparent to those skilled in the art.

Although the invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A transmission antenna array system comprising:
    a plurality of amplification chains, each amplification chain having an output coupled to a respective antenna of the array;
    a plurality of compensation circuits, each compensation circuit coupled to, and configured to digitally predistort an input transmission signal to, a respective amplification chain using a dynamically updated set of compensation parameters; and
    a processing unit that monitors the input transmission signals to, and corresponding output signals from, each of the plurality amplification chains, and processes said input transmission and output signals to adaptively generate updates to the compensation parameters used by each of the plurality of compensation circuits.

2. The transmission antenna array system as in claim 1, wherein the processing unit comprises a single general purpose microprocessor that executes a program to generate the compensation parameter updates for the plurality of compensation circuits.

3. The transmission antenna array system as in claim 1, wherein the processing unit comprises a single digital signal processor that executes a program to generate the compensation parameter updates for the plurality of compensation circuits.

4. The transmission antenna array system as in claim 1, wherein each amplification chain includes a coupler that generates a respective radio frequency (RF) observation signal, and the system further comprises:

a multiplexer that selects between the RF observation signals; and a circuit for RF downconverting and converting to digital form an RF observation signal selected by the RF multiplexer, to thereby generate digital observation signals for use by the processing unit.

5. The transmission antenna array system as in claim 4, further comprising an input signal multiplexer that selects between the input transmission signals to provide a selected input transmission signal to the processing unit.

6. The transmission antenna array system as in claim 1, wherein each compensation circuit comprises a digital filter from which compensation parameters are read from a respective multi-dimensional data structure, wherein compensation parameters are indexed within and read from each data structure according to a least two different input transmission signal characteristics.

7. The transmission antenna array system as in claim 6, wherein each multi-dimensional data structure has a first dimension that corresponds to an instantaneous signal amplitude or instantaneous power, and has a second dimension that corresponds to an integrated signal envelope.

8. The transmission antenna array system as in claim 6, wherein the compensation circuits comprise finite impulse response predistortion filters for which sets of filter coefficients are read from the multidimensional data structures.

9. The transmission antenna array system as in claim 1, wherein each of the plurality of amplification chains includes a respective radio frequency (RF) upconversion circuit.

10. The transmission antenna array system as in claim 1, wherein the plurality of amplification chains provide for independent power amplification of each signal fed to each respective antenna.

11. In a transmission antenna array system comprising a plurality of amplification chains, a method of predistorting input transmission signals to the amplification chains, comprising;

providing a plurality of compensation circuits, each compensation circuit coupled to, and configured to digitally predistort an input transmission signal to, a respective amplification chain using a dynamically updated set of compensation parameters, wherein each amplification chain has an output that is coupled to a respective antenna of the antenna array system; and with a single processing module used on a time-shared basis, monitoring the input transmission signals to, and corresponding output signals from, each of the plurality amplification chains, and processing said input transmission and output signals to adaptively generate updates to the compensation parameters used by each of the plurality of compensation circuits.

12. The method as in claim 11, wherein the processing module comprises a single general purpose microprocessor that executes a program to generate the compensation parameter updates for the plurality of compensation circuits.

13. The method as in claim 11, wherein the processing module comprises a single digital signal processor that executes a program to generate the compensation parameter updates for the plurality of compensation circuits.

14. The method as in claim 11, wherein each amplification chain includes a coupler that generates a respective radio frequency (RF) observation signal, and the method further comprises:

selecting between the RF observation signals with an RF multiplexer; and downconverting, and converting to digital form, the RF observation signal selected by the RF multiplexer, to generate a digital observation signal for use by the processing module.

15. The method as in claim 14, further comprising selecting between the input transmission signals to provide a selected input transmission signal to the processing unit.

16. The method as in claim 11, further comprising storing the compensation parameters generated by the processing module in respective multidimensional data structures of the compensation circuits such that parameter sets are indexed within each data structure according to at least two different input transmission signal characteristics.

17. The method as in claim 16, wherein said input transmission signal characteristics include (a) an instantaneous signal amplitude or instantaneous power, and (b) integrated signal envelope.

18. The method as in claim 11, wherein the compensation parameters include sets of filter coefficients for use within finite impulse response predistortion filters of the compensation circuits.

19. The method as in claim 11, wherein the input transmission signals are wideband signals.

20. The method as in claim 11, further comprising upconverting a respective predistorted input transmission signal to radio frequency (RF) along each of the amplification chains.

* * * * *